US008637252B2

(12) United States Patent
Gupta et al.

(10) Patent No.: US 8,637,252 B2
(45) Date of Patent: *Jan. 28, 2014

(54) METHODS AND COMPOSITIONS FOR DETERMINING ALTERED SUSCEPTIBILITY OF HIV-1 TO ANTI-HIV DRUGS

(75) Inventors: Soumi Gupta, San Francisco, CA (US); Signe Fransen, San Francisco, CA (US); Ellen Paxinos, San Jose, CA (US); Neil T. Parkin, Belmont, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/296,370

(22) Filed: Nov. 15, 2011

(65) Prior Publication Data

US 2012/0135395 A1 May 31, 2012

(51) Int. Cl.
*C12Q 1/68* (2006.01)
*C12Q 1/70* (2006.01)
*A61K 49/00* (2006.01)

(52) U.S. Cl.
USPC .............. 435/6.12; 435/5; 435/6.1; 435/6.18; 424/9.2

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,631,734 A | 5/1997 | Stern et al. |
| 5,723,320 A | 3/1998 | Dehlinger |
| 5,744,305 A | 4/1998 | Fodor et al. |
| 5,834,758 A | 11/1998 | Trulson et al. |
| 5,837,464 A | 11/1998 | Capon et al. |
| 5,837,832 A | 11/1998 | Chee et al. |
| 5,919,523 A | 7/1999 | Sundberg et al. |
| 6,022,963 A | 2/2000 | McGall et al. |
| 6,040,138 A | 3/2000 | Lockhart et al. |
| 6,141,096 A | 10/2000 | Stern et al. |
| 6,156,501 A | 12/2000 | McGall et al. |
| 6,168,948 B1 | 1/2001 | Anderson et al. |
| 6,197,506 B1 | 3/2001 | Fodor et al. |
| 6,225,625 B1 | 5/2001 | Pirrung et al. |
| 6,242,187 B1 | 6/2001 | Capon et al. |
| 6,261,776 B1 | 7/2001 | Pirrung et al. |
| 6,284,465 B1 | 9/2001 | Wolber |
| 6,287,850 B1 | 9/2001 | Besemer et al. |
| 6,291,183 B1 | 9/2001 | Pirrung et al. |
| 6,308,170 B1 | 10/2001 | Balaban |
| 6,309,823 B1 | 10/2001 | Cronin et al. |
| 6,333,155 B1 | 12/2001 | Lockhart et al. |
| 6,342,355 B1 | 1/2002 | Hacia et al. |
| 6,355,432 B1 | 3/2002 | Fodor et al. |
| 6,379,895 B1 | 4/2002 | Fodor et al. |
| 6,391,550 B1 | 5/2002 | Lockhart et al. |
| 6,410,229 B1 | 6/2002 | Lockhart et al. |
| 6,451,536 B1 | 9/2002 | Fodor et al. |
| 6,489,114 B2 | 12/2002 | Laayoun et al. |
| 6,505,125 B1 | 1/2003 | Ho |
| 6,548,257 B2 | 4/2003 | Lockhart et al. |
| 6,551,784 B2 | 4/2003 | Fodor et al. |
| 6,617,112 B2 | 9/2003 | Beals |
| 6,670,124 B1 | 12/2003 | Chow et al. |
| 6,884,465 B2 | 4/2005 | Skarp et al. |
| 2004/0063191 A1 | 4/2004 | Huang et al. |
| 2005/0214750 A1 | 9/2005 | Parkin et al. |
| 2005/0214752 A1 | 9/2005 | Bonhoeffer |

FOREIGN PATENT DOCUMENTS

| | | | |
|---|---|---|---|
| WO | WO 97/27319 | 7/1997 | |
| WO | WO 99/67427 | 12/1999 | |
| WO | WO 0181624 A1 * | 11/2001 | ............... C12Q 1/68 |
| WO | WO 2006/133267 | 12/2006 | |

OTHER PUBLICATIONS

Bowie et al. Deciphering the Message in Protein Sequences: Tolerance to Amino Acid Substitutions. Science, New Series, Mar. 16, 1990, vol. 247, No. 4948, pp. 1306-1310.

Colonno et al. Identification of I50L as the Signature Atazanavir (ATV)—Resistance Mutation in Treatment-Naïve HIV-1—Infected Patients Receiving ATV-Containing Regimens. Journal of Infectious Diseases May 15, 2004, vol. 189, p. 1802-1810.

Abravaya, K. et al., "Detection of point mutations with a modified ligase chain reaction (Gap-LCR)," 1995, Nucl. Acids Res., 23:675-682.

Altschul, S. et al., "Basic local alignment search tool," 1990, J. Mol. Biol., 215(3):403-10.

Altschul, S. et al., "Gapped BLAST and PSI-BLAST: a new generation of protein database search programs," 1997, Nucleic Acids Res., 25:3389-3402.

Bacheler, L. et al., "Human immunodeficiency virus type 1 mutations selected in patients failing efavirenz combination therapy," 2000, Antimicrob. Agents Chemother., 44:2475-2484.

(Continued)

*Primary Examiner* — Louise Humphrey

(74) *Attorney, Agent, or Firm* — Kilpatrick Townsend & Stockton, LLP

(57) ABSTRACT

This invention relates, in part, to methods and compositions for determining altered susceptibility of a human immunodeficiency virus ("HIV") to the non-nucleoside reverse transcriptase inhibitors ("NNRTIs") efavirenz ("EFV"), nevirapine ("NVP"), and delavirdine ("DLV"), the nucleoside reverse transcriptase inhibitor AZT, and the integrase strand transfer inhibitors diketo acid 1, diketo acid 2, and L-870,810 by detecting the presence of a mutation or combinations of mutations in the gene encoding HIV reverse transcriptase that are associated with altered susceptibility to the anti-HIV drugs.

11 Claims, 22 Drawing Sheets

(56) References Cited

OTHER PUBLICATIONS

Figure 1:
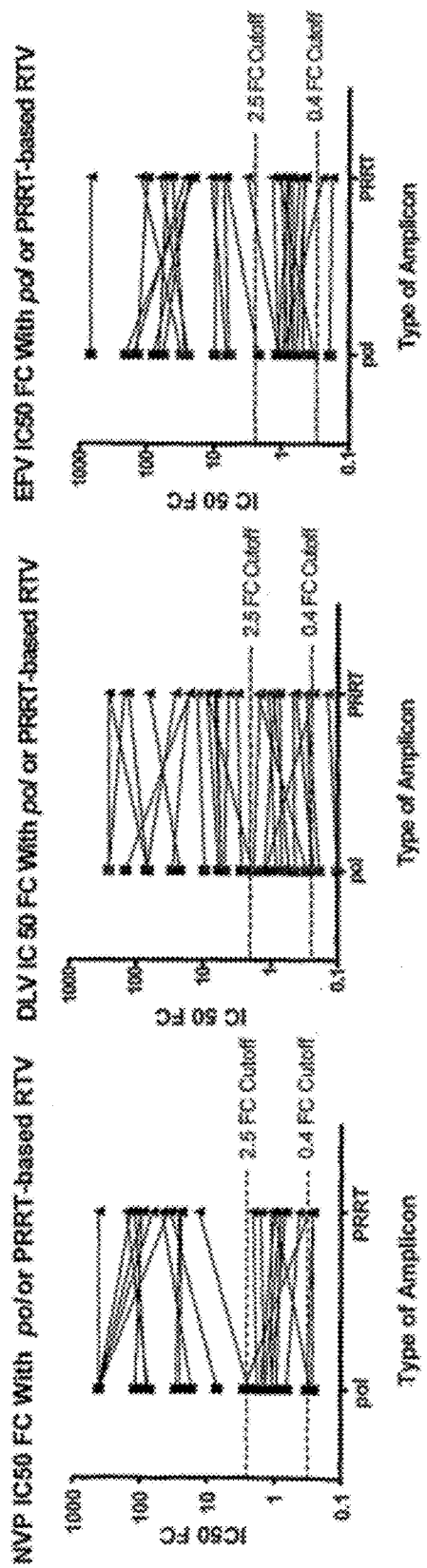

Barnes, W.M., "PCR amplification of up to 35-kb DNA with high fidelity and high yield from lambda bacteriophage templates," 1994, Proc. Natl. Acad. Sci. USA, 91:2216-2220.
Barany, F., "Genetic disease detection and DNA amplification using cloned thermostable ligase," 1991, Proc. Natl. Acad. Sci. USA, 88:189-193.
Barreca, M. et al., "Molecular dynamics studies of the wild-type and double mutant HIV-1 integrase complexed with the 5CITEP inhibitor: mechanism for inhibition and drug resistance," 2003, Biophys. J., 84:1450-1463.
Cotton, R. et al., "Reactivity of cytosine and thymine in single-base-pair mismatches with hydroxylamine and osmium tetroxide and its application to the study of mutations," 1988, Proc. Natl. Acad. Sci. USA, 85:4397-4401.
Current Protocols in Molecular Biology, Ausubel, F.M. et al, eds., John Wiley and Sons, Inc., USA, 2010 Table of Contents and list of yearly supplements.
De Clercq, E., "Development of resistance of human immunodeficiency virus (HIV) to anti-HIV agents: how to prevent the problem?," 1997, Intl. J. Antimicrobial Agents, 9:21-36.
Eisenberg, D. et al. "Analysis of membrane and surface protein sequences with the hydrophobic moment plot," 1984, J. Mol. Biol., 179:125-142.
Faham, M. and Cox, D., "A novel in vivo method to detect DNA sequence variation," 1995, Genome Res., 5:474-482.
Fisher, S.G. and Lerman, L.S., "DNA fragments differing by single base-pair substitutions are separated in denaturing gradient gels: correspondence with melting theory," 1983, Proc. Natl. Acad. Sci. USA, 80:1579-1583.
Freedman, D. et al., 1980, Statistics, W.W. Norton, New York, NY.
GenBank Accession No. AF324493, HIV-1 vector pNL4-3, complete sequence, 1986, submitted to GenBank Feb. 15, 2001.
Gervaix, A. et al., "A new reporter cell line to monitor HIV infection and drug susceptibility in vitro," 1997, Proc. Natl. Acad. Sci. USA, 94:4653-4658.
Gurusinghe, A. et al., "Reverse transcriptase mutations in sequential HIV-1 isolates in a patient with AIDS," 1995, J. Med. Virol., 46:238-243.
Hammer, S. et al.,"A controlled trial of two nucleoside analogues plus indinavir in persons with human immunodeficiency virus infection and CD4 cell counts of 200 per cubic millimeter or less," AIDS Clinical Trials Group 320 Study Team, 1997, N. Engl. J. Med., 337:725-733.
Hazuda, D. et al., "A naphthyridine carboxamide provides evidence for discordant resistance between mechanistically identical inhibitors of HIV-1 integrase," 2004, Proc. Natl. Acad. Sci. USA, 101:11233-11238.
Hertogs, K. et al., "A rapid method for simultaneous detection of phenotypic resistance to inhibitors of protease and reverse transcriptase in recombinant human immunodeficiency virus type 1 isolates from patients treated with antiretroviral drugs," 1998, Antimicrob. Agents Chemother., 42:269-276.
Kan Y.W., and Dozy, A.M., "Antenatal diagnosis of sickle-cell anemia by D.N.A. analysis of amniotic fluid cells," 1978, Lancet, 2(8096):910-912.
Kehlenseck, S. et al., "Dihydroxythiophenes are novel potent inhibitors of human immunodeficiency virus integrase with a diketo acid-like pharmacophore," 2006, J. Virology, 80:6883-6894.
Landegren, U. et al., "A ligase-mediated gene detection technique," 1988, Science, 241:1077.
Lee, M. et al., "Large-scale conformational dynamics of the HIV-1 integrase core domain and its catalytic loop mutants," 2005, Biophysical J., 88:3133-3146.
Lin, P. et al., "Genotypic and phenotypic analysis of human immunodeficiency virus type 1 isolates from patients on prolonged stavudine therapy," 1994, J. Infect. Dis., 170:1157-1164.
Lu, J. et al., "A novel recombinant marker virus assay for comparing the relative fitness of HIV-1 reverse transcriptase mutants," 2001, JAIDS, 27:7-13.
Lucas, S., "The pathology of HIV infection," 2002, Lepr. Rev., 73:64-71.
Maxam, A.M. and Gilbert,W. et al., "Sequencing end-labeled DNA with base-specific chemical cleavages," 1980, Methods in Enzymology, 65:499-560.
Messing, J., et al., "A system for shotgun DNA sequencing," 1981, Nucl. Acids Res., 9:309-321.
Myers, R. et al., "Detection of single base substitutions by ribonuclease cleavage at mismatches in RNA:DNA duplexes,", 1985, Science, 230:1242-1246.
Nikiforov, T. et al., "Genetic bit analysis: a solid phase method for typing single nucleotide polymorphisms," 1994, Nucl. Acids Res., 22:4167-4175.
Norris, T.G., "HIV update," 2002, Radiol. Technol., 73(4):339-363.
Orita, M. et al., "Rapid and sensitive detection of point mutations and DNA polymorphisms using the polymerase chain reaction," 1989, Genomics, 5:874-879.
Orita, M. et al., "Detection of polymorphisms of human DNA by gel electrophoresis as single-strand conformation polymorphisms," 1989, Proc. Natl. Acad. Sci. USA, 86:2766-2770.
Orum, H. et al., "Single base pair mutation analysis by PNA directed PCR clamping," 1993, Nucl. Acids Res., 21:5332-5336.
PCR Strategies, 1995, Innis, M.A. et al. eds., Academic Press, Inc., San Diego, CA.
Pelemans, H. et al., "A proline-to-histidine substitution at position 225 of human immunodeficiency virus type 1 (HIV-1) reverse transcriptase (RT) sensitizes HIV-1 RT to BHAP U-90152," 1998, J. General Virology, 79:1347-1352.
Petropoulos, C. et al., "A novel phenotypic drug susceptibility assay for human immunodeficiency virus type 1," 2000, Antimicrob. Agents Chemother., 44:920-928.
Race, E. et al., "Analysis of HIV cross-resistance to protease inhibitors using a rapid single-cycle recombinant virus assay for patients failing on combination therapies," 1999, AIDS, 13:2061-2068.
Rousseau, M.N. et al., "Patterns of resistance mutations to antiretroviral drugs in extensively treated HIV-1-infected patients with failure of highly active antiretroviral therapy," 2001, J. Acquir. Immune Defic. Syndr., 26:36-43.
Russell, W. et al., "Specific-locus test shows ethylnitrosourea to be the most potent mutagen in the mouse," 1979; Proc. Nat. Acad. Sci. USA, 76:5818-5819.
Russell, W., Factors Affecting Mutagenicity of Ethylnitrosourea in the Mouse Specific-Locus Test and Their Bearing on Risk Estimation, in Environmental Mutagens and Carcinogens: Proceedings of the Third International Conference on Environmental Mutagens, Tokyo, Mishima and Kyoto, 1982.
Sambrook, J. and Russell, D.W., Molecular Cloning: A Laboratory Manual, 2001, 3rd ed., Cold Spring Harbor Laboratory, New York, NY.
Sanger, F. et al., "DNA sequencing with chain-terminating inhibitors," 1977, Proc. Natl. Acad. Sci. USA, 74:5463-5467.
Sarkar, G. and Sommer, S.S., "The "megaprimer" method of site-directed mutagenesis," 1990, Biotechniques, 8:404-407.
Shi, C. and Mellors, J., "A recombinant retroviral system for rapid in vivo analysis of human immunodeficiency virus type 1 susceptibility to reverse transcriptase inhibitors," 1997, Antimicrob Agents Chemother., 41:2781-2785.
Southern, E.M., "Detection of specific sequences among DNA fragments separated by gel electrophoresis," 1975, J. Mol. Biol., 98:503-517.
Syvanen, A.C. et al., "A primer-guided nucleotide incorporation assay in the genotyping of apolipoprotein E," 1990, Genomics, 8:684-692.
Thiede, C. et al., "Simple and sensitive detection of mutations in the ras proto-oncogenes using PNA-mediated PCR clamping," 1996, Nucl. Acids Res., 24:983-984.
Vandamme, A. et al., "Characterization of HIV-1 strains isolated from patients treated with TIBO R82913," 1994, AIDS Res. Hum. Retroviruses, 10:39-46.
Wagner, R. et al., "Mutation detection using immobilized mismatch binding protein (MutS)," 1995, Nucl. Acids Res., 23:3944-3948.

(56) References Cited

OTHER PUBLICATIONS

Whitcomb, J. at al., "Broad Nucleoside Reverse-Transcriptase Inhibitor Cross-Resistance in Human Immunodeficiency Virus Type 1 Clinical Isolates," 2003, J. Infectious Disease, 188:992-1000.

Youil, R. et al., "Screening for mutations by enzyme mismatch cleavage with T4 endonuclease VII," 1995, Proc. Natl. Acad. Sci USA, 92:87-91.

International Search Report mailed Feb. 5, 2007 corresponding to Application No. PCT/US06/22072.

Written Opinion of the International Searching Authority mailed Feb. 5, 2007 corresponding to Application No. PCT/US06/22072.

Colonno, R. et al., "Identification of I50L as the Signature Atazanavir (ATV)-Resistance Mutation in Treatment-Naïve HIV-1-Infected Patients Receiving ATV-Containing Regimens," 2004, J. Infectious Diseases, 189:1802-1810.

Gupta, S. et al., "Combinations of Mutations in the Connection Domain of Human Immunodeficiency Virus Type 1 Reverse Transcriptase: Assessing the Impact on Nucleoside and Non-nucleoside Reverse Transcriptase Inhibitor Resistance," 2010, Antimicro. Agents Chemother., 54:1973-1980.

Hirsch, M. et al., "Antiretroviral Drug Resistance Testing in Adult HIV-1 Infection: 2008 Recommendations of an International AIDS Society-USA Panel," 2008, Clinical Infectious Diseases, 47:266-285.

Mellors, J. et al., "Mutations in HIV-1 Reverse Transcriptase and Protease Associated with Drug Resistance," 1995, Mutations in RT and Protease, III:93-105.

Kroodsma et al. Detection of Drug Resistance Mutations in the Human Immunodeficiency Virus Type 1 (HIV-1) pot Gene: Differences in Semen and Blood HIV-1 RNA and Proviral DNA. The Journal of Infectious Diseases 1994, vol. 170, p. 1292-1295.

\* cited by examiner

Diagrammatic Representations of Constructs
for Different Amplicons of Sample 62

NVP Susceptibility Results for a T369I Site Directed Mutant

Fig. 7

| RATIO OF POL/PR-RT IC50 FC for NNRTIs | | | | |
|---|---|---|---|---|
| | DLV | EFV | NVP | |
| Total # of comparisons | 52 | 52 | 51 | |
| # > 2 fold | 12 (23%) | 17 (32.7%) | 18 (35.3%) | |
| # > 5 fold | 2 (3.8%) | 1 (1.9%) | 5 (9.8%) | |
| # > 10 fold | 0 | 1 (1.9%) | 1 (1.9%) | |
| # Changing Susceptibility Call | 5* | 7 (6*) | 6 (5*) | |
| Cutoff Used | 2.5 | 2.5 | 2.5 | |

Fig. 12

| RATIO OF POL/PRRT IC50 FC - AZT | |
|---|---|
| Total # of comparisons | 52 |
| # > 2 fold | 19 (36.5%) |
| # > 5 fold | 7 (13.5%) |
| # > 10 fold | 4 (7.8%) |
| # Changing Susceptibility Call | 0 |
| Cutoff Used | 1.9 |

Fig. 20

| | RC | DKA #1 FOLD CHANGE | DKA#2 FOLD CHANGE | L-870,810 FOLD CHANGE |
|---|---|---|---|---|
| NL4-3 | 120.5 | 0.94 | 1.00 | 1.00 |
| NL4-3 T97A | 31.0 | 0.68 | 0.70 | 2.73 |
| NL4-3 K156N2 | 100.2 | 1.24 | 1.12 | 0.52 |
| NL4-3 T97A_K156N | 30.1 | 1.38 | 1.20 | 1.26 |
| IIIB | 131.4 | 0.97 | 1.02 | 1.16 |
| IIIB_T97A | 18.1 | 0.77 | 0.78 | 2.97 |
| IIIB_K156N | 144.2 | 1.18 | 0.89 | 0.44 |
| IIIB_K156N_T97A | 15.1 | 1.04 | 0.87 | 1.30 |
| IIIB_V72I/F121Y/T125K (TRIPLE) | 30.9 | 2.44 | 3.40 | 35 |
| TRIPLE_T97A | 0.4 | 3.68 | 6.20 | 82 |
| TRIPLE_K156N | 6.4 | 7.20 | 10 | 20 |
| TRIPLE_K156N_T97A | 0.5 | 9.17 | 22 | 64 |
| IIIB_N155S | 20.3 | 8.33 | 9.75 | 16 |
| IIIB_N155S_T97A | 12.8 | 26.2 | 23 | 69 |
| IIIB_N155S_K156N | 20.9 | 21.7 | 23 | 8.96 |
| IIIB_N155S_T97A_K156N | 6.7 | 45.6 | 73 | 46 |
| IIIB_T66I/M154I | 84.2 | 1.42 | 1.43 | 1.97 |
| IIIB_T66I/M154I_T97A | 7.9 | 5.49 | 6.35 | 17 |

METHODS AND COMPOSITIONS FOR DETERMINING ALTERED SUSCEPTIBILITY OF HIV-1 TO ANTI-HIV DRUGS

PRIOR RELATED APPLICATIONS

This application is a divisional application of U.S. application Ser. No. 11/916,632 filed Dec. 5, 2007 (now U.S. Pat. No. 8,071,284), which is a §371 national phase application of PCT Application No. PCT/US06/22072 filed Jun. 6, 2006, which claims priority to U.S. provisional application No. 60/688,171 filed Jun. 6, 2005. Each of these applications is hereby incorporated by reference in its entirety.

1. FIELD OF INVENTION

This invention relates, in part, to methods and compositions for determining altered susceptibility of a human immunodeficiency virus ("HIV") to the non-nucleoside reverse transcriptase inhibitors ("NNRTIs") efavirenz ("EFV"), nevirapine ("NVP"), and delavirdine ("DLV"), the nucleoside reverse transcriptase inhibitor AZT, and the integrase strand transfer inhibitors diketo acid 1, diketo acid 2, and L-870,810 by detecting the presence of a mutation or combinations of mutations in an HIV pol gene that are associated with altered susceptibility to the anti-HIV drugs.

2. BACKGROUND OF THE INVENTION

More than 60 million people have been infected with the human immunodeficiency virus ("HIV"), the causative agent of acquired immune deficiency syndrome ("AIDS"), since the early 1980s. See Lucas, 2002, *Lepr Rev.* 73(1):64-71. HIV/AIDS is now the leading cause of death in sub-Saharan Africa, and is the fourth biggest killer worldwide. At the end of 2001, an estimated 40 million people were living with HIV globally. See Norris, 2002, *Radiol Technol.* 73(4):339-363.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors ("NRTIs") such as AZT, ddI, ddC, d4T, 3TC, and abacavir; nucleotide reverse transcriptase inhibitors such as tenofovir; non-nucleoside reverse transcriptase inhibitors ("NNRTIs") such as nevirapine, efavirenz, and delavirdine; protease inhibitors ("PIs") such as saquinavir, ritonavir, indinavir, nelfinavir, amprenavir, lopinavir and atazanavir; and fusion inhibitors, such as enfuvirtide. In addition, a number of drugs in other classes are currently under investigation for their ability to effectively treat HIV infection. Among such drugs are integrase strand transfer inhibitors ("INSTIs") such as the diketo acids diketo acid 1 and diketo acid 2 and the napthyridine carboximides L-870,810 and MK0518.

Nonetheless, in the vast majority of subjects none of these antiviral drugs, either alone or in combination, proves effective either to prevent eventual progression of chronic HIV infection to AIDS or to treat acute AIDS. This phenomenon is due, in part, to the high mutation rate of HIV and the rapid emergence of mutant HIV strains that are resistant to antiviral therapeutics upon administration of such drugs to infected individuals.

Many such mutant strains have been characterized in order to correlate presence of the mutations in the strains with resistant or susceptible phenotypes. For example, the K103N mutation in reverse transcriptase is known to correlate with resistance to a number of NNRTIs. See, e.g., De Clercq, 1997, *Intl J. of Antimicrobial Agents* 9:21-36. In addition, the P225H mutation in reverse transcriptase is also known to correlate with resistance to HIV-1 specific reverse transcriptase inhibitors (RTI). See, e.g., Pelemans et al., 1998, *J. Gen. Virol.* 79(Pt6):1347-52. Thus, a given mutation may correlate with resistance to one or more antiviral agents.

Though numerous mutations associated with resistance to particular anti-viral agents have been identified, the complete set of mutations associated with resistance to NNRTIs, to NRTIs, and to INSTIs has not been identified. Further, in view of the clinical relevance of NRTI, NNRTI, and INSTI resistance, a more complete understanding of mutations associated with such resistance is also needed. Thus, there remains a need to identify additional mutations associated with resistance to NRTIs, NNRTIs, and INSTIs and to characterize these mutations. For the first time, these, as well as other unmet needs, will be achievable as a result of the invention described hereinafter.

3. SUMMARY OF THE INVENTION

In certain aspects, the present invention provides methods for determining whether an HIV-1 is resistant to anti-HIV drugs, including an NRTI, an NNRTI, or an INSTI. In the methods, resistance to an anti-HIV drug can be determined by detecting the presence of mutations that correlate with resistance to an anti-HIV drug.

Thus, in certain aspects, the invention provides a method for determining whether an HIV-1 is resistant to an NNRTI or to AZT, comprising detecting whether a mutation at codon 348 or 369 is present in a gene encoding reverse transcriptase of the HIV-1, wherein the presence of the mutation correlates with resistance to an NNRTI or to AZT, such that if the mutation at codon 348 or 369 is present, the HIV-1 is resistant to the NNRTI. In certain embodiments, the methods comprise detecting whether a mutation at codon 348 or 369 is present in the gene encoding reverse transcriptase in combination with a mutation at codon 103, 179, 190, or 225, wherein the presence of the mutations correlates with resistance to an NRTI, such that if the mutations are present, the HIV-1 is resistant to the NNRTI. In some embodiments, the methods comprise detecting whether a mutation at codon 348 or 369 is present in combination with a mutation at codon 103. In other embodiments, the methods comprise detecting whether a mutation at codon 369 is present in combination with a mutation at codon 225. In some embodiments, the methods comprise detecting whether a mutation at codon 348 or 369 is present in combination with a mutation at codon 190. In some embodiments, the methods comprise detecting whether a mutation at codon 348 or 369 is present in combination with a mutation at codon 103 and at codon 179. In another embodiment, the methods comprise detecting whether a mutation at codon 369 is present in combination with a mutation at codon 103 and a mutation at codon 225, wherein the presence of the mutations correlates with resistance to an NNRTI, such that if the mutations are present, the HIV-1 is resistant to the NNRTI.

In yet other embodiments, the method comprises detecting whether a mutation at codon 399 in combination with a mutation at codon 103, 179, or 190 is present in a gene encoding reverse transcriptase of the HIV-1, wherein the presence of the mutations correlates with resistance to an NNRTI, such that if the mutation is present, the HIV-1 is resistant to the NNRTI. In some embodiments, the methods comprise detecting whether a mutation at codon 399 is present in combination with a mutation at codon 190. In some embodiments, In some embodiments, the methods comprise detecting whether a mutation at codon 399 is present in combination with a mutation at codon 103. In some embodiments, In some embodiments, the methods comprise detecting whether a mutation at codon 399 is present in combination with a mutation at codon 103 and at codon 179.

In another aspect, the invention provides a method for determining whether an HIV-1 has reduced replication capacity relative to a reference HIV-1, comprising detecting, in a nucleic acid encoding reverse transcriptase of the HIV-1, a mutation at codon 369 or in a nucleic acid encoding integrase of the HIV-1, a mutation at codon 97, wherein the presence of the mutation correlates with reduced replication capacity such that if the mutation is present, the HIV-1 has reduced replication capacity relative to a reference HIV-1. In certain embodiments, a mutation at codon 369 of reverse transcriptase is detected. In certain embodiments, a mutation at codon 97 of integrase is detected.

In still another aspect, the invention provides a method for determining whether a human immunodeficiency virus 1 (HIV-1) has altered susceptibility to a integrase strand transfer inhibitor (INSTI), comprising detecting whether a mutation at codon 97 or codon 156 is present in a gene encoding integrase of the HIV-1, wherein the presence of the mutations correlates with altered susceptibility to an INSTI, such that if the mutation is present, the HIV-1 is resistant to the INSTI. In certain embodiments, a mutation at codon 97 is detected. In certain embodiments, a mutation at codon 156 is detected. In certain embodiments, the HIV-1 exhibits increased susceptibility to the INSTI. In certain embodiments, the HIV-1 exhibits decreased susceptibility to the INSTI.

In certain embodiments, the method further comprises detecting whether a mutation at codon 66, 72, 121, 125, 154, or 155 is present in the gene encoding integrase. In certain embodiments, a mutation at codon 66 is detected. In certain embodiments, a mutation at codon 72 is detected. In certain embodiments, a mutation at codon 121 is detected. In certain embodiments, a mutation at codon 125 is detected. In certain embodiments, a mutation at codon 154 is detected. In certain embodiments, a mutation at codon 155 is detected. In certain embodiments, mutations at codons 72, 121, and 125 are detected. In certain embodiments, mutations at codons 66 and 154 are detected.

The presence of the mutations associated with resistance to AZT, to an NNRTI, or to an INSTI can be detected according to any method known to one of skill in the art without limitation. Methods for detecting such mutations are described extensively below.

4. BRIEF DESCRIPTION OF THE FIGURES

FIG. 1 illustrates that there are no statistical differences in NNRTI $IC_{50}$ fold change values obtained in phenotypic assays using resistance test vectors comprising POL and RHIN sequences. Resistance assays were performed using different resistance test vectors comprising different patient-derived segments (POL and PR-RT) from the same HIV-infected patient samples to assess relative contributions of the segments to resistance to NNRTIs (NVP, DLV and EFV) of HIV isolated from HIV-infected patients. Results (fold change in IC50 or "FC") for each of these different amplicons prepared from the same patient samples were compared.

Figure 2:
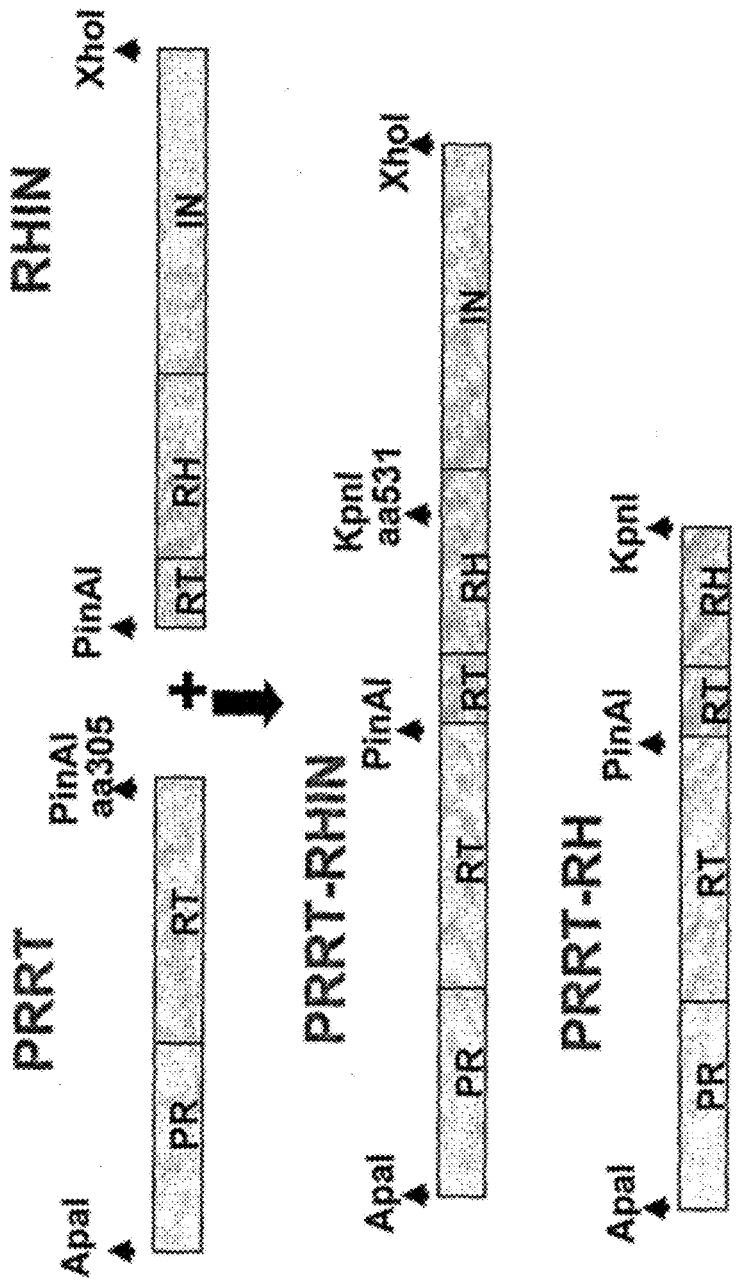
Figure 3:
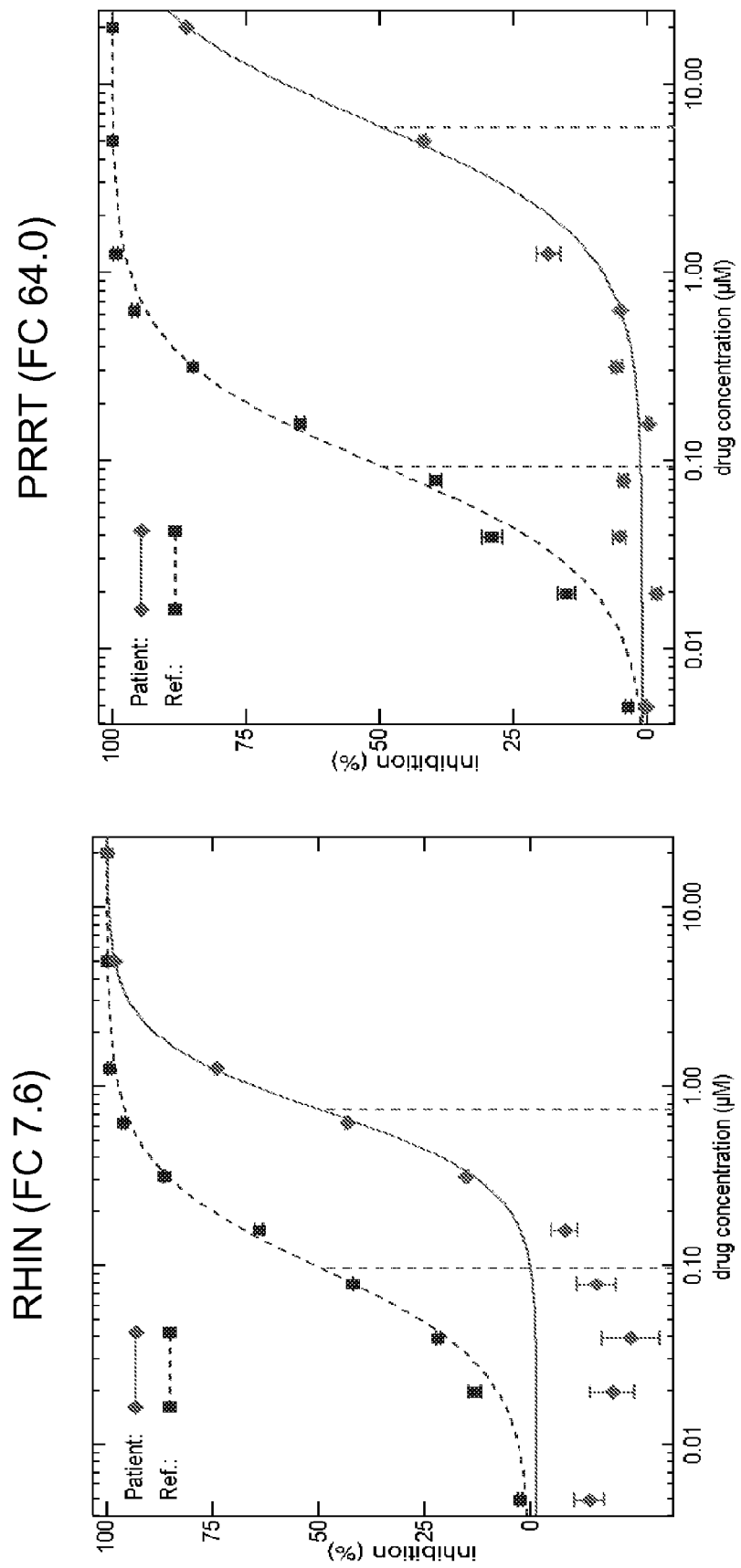
Figure 3:
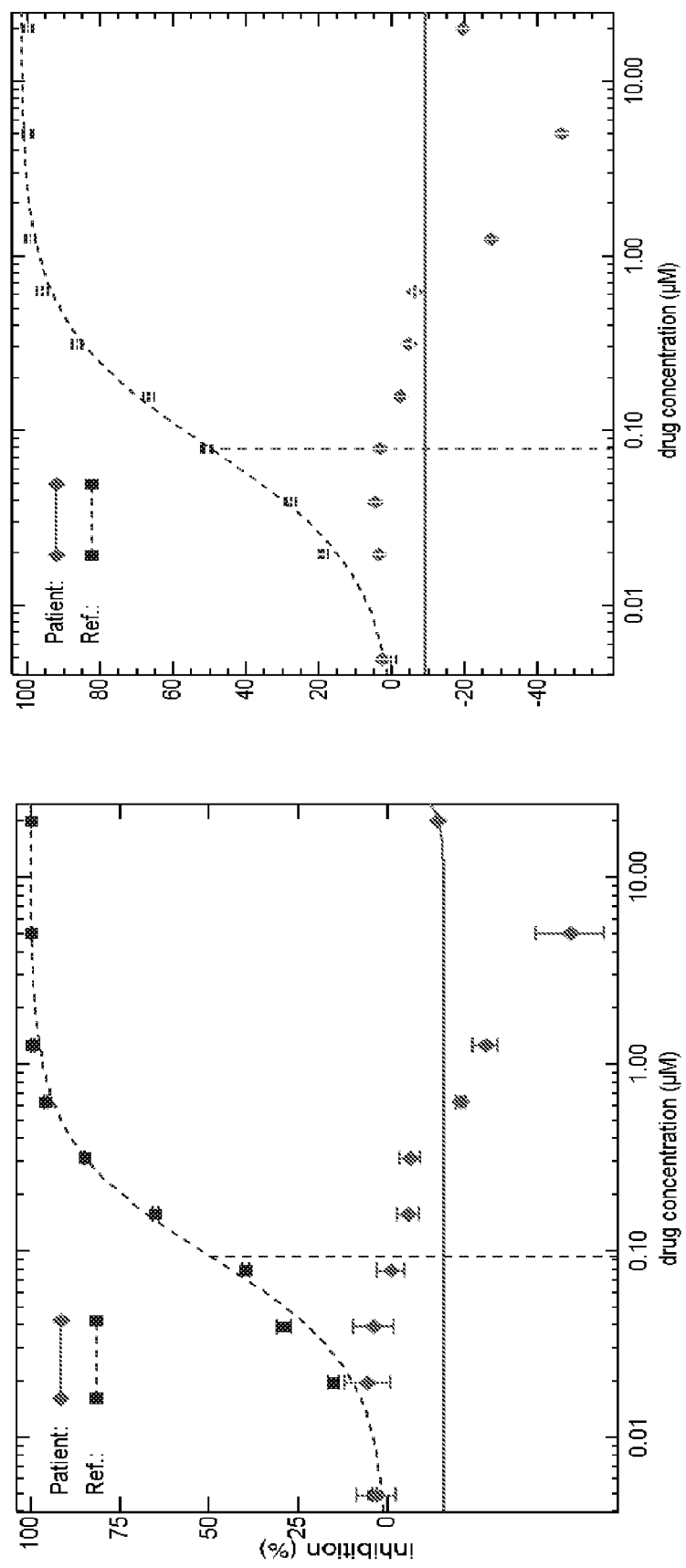
Figure 3:
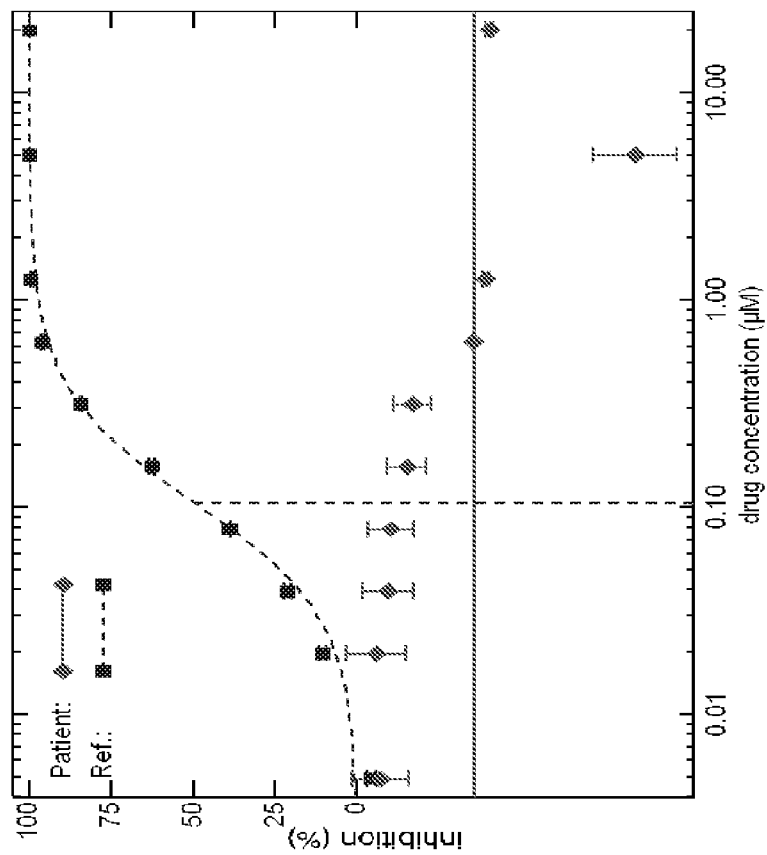

FIG. 2 provides a diagrammatic representation of constructs for different amplicons of sample 62 tested in FIG. 3. The POL amplicon comprises a patient-derived segment corresponding to the entire poi gene, encoding HIV protease, reverse transcriptase (including RNase H), and integrase. The PR-RT amplicon comprises a patient-derived segment corresponding to the portion of pol encoding HIV protease and amino acids 1-305 of reverse transcriptase. The RHIN amplicon comprises a patient-derived segment corresponding to the portion of pol encoding amino acids 319-440 of reverse transcriptase (including RNase H), and integrase. The PRRT-RH amplicon comprises a patient-derived segment corresponding to the portion of pol encoding protease and amino acids 1-531 of reverse transcriptase (including RNase H). The PRRT-RHIN amplicon comprises a patient-derived segment corresponding to the portion of pol encoding protease, reverse transcriptase (including RNase H) and integrase.

FIG. 3 shows that different amplicons and constructs derived from a patient sample exhibit different degrees of NVP resistance.

Figure 4:
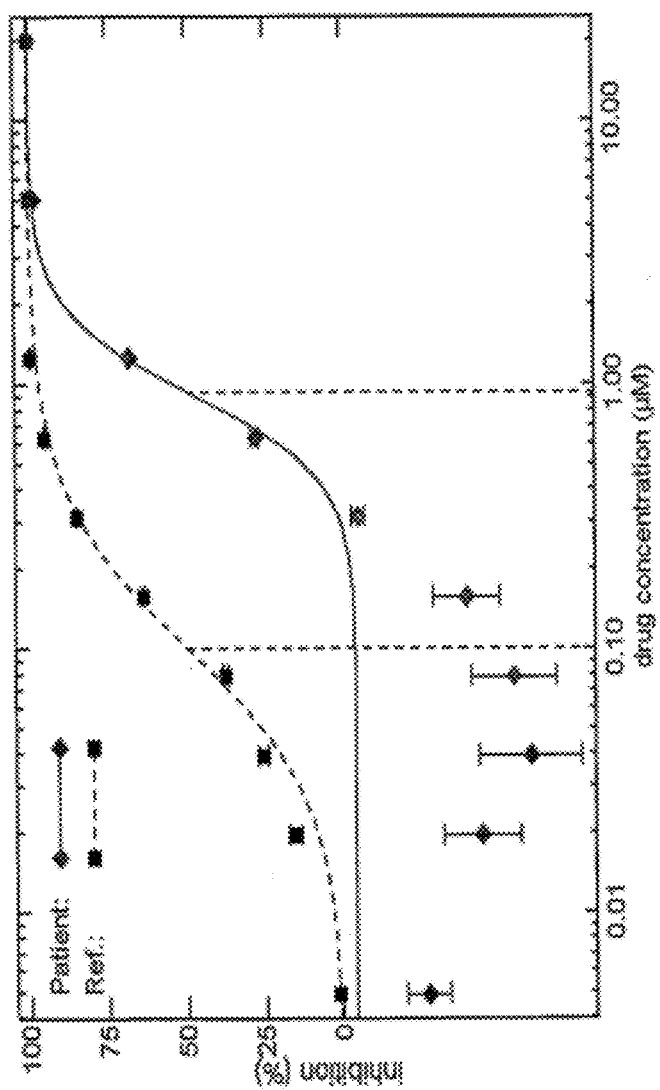

FIG. 4 presents the fold change in IC50 observed in the presence of NVP for an HIV-1 site-directed mutant that comprises the T369I mutation in reverse transcriptase in a NL4-3 background.

Figure 5:
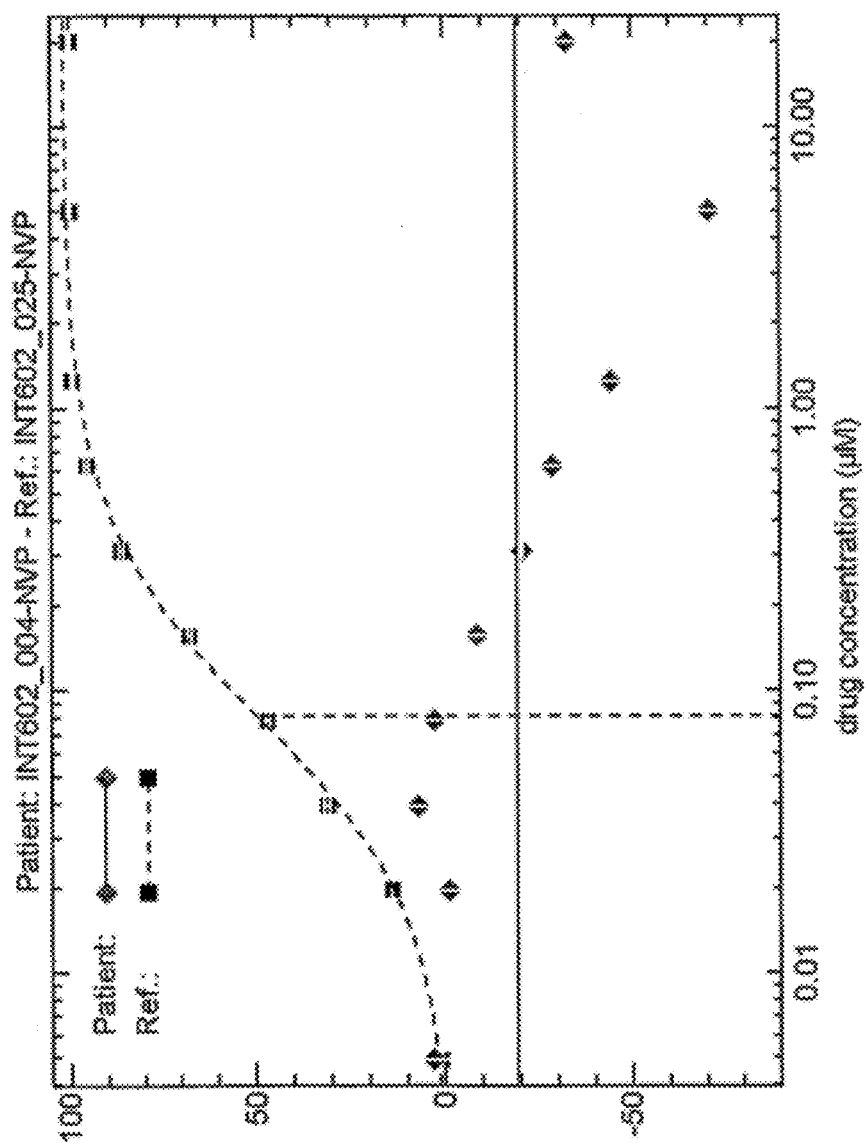

FIG. 5 presents the fold change in IC50 observed in the presence of NVP for an HIV-1 site-directed mutant that comprises the T369I mutation and the K103N mutation in reverse transcriptase in a NL4-3 background.

Figure 6:
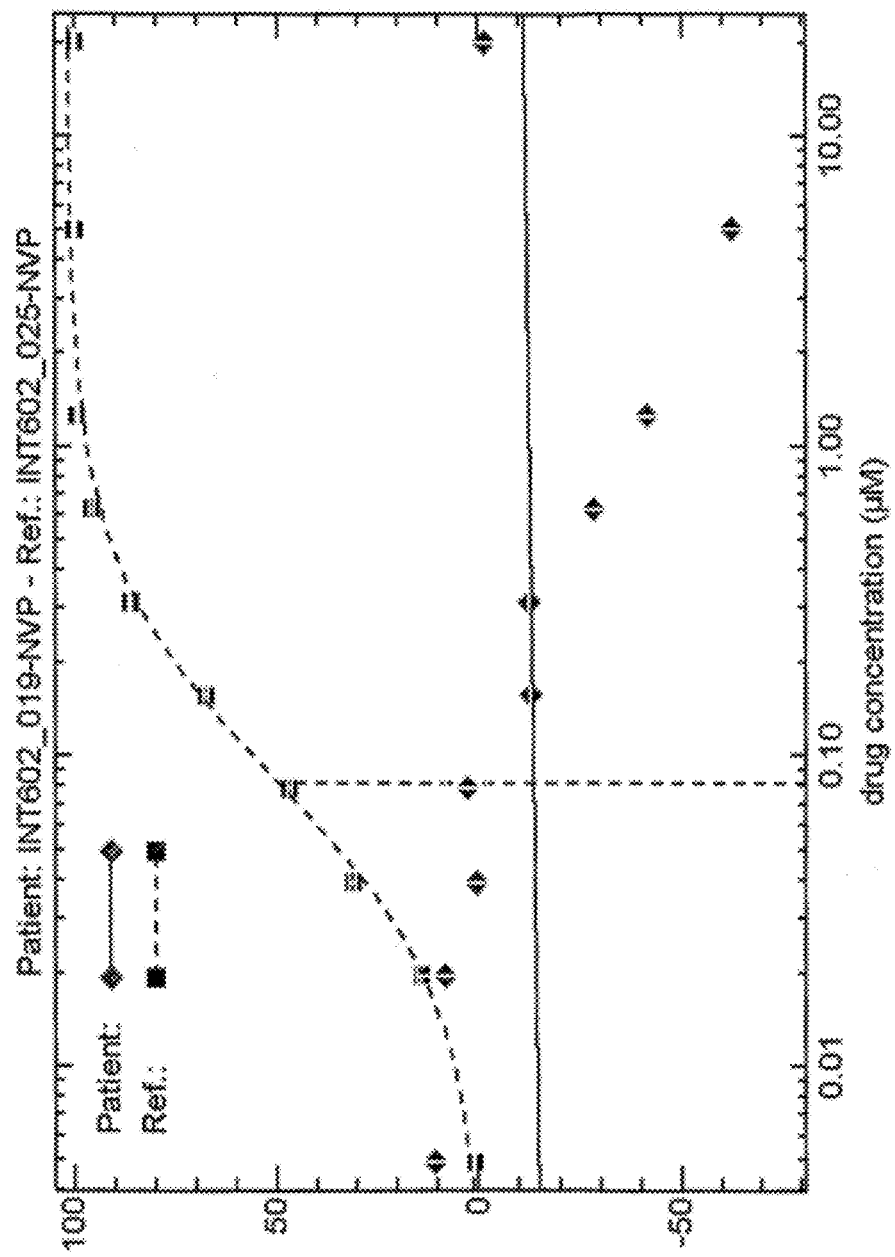

FIG. 6 presents the fold change in IC50 observed in the presence of NVP for the PRRT patient-derived segment obtained from sample 62 and also comprising T369I site-directed mutation.

FIG. 7 presents comparisons between the fold change in NNRTI resistance observed for the PR-RT patient segment and the POL patient segment for 52 patient samples.

Figure 8:
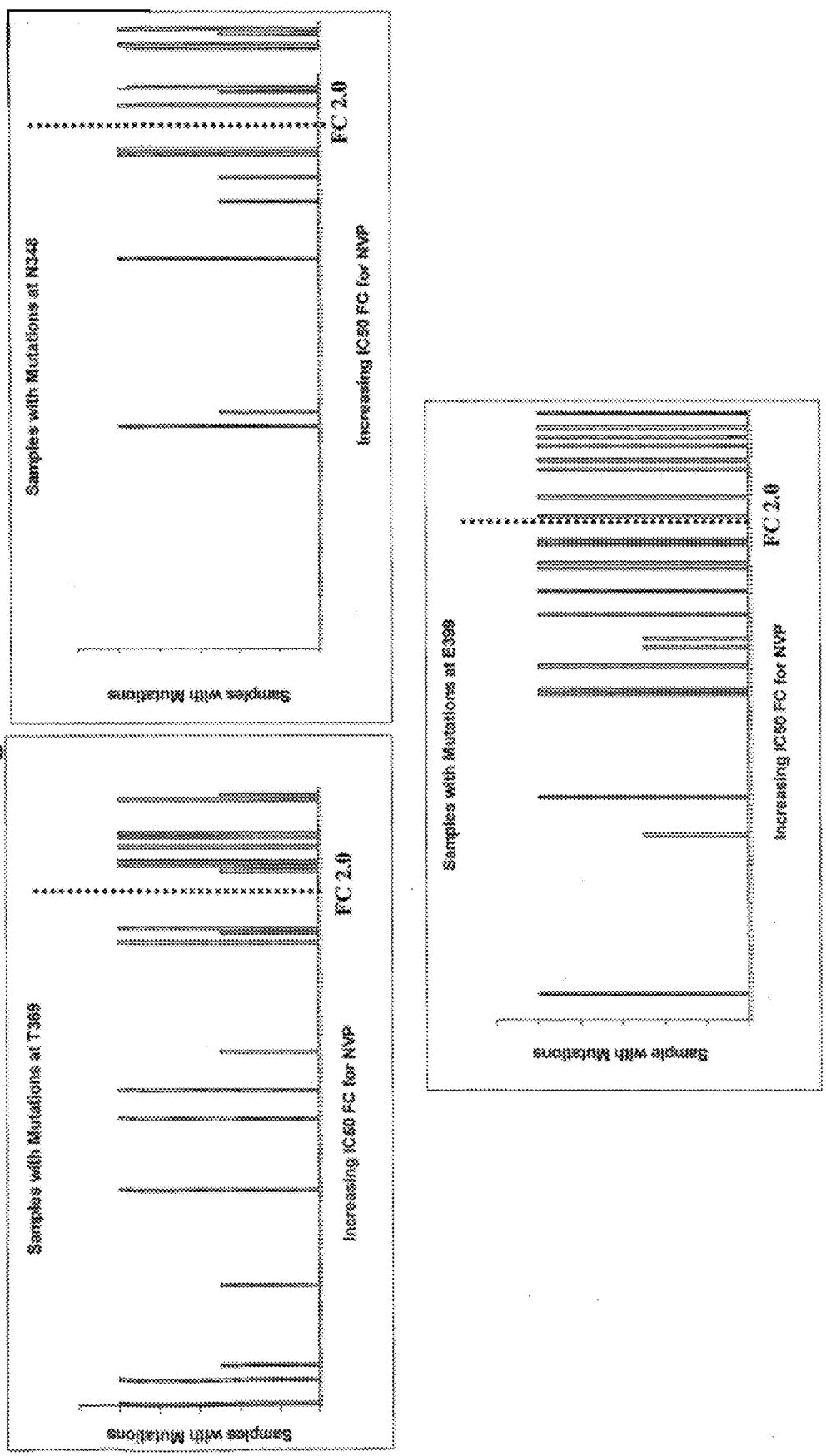

FIG. 8 presents the distribution of fold change in NNRTI resistance for patient samples having mutations at RT positions 348, 369, and 399.

Figure 9:
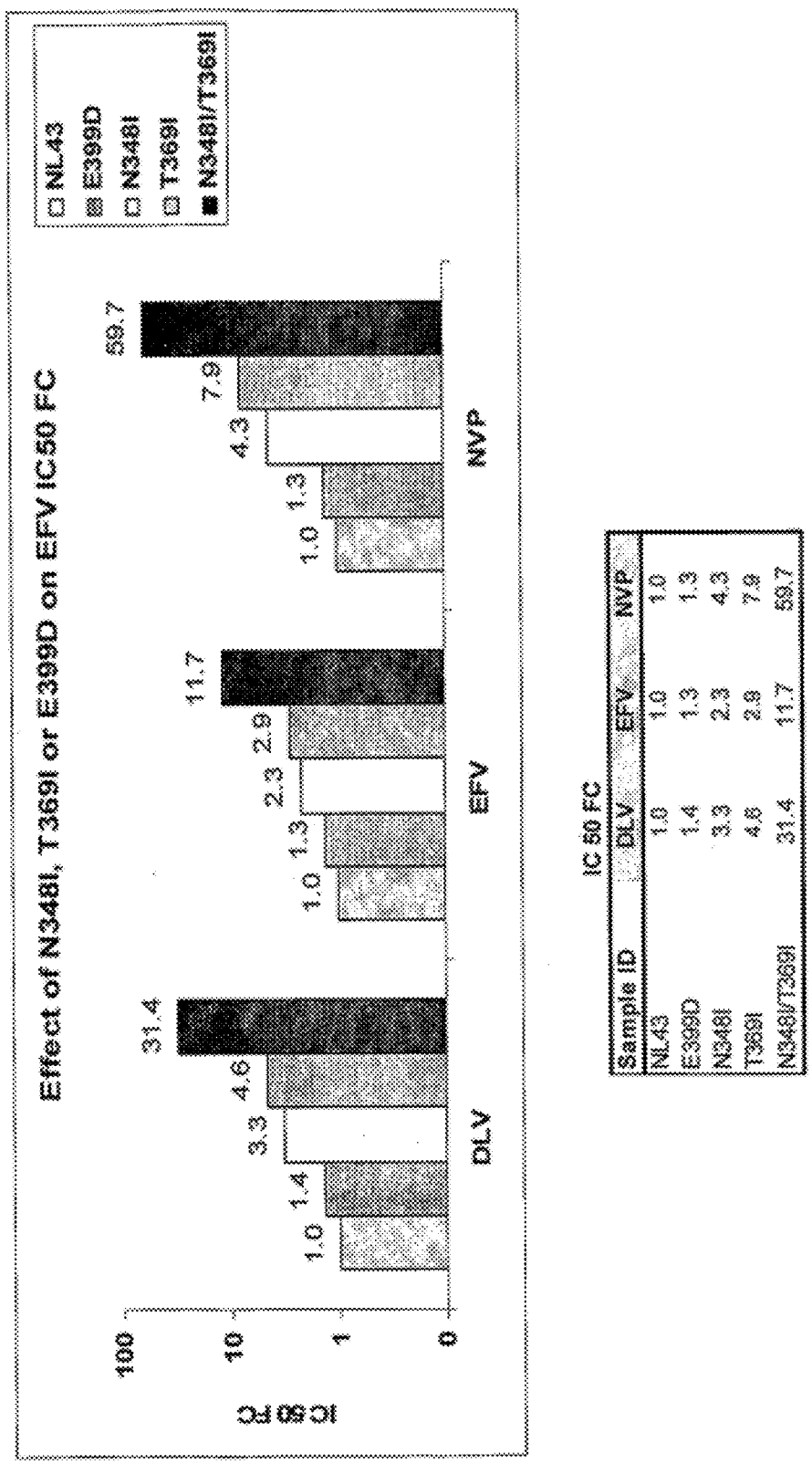

FIG. 9 presents the results of phenotypic assays showing resistance or susceptibility to NNRTIs on site-directed mutants having mutations at RT positions 348, 369, and 399 in an NL4-3 background.

Figure 10:
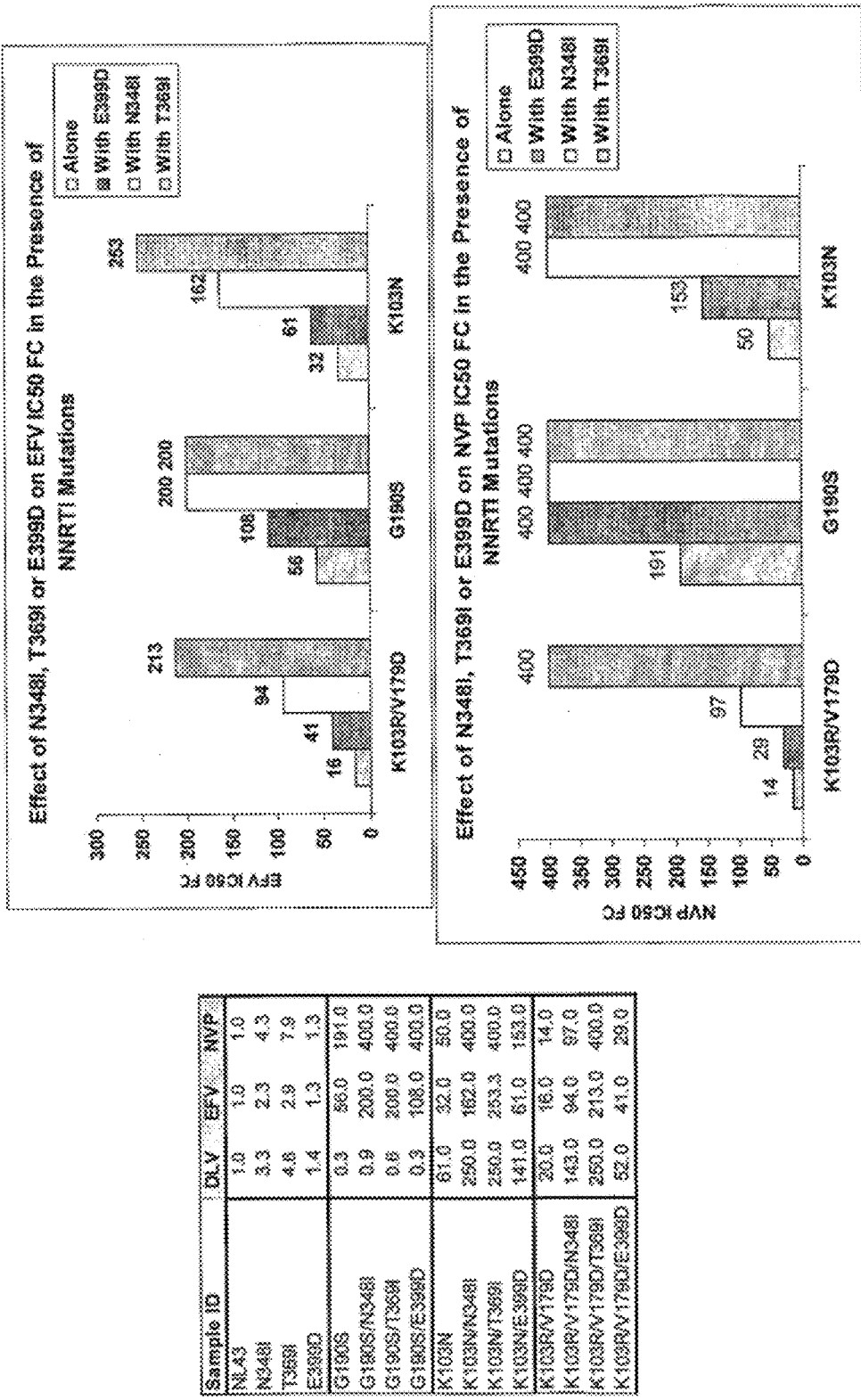

FIG. 10 presents the results of phenotypic assays showing resistance or susceptibility to NNRTIs on site-directed mutants having mutations at RT positions 348, 369, and 399 in combination with previously identified NNRTI resistance mutations in an NL4-3 background.

Figure 11:
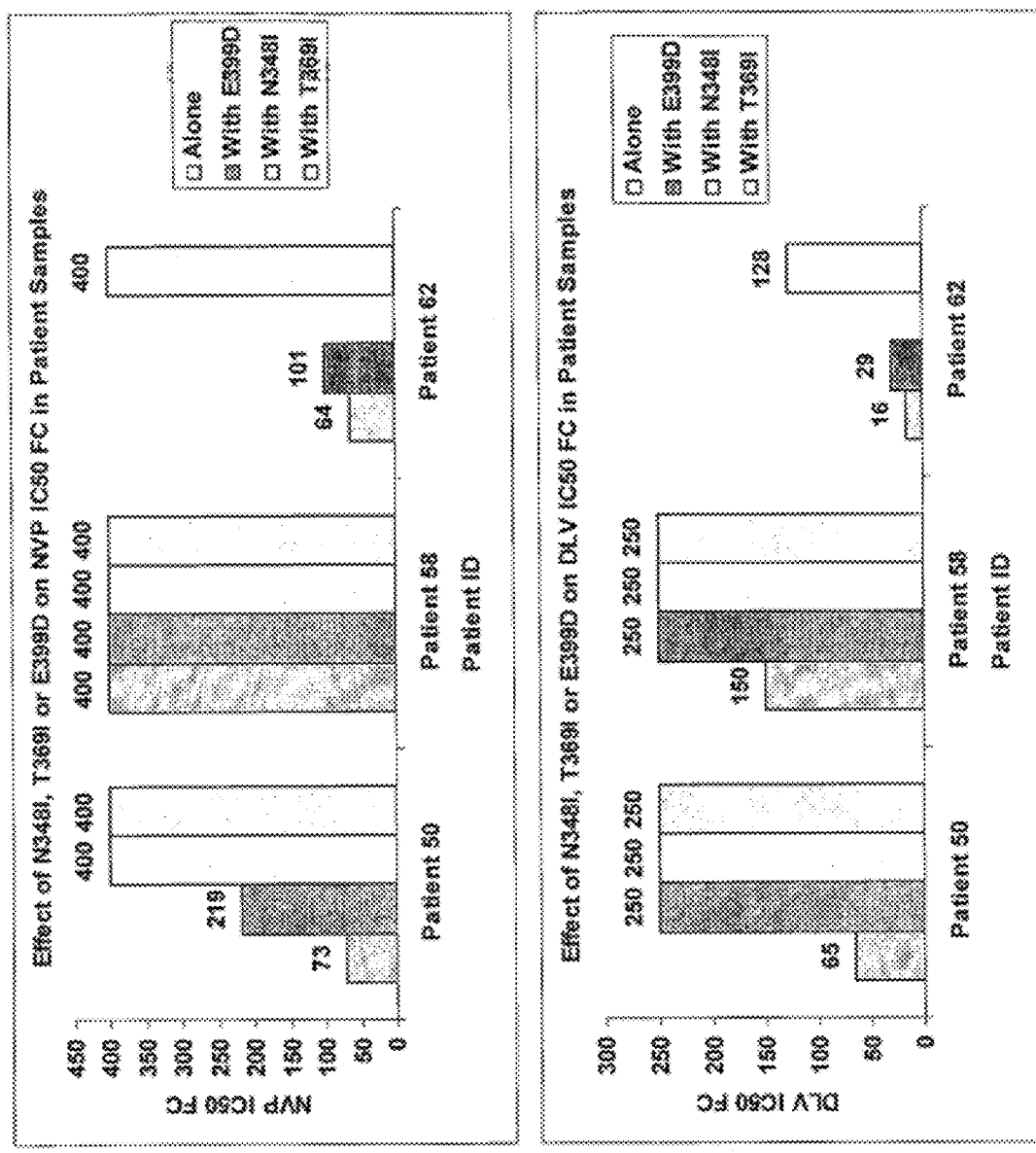

FIG. 11 presents the results of phenotypic assays showing resistance or susceptibility to NNRTIs on site-directed mutants having mutations at RT positions 348, 369, and 399 in three different patient backgrounds.

FIG. 12 presents comparisons between the fold change in AZT resistance observed for the PR-RT patient segment and the POL patient segment for 52 patient samples.

Figure 13:
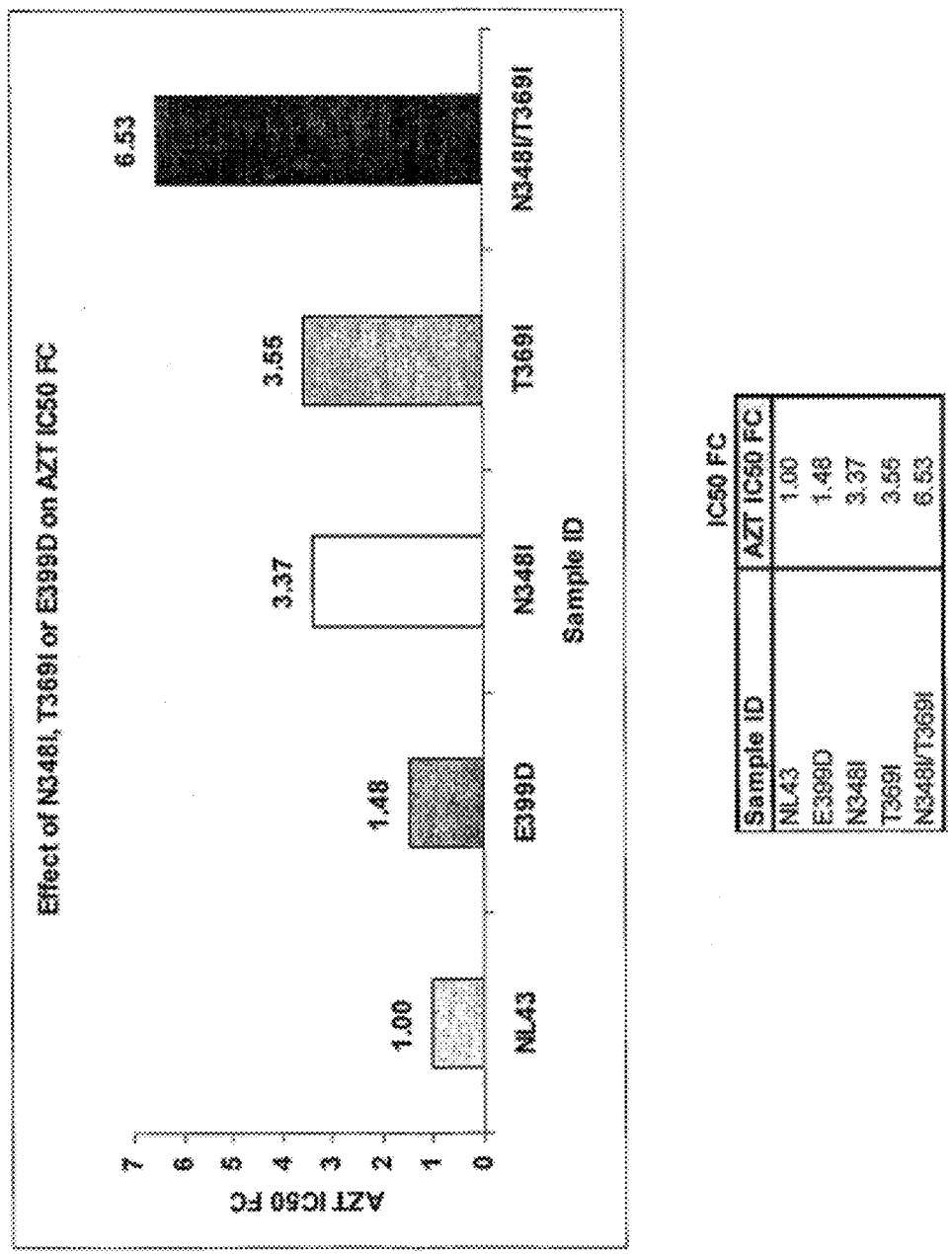

FIG. 13 presents the results of phenotypic assays showing resistance or susceptibility to AZT on site-directed mutants having mutations at RT positions 348, 369, and 399 in an NL4-3 background.

Figure 14:
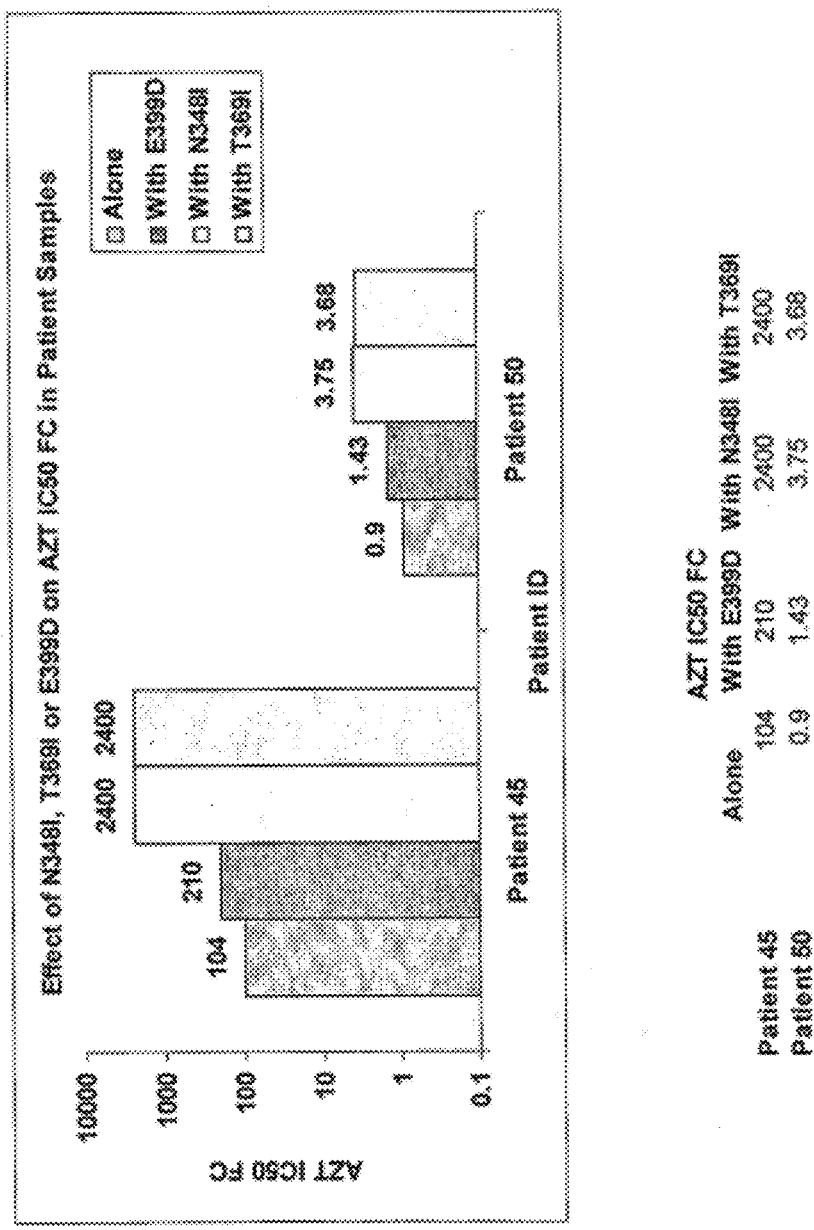

FIG. 14 presents the results of phenotypic assays showing resistance or susceptibility to AZT on site-directed mutants having mutations at RT positions 348, 369, and 399 in two different patient backgrounds.

Figure 15:
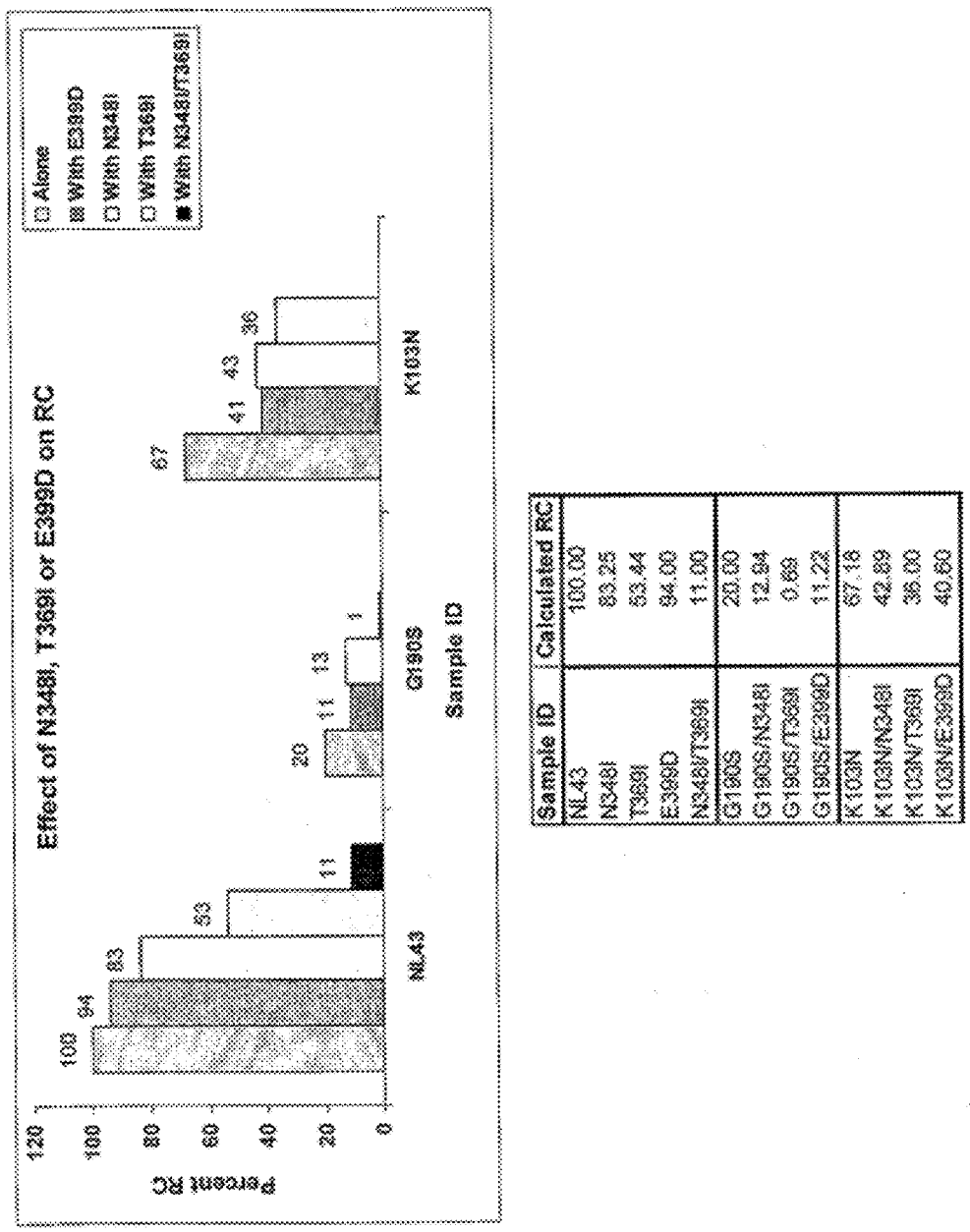

FIG. 15 presents the results of phenotypic assays showing that the RT mutation T369I causes a reduction in replication capacity in an NL4-3 background.

Figure 16:
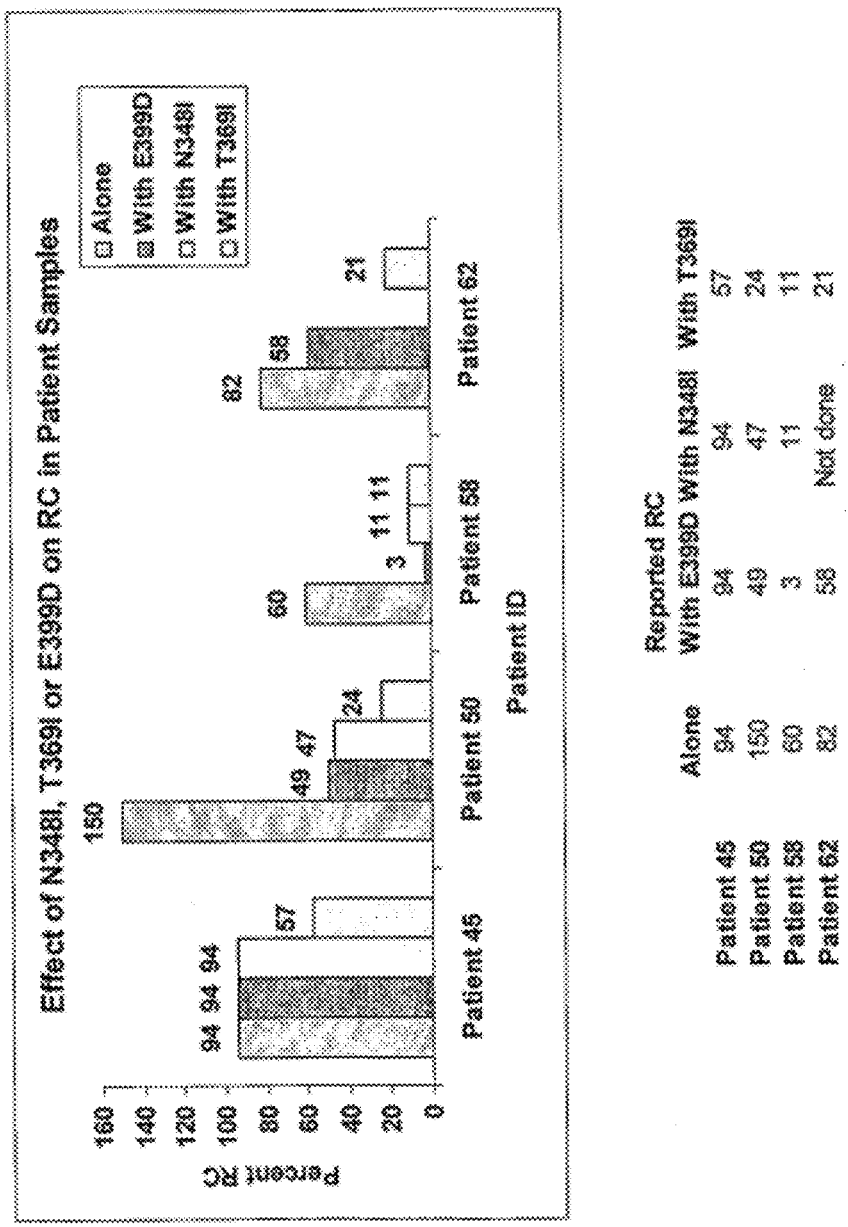

FIG. 16 presents the results of phenotypic assays showing that RT mutations in codons 348, 369, and 399 cause a reduction in replication capacity in some patient backgrounds.

Figure 17:
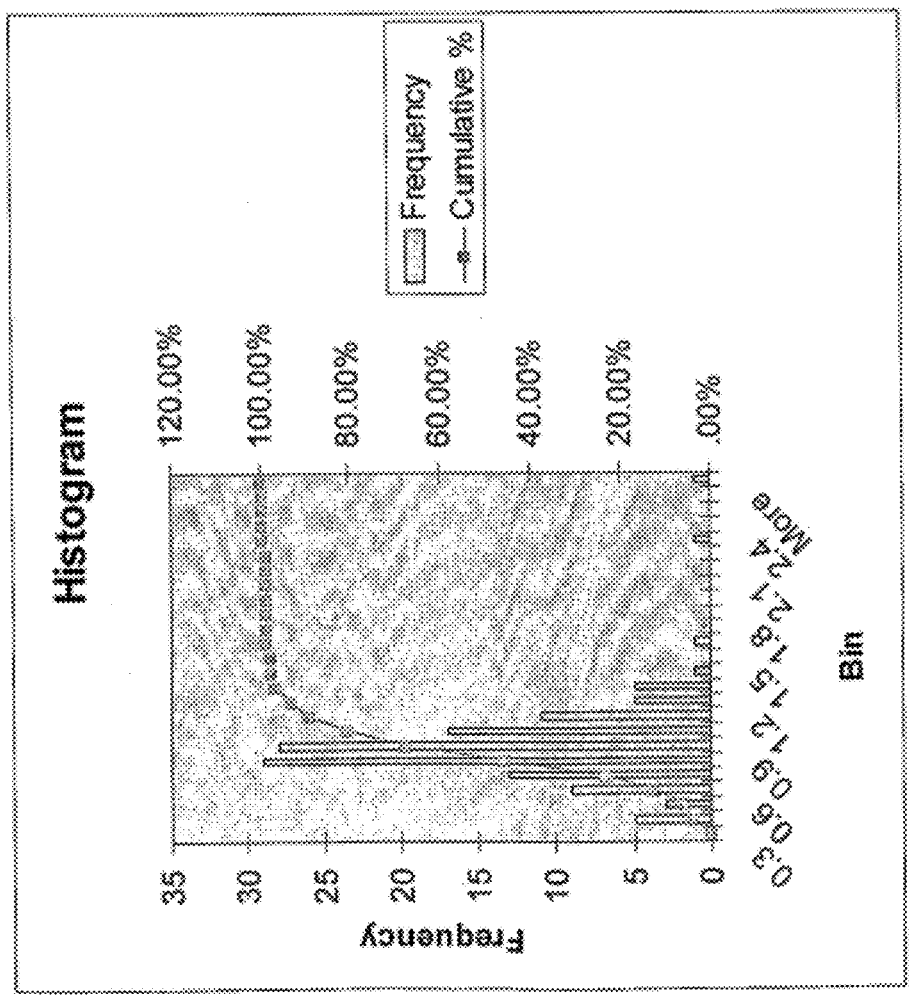

FIG. 17 presents the distribution of resistance or susceptibility in IC50 fold change to the INSTI L-870,810 in 128 patient samples.

Figure 18:
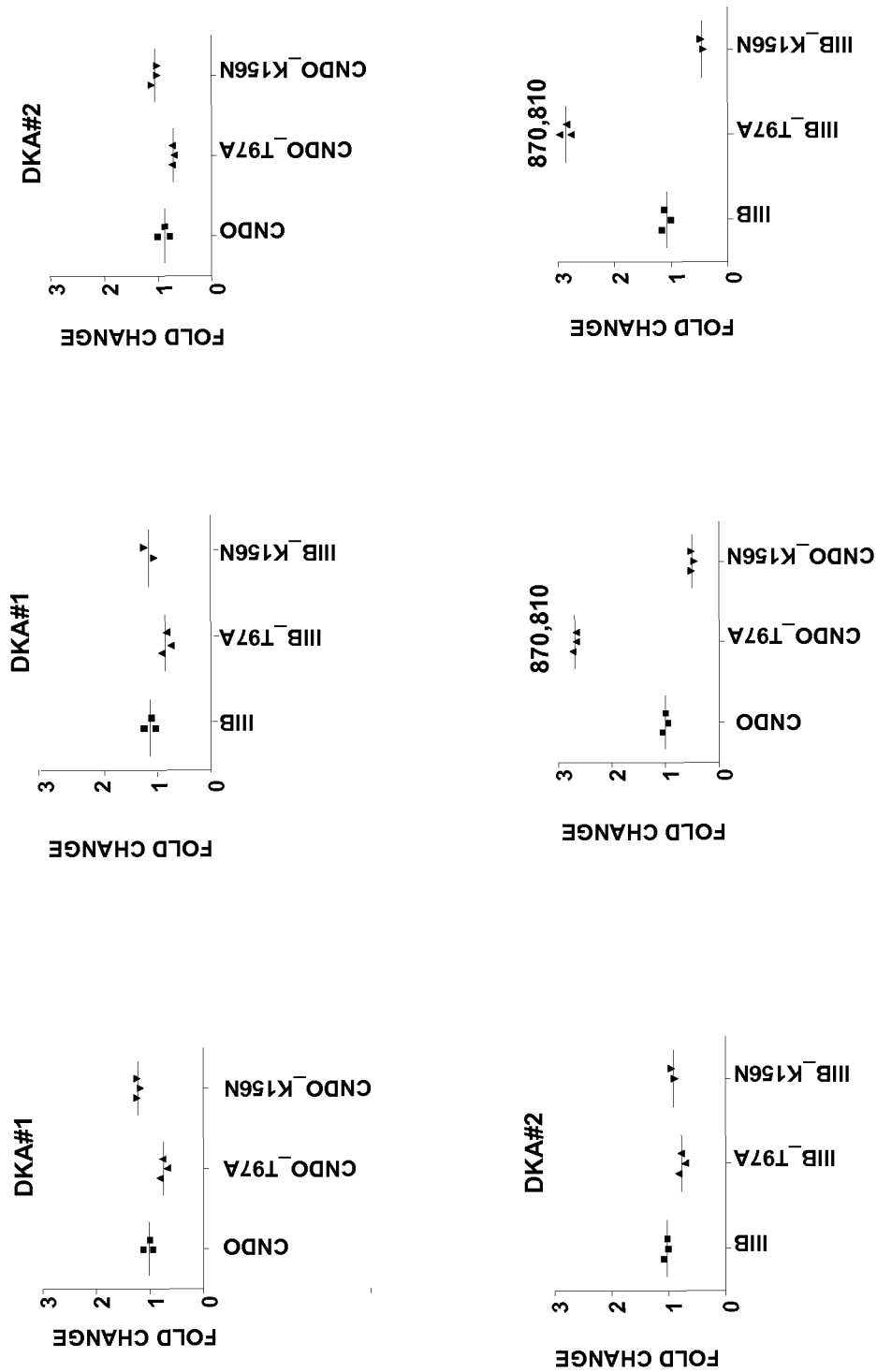

FIG. 18 presents the results of phenotypic assays showing that mutations in integrase codons 97 and 156 result in altered susceptibility to the INSTI L-870,810, but do not result in altered susceptibility to the INSTIs diketo acid 1 and diketo acid 2.

Figure 19:
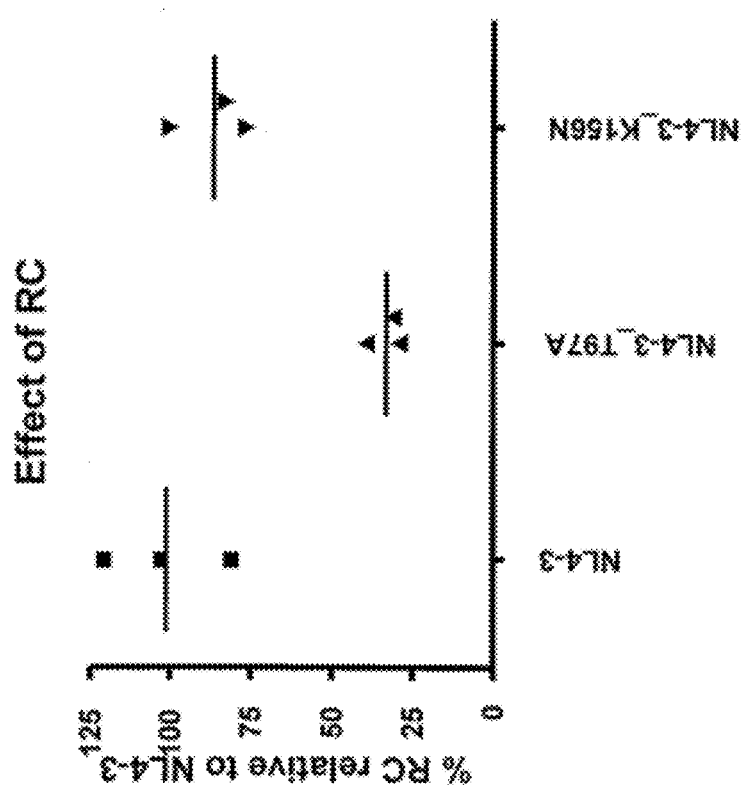

FIG. 19 presents the results of phenotypic assays showing that IN mutations in codon 97 cause a reduction in replication capacity in an NL4-3 background.

FIG. 20 presents a table containing the results of phenotypic assays showing that mutations in integrase codons 97 and 156 in combination with previously recognized INSTI resistance mutations result in altered susceptibility to the INSTIs L-diketo acid 1, diketo acid 2, and L-870,810 and in reduced replication capacity.

5. DETAILED DESCRIPTION OF THE INVENTION

In certain aspects, the present invention provides methods for determining whether an HIV-1 is resistant to antiviral therapy with an NNRTI or with AZT. The methods generally comprise detecting whether a mutation or mutations are present in the HIV-1 gene encoding RT that significantly correlate with resistance to an NNRTI or to AZT.

In other aspects, the present invention provides methods for determining whether an HIV-1 has reduced replication capacity. The methods generally comprise detecting whether a mutation or mutations are present in the HIV-1 gene encoding RT that significantly correlate with reduced replication capacity.

In still other aspects, the present invention provides methods for determining whether an HIV-1 has altered susceptibility to antiviral therapy with an INSTI. The methods generally comprise detecting whether a mutation or mutations are present in the HIV-1 gene encoding IN that significantly correlate with altered susceptibility to an INSTI.

5.1 Abbreviations

"NRTI" is an abbreviation for nucleoside reverse transcriptase inhibitor.

"NNRTI" is an abbreviation for non nucleoside reverse transcriptase inhibitor.

"PI" is an abbreviation for protease inhibitor.

"PR" is an abbreviation for protease.

"RT" is an abbreviation for reverse transcriptase.

"IN" is an abbreviation for integrase.

"PCR" is an abbreviation for "polymerase chain reaction."

"HBV" is an abbreviation for hepatitis B virus.

"HCV" is an abbreviation for hepatitis C virus.

"HIV" is an abbreviation for human immunodeficiency virus.

"EFV" is an abbreviation for the NNRTI efavirenz.

"DLV" is an abbreviation for the NNRTI delavirdine.

"NVP" is an abbreviation for the NNRTI nevirapine.

"INSTI" is an abbreviation for a integrase strand transfer inhibitor.

The amino acid notations used herein for the twenty genetically encoded L-amino acids are conventional and are as follows:

| Amino Acid | One-Letter Abbreviation | Three Letter Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |

-continued

| Amino Acid | One-Letter Abbreviation | Three Letter Abbreviation |
|---|---|---|
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Unless noted otherwise, when polypeptide sequences are presented as a series of one-letter and/or three-letter abbreviations, the sequences are presented in the N→C direction, in accordance with common practice.

Individual amino acids in a sequence are represented herein as AN, wherein A is the standard one letter symbol for the amino acid in the sequence, and N is the position in the sequence. Mutations are represented herein as A1NA2, wherein $A_1$ is the standard one letter symbol for the amino acid in the reference protein sequence, A2 is the standard one letter symbol for the amino acid in the mutated protein sequence, and N is the position in the amino acid sequence. For example, a G25M mutation represents a change from glycine to methionine at amino acid position 25. Mutations may also be represented herein as NA2, wherein N is the position in the amino acid sequence and A2 is the standard one letter symbol for the amino acid in the mutated protein sequence (e.g., 25M, for a change from the wild-type amino acid to methionine at amino acid position 25). Additionally, mutations may also be represented herein as A1NX, wherein A1 is the standard one letter symbol for the amino acid in the reference protein sequence, N is the position in the amino acid sequence, and X indicates that the mutated amino acid can be any amino acid (e.g., G25X represents a change from glycine to any amino acid at amino acid position 25). This notation is typically used when the amino acid in the mutated protein sequence is either not known or, if the amino acid in the mutated protein sequence could be any amino acid, except that found in the reference protein sequence. The amino acid positions are numbered based on the full-length sequence of the protein from which the region encompassing the mutation is derived. Representations of nucleotides and point mutations in DNA sequences are analogous.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Unless specified otherwise, single-stranded nucleic acid sequences that are represented as a series of one-letter abbreviations, and the top strand of double-stranded sequences, are presented in the 5'→3' direction.

5.2 Definitions

As used herein, the following terms shall have the following meanings:

A "phenotypic assay" is a test that measures a phenotype of a particular virus, such as, for example, HIV, or a population of viruses, such as, for example, the population of HIV infecting a subject. The phenotypes that can be measured include, but are not limited to, the resistance or susceptibility of a virus, or of a population of viruses, to a specific anti-viral agent or that measures the replication capacity of a virus.

A "genotypic assay" is an assay that determines a genotype of an organism, a part of an organism, a population of organisms, a gene, a part of a gene, or a population of genes. Typically, a genotypic assay involves determination of the nucleic acid sequence of the relevant gene or genes. Such assays are frequently performed in HIV to establish, for example, whether certain mutations are associated with drug resistance or hypersusceptibility or altered replication capacity are present.

As used herein, "genotypic data" are data about the genotype of, for example, a virus. Examples of genotypic data include, but are not limited to, the nucleotide or amino acid sequence of a virus, a population of viruses, a part of a virus, a viral gene, a part of a viral gene, or the identity of one or more nucleotides or amino acid residues in a viral nucleic acid or protein.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-X program, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease or reverse transcriptase is the protease or reverse transcriptase coding sequence, respectively, present in NL4-3 HIV (SEQ ID NO:5; GenBank Accession No. AF324493). Likewise, the reference protease or reverse transcriptase polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, Methods in Enzymology 65:499), dideoxy sequencing (Sanger et al., 1977, Proc. Natl. Acad. Sci. USA 74:5463) or hybridization-based approaches (see e.g., Sambrook et al., 2001, Molecular Cloning: A Laboratory Manual, Cold Spring Harbor Laboratory, 3.sup.rd ed., NY; and Ausubel et al., 1989, Current Protocols in Molecular Biology, Greene Publishing Associates and Wiley Interscience, NY).

A "mutant" is a virus, gene or protein having a sequence that has one or more changes relative to a reference virus, gene or protein.

The terms "peptide," "polypeptide" and "protein" are used interchangeably throughout.

The term "wild-type" refers to a viral genotype that does not comprise a mutation known to be associated with drug resistance.

The terms "polynucleotide," "oligonucleotide" and "nucleic acid" are used interchangeably throughout.

5.3 Methods of Determining Altered Susceptibility to an NRTI, NNRTI, or INSTI

In certain aspects, the present invention provides methods for determining whether an HIV-1 is has altered susceptibility to an NRTI, NNRTI, or INSTI. In general, the methods comprise detecting whether mutations significantly correlated with altered susceptibility to an NRTI, NNRTI, or INSTI are present in the gene encoding reverse transcriptase or integrase of the HIV-1, as demonstrated by the examples below. In certain embodiments, the HIV-1 has increased susceptibility, e.g., hypersusceptibility, to the NRTI, NNRTI, or INSTI. In certain embodiments, the HIV-1 has decreased susceptibility, e.g., is resistant, to the NRTI, NNRTI, or INSTI.

In certain embodiments, viruses that exhibit an IC50 2.5 fold higher than wild-type virus were designated as having resistance to an NRTI, NNRTI, or INSTI. In some embodiments, viruses that exhibit an $IC_5 0$ 2.0 fold higher than wild-type virus were designated as having resistance to an NRTI, NNRTI, or INSTI. In some embodiments, viruses that exhibit an $IC_5 0$ 1.5 fold higher than wild-type virus were designated as having resistance to an NRTI, NNRTI, or INSTI. In certain embodiments, viruses that exhibit an IC50 2.5 fold lower than wild-type virus were designated as having hypersusceptibility to an NRTI, NNRTI, or INSTI. In some embodiments, viruses that exhibit an IC50 2.0 fold lower than wild-type virus were designated as having hypersusceptibility to an NRTI, NNRTI, or INSTI. In some embodiments, viruses that exhibit an IC50 1.5 fold lower than wild-type virus were designated as having hypersusceptibility to an NRTI, NNRTI, or INSTI.

Therefore, in certain embodiments, the invention provides a method for determining whether a human immunodeficiency virus 1 (HIV-1) is resistant to a non-nucleoside reverse transcriptase inhibitor (NNRTI) or ziduvine (AZT), comprising detecting whether a mutation at codon 348 or 369 is present in a gene encoding reverse transcriptase of the HIV-1, wherein the presence of the mutation correlates with resistance to an NNRTI or to AZT, such that if the mutation is present, the HIV-1 is resistant to the NNRTI or to AZT. In certain embodiments, the mutation at codon 348 encodes isoleucine (I). In certain embodiments, the mutation at codon 369 encodes isoleucine (I) or alanine (A). In certain embodiments, the NNRTI is efavirenz (EFV), nevirapine (NVP), or delavirdine (DLV). In certain embodiments, the NNRTI is EFV. In certain embodiments, the NNRTI is NVP. In certain embodiments, the NNRTI is DLV. In certain embodiments, the HIV-1 is determined to be resistant to AZT.

In certain embodiments, the methods further comprise detecting whether a mutation at codon 103, 179, 190, or 225 is present in the gene encoding reverse transcriptase. In certain embodiments, a mutation at codon 103 is detected. In certain embodiments, the mutation at codon 103 encodes asparagine (N), arginine (R), serine (S), glutamine (Q), or threonine (T). In certain embodiments, a mutation at codon 225 is detected. In certain embodiments, the mutation at codon 225 encodes histidine (H). In certain embodiments, a mutation at codon 103 and a mutation at codon 225 are detected. In certain embodiments, the mutation at codon 103 encodes asparagine (N), arginine (R), serine (S), glutamine (Q), or threonine (T). In certain embodiments, the mutation at codon 225 encodes histidine (H). In certain embodiments, a mutation at codon 190 is detected. In certain embodiments, the mutation at codon 190 encodes serine (S). In certain embodiments, mutations at codon 103 and codon 179 are detected. In certain embodiments, the mutation at codon 103 encodes asparagine (N), arginine (R), serine (S), glutamine (Q), or threonine (T). In certain embodiments, the mutation at codon 179 encodes aspartic acid (D). In certain embodiments, the NNRTI is EFV, NVP, or DLV. In certain embodiments, the NNRTI is EFV. In certain embodiments, the NNRTI is NVP. In certain embodiments, the NNRTI is DLV.

In another aspect, the invention provides a method for determining whether a human immunodeficiency virus 1 (HIV-1) is resistant to a non-nucleoside reverse transcriptase. inhibitor (NNRTI), comprising detecting whether a mutation at codon 399 in combination with a mutation at codon 103, 179, or 190 is present in a gene encoding reverse transcriptase of the HIV-1, wherein the presence of the mutations correlates with resistance to an NNRTI, such that if the mutation is present, the HIV-1 is resistant to the NNRTI. In certain embodiments, the mutation at codon 399 encodes aspartic acid (D). In certain embodiments, a mutation at codon 103 is detected. In certain embodiments, the mutation at codon 103 encodes asparagine (N), arginine (R), serine (S), glutamine (Q), or threonine (T). In certain embodiments, a mutation at codon 179 is detected. In certain embodiments, the mutation at codon 179 encodes aspartic acid (D). In certain embodiments, a mutation at codon 190 is detected. In certain embodiments, the mutation at codon 190 encodes serine (S). In certain embodiments, mutations at codons 103 and 179 are detected. In certain embodiments, the mutation at codon 103 encodes asparagine (N), arginine (R), serine (S), glutamine (Q), or threonine (T). In certain embodiments, the mutation at codon 179 encodes aspartic acid (D). In certain embodiments, the NNRTI is EFV, NVP, or DLV. In certain embodiments, the NNRTI is EFV. In certain embodiments, the NNRTI is NVP. In certain embodiments, the NNRTI is DLV.

In another aspect, the invention provides a method for determining whether an HIV-1 has reduced replication capacity relative to a reference HIV-1, comprising detecting, in a nucleic acid encoding reverse transcriptase of the HIV-1, a mutation at codon 369 or in a nucleic acid encoding integrase of the HIV-1, a mutation at codon 97, wherein the presence of the mutation correlates with reduced replication capacity such that if the mutation is present, the HIV-1 has reduced replication capacity relative to a reference HIV-1. In certain embodiments, a mutation at codon 369 of reverse transcriptase is detected. In certain embodiments, the mutation at codon 369 encodes isoleucine (I). In certain embodiments, a mutation at codon 97 of Integrase is detected. In certain embodiments, the mutation at codon 97 encodes alanine (A). In certain embodiments, the reference HIV-1 is NL4-3. In certain embodiments, the reference HIV-1 has an identical genotype to the HIV-1 having its replication capacity determined except for codon 369 of reverse transcriptase or codon 97 of integrase. In certain embodiments, the genotype of the reference HIV-1 differs from the HIV-1 having its replication capacity determined at codon 369 of reverse transcriptase. In certain embodiments, the genotype of the reference HIV-1 differs from the HIV-1 having its replication capacity determined at codon 97 of integrase.

In yet another aspect, the invention provides a method for determining whether a human immunodeficiency virus 1 (HIV-1) has altered susceptibility to a integrase strand transfer inhibitor (INSTI), comprising detecting whether a mutation at codon 97 or codon 156 is present in a gene encoding integrase of the HIV-1, wherein the presence of the mutations correlates with altered susceptibility to an INSTI, such that if the mutation is present, the HIV-1 has altered susceptibility to the INSTI. In certain embodiments, the HIV-1 exhibits increased susceptibility to the INSTI. In certain embodiments, the HIV-1 exhibits decreased susceptibility to the INSTI. In certain embodiments, a mutation at codon 97 is detected. In certain embodiments, the mutation at codon 97 encodes alanine (A). In certain embodiments, a mutation at codon 156 is detected. In certain embodiments, the mutation at codon 156 encodes asparagines (N). In certain embodiments, the INSTI is a napthyridine carboximide. In certain embodiments, the INSTI is L-870,810.

In certain embodiments, the methods further comprise detecting whether a mutation at codon 66, 72, 121, 125, 154, or 155 is present in the gene encoding integrase. In certain embodiments, the HIV-1 exhibits decreased susceptibility to the INSTI. In certain embodiments, a mutation at codon 66 is detected. In certain embodiments, the mutation at codon 66 encodes isoleucine (I). In certain embodiments, a mutation at codon 72 is detected. In certain embodiments, the mutation at codon 72 encodes isoleucine (I). In certain embodiments, a mutation at codon 121 is detected. In certain embodiments, the mutation at codon 121 encodes tyrosine (Y). In certain embodiments, a mutation at codon 125 is detected. In certain embodiments, the mutation at codon 125 encodes lysine (K). In certain embodiments, a mutation at codon 154 is detected. In certain embodiments, the mutation at codon 154 encodes isoleucine (I). In certain embodiments, a mutation at codon 155 is detected. In certain embodiments, the mutation at codon 155 encodes serine (S). In certain embodiments, mutations at codons 72, 121, and 125 are detected. In certain embodiments, the mutation at codon 72 encodes isoleucine (I), the mutation at codon 121 encodes tyrosine (Y), and the mutation at codon 125 encodes lysine (K). In certain embodiments, mutations at codons 66 and 154 are detected. In certain embodiments, the mutation at codon 66 encodes isoleucine (I) and the mutation at codon 154 encodes isoleucine (I). In certain embodiments, the INSTI is a diketo acid. In certain embodiments, the INSTI is diketo acid 1 or diketo acid 2. In certain embodiments, the INSTI is a napthyridine carboximide. In certain embodiments, the INSTI is L-870,810.

In another aspect, the methods comprise determining whether a subject is infected with an HIV that is sensitive to an NRTI, NNRTI, or INSTI according to a method of the invention, then advising a medical professional of the treatment option of administering to the subject an effective amount of an NRTI, NNRTI, or INSTI, respectively. In another aspect, the methods comprise determining whether a subject is infected with an HIV that is resistant to an NRTI, NNRTI, or INSTI according to a method of the invention, then advising a medical professional of the treatment option of administering to the subject an effective amount of an NRTI, NNRTI, or INSTI, respectively. Preferably, the HIV that is resistant to the NRTI, NNRTI, or INSTI comprises a mutation associated with NRTI, NNRTI, or INSTI resistance, respectively, that is associated with impaired replication. Such mutations are described herein and in U.S. Pub. No. 2004/0063191 (abandoned) and U.S. application Ser. No. 11/052,741 (abandoned) and Ser. No. 11/092,204 (abandoned), which are incorporated by reference in their entireties. In certain embodiments, the NRTI is AZT. In certain embodiments, the NNRTI is EFV, DLV, or NVP. In certain embodiments, the INSTI is diketo acid 1, diketo acid 2 or L-870,810. In some embodiments, the methods comprise determining whether a subject is infected with an HIV that is resistant to an NRTI, NNRTI, or INSTI according to a method of the invention, then advising a medical professional of the option not to treat the subject with an NRTI, NNRTI, or INSTI, respectively. In certain embodiments, the NRTI is AZT. In certain embodiments, the NNRTI is EFV, DLV, or NVP. In certain embodiments, the INSTI is diketo acid 1, diketo acid 2 or L-870,810.

In still another aspect, the methods comprise determining that a subject is infected with an HIV that is resistant to an NRTI, NNRTI, or INSTI according to a method of the invention, and administering to the subject a combination of anti-HIV agents that comprises an effective amount of an NRTI, NNRTI, or INSTI, respectively. Preferably, the HIV that is resistant to the NRTI, NNRTI, or INSTI comprises a mutation associated with NRTI, NNRTI, or INSTI resistance, respectively, that is associated with impaired replication, as discussed above. In certain embodiments, the NRTI is AZT. In certain embodiments, the NNRTI is EFV, DLV, or NVP. In certain embodiments, the INSTI is diketo acid 1, diketo acid 2 or L-870,810. In some embodiments, the methods comprise determining that a subject is infected with an HIV that is resistant to an NRTI, NNRTI, or INSTI according to a method of the invention, and administering to the subject a combination of anti-HIV agents that does not comprise the NRTI, NNRTI, or INSTI, respectively. In certain embodiments, the NRTI is AZT. In certain embodiments, the NNRTI is EFV, DLV, or NVP. In certain embodiments, the INSTI is diketo acid 1, diketo acid 2 or L-870,810.

In still another aspect, the methods comprise determining that a subject is infected with an HIV that is resistant to an NRTI, NNRTI, or INSTI according to a method of the invention at a first time, then determining whether the subject remains infected with an HIV that is resistant to an NRTI, NNRTI, or INSTI according to a method of the invention at a later second time. Preferably, the subject has undergone or has been undergoing an anti-HIV therapy during the period between the first and second time. In other embodiments, the methods comprise determining that a subject is infected with an HIV that is sensitive to an NRTI, NNRTI, or INSTI according to a method of the invention at a first time, then determining whether the subject is infected with an HIV that is resistant to an NRTI, NNRTI, or INSTI according to a method of the invention at a later second time. Preferably, the subject has undergone or has been undergoing an anti-HIV therapy that comprises an effective amount of an NRTI, NNRTI, or INSTI during the period between the first and second time.

5.4 Measuring Resistance of HIV-1 to an Anti-Viral Drug

Any method known in the art can be used to determine a viral drug resistance phenotype, without limitation. See e.g., U.S. Pat. Nos. 5,837,464 and 6,242,187, each of which is hereby incorporated by reference in its entirety.

In certain embodiments, the phenotypic analysis is performed using recombinant virus assays ("RVAs"). RVAs use virus stocks generated by homologous recombination between viral vectors and viral gene sequences, amplified from the patient virus. In certain embodiments, the viral vector is a HIV vector and the viral gene sequences are protease and/or reverse transcriptase and/or gag sequences.

In preferred embodiments, the phenotypic analysis of NRTI, NNRTI, or INSTI resistance is performed using PHENOSENSE® (phenotypic assay, Monogram Biosciences, Inc., South San Francisco, Calif.). See Petropoulos et al., 2000, Antimicrob. Agents Chemother. 44:920-928; U.S. Pat. Nos. 5,837,464 and 6,242,187. PHENOSENSE® is a phenotypic assay that achieves the benefits of phenotypic testing and overcomes the drawbacks of previous assays. Because the assay has been automated, PHENOSENSE® (phenotypic assay) provides high throughput methods under controlled conditions for determining NRTI, NNRTI, or INSTI resistance, susceptibility, or hypersusceptibility of a large number of individual viral isolates.

The result is an assay that can quickly and accurately define both the replication capacity and the susceptibility profile of a patient's HIV (or other virus) isolates to all currently available antiretroviral drugs, including the NRTI AZT, the NNRTIs EFV, DLV, and NVP, and the INSTIs diketo acid 1, diketo acid 2, and L-870,810. PHENOSENSE® (phenotypic assay) can obtain results with only one round of viral replication, thereby avoiding selection of subpopulations of virus that can occur during preparation of viral stocks required for assays that rely on fully infectious virus. Further, the results are both quantitative, measuring varying degrees of replication capacity or antiviral resistance or susceptibility, and sensitive, as the test can be performed on blood specimens with a viral load of about 500 copies/mL or above and can detect minority populations of some drug-resistant virus at concentrations of 10% or less of total viral population. Finally, the replication capacity and antiviral drug resistance results are reproducible and can vary by less than about 0.25 logs in about 95% of the assays performed.

PHENOSENSE® (phenotypic assay) can be used with nucleic acids from amplified viral gene sequences. As discussed below, the nucleic acid can be amplified from any sample known by one of skill in the art to contain a viral gene sequence, without limitation. For example, the sample can be a sample from a human or an animal infected with the virus or a sample from a culture of viral cells. In certain embodiments, the viral sample comprises a genetically modified laboratory strain. In other embodiments, the viral sample comprises a wild-type isolate.

A resistance test vector ("RTV") can then be constructed by incorporating the amplified viral gene sequences into a replication defective viral vector by using any method known in the art of incorporating gene sequences into a vector. In one embodiment, restrictions enzymes and conventional cloning methods are used. See Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY. In a preferred embodiment, ApaI and PinAI restriction enzymes are used. Preferably, the replication defective viral vector is the indicator gene viral vector ("IGVV"). In a preferred embodiment, the viral vector contains a means for detecting replication of the RTV. Preferably, the viral vector contains a luciferase expression cassette.

The assay can be performed by first co-transfecting host cells with RTV DNA and a plasmid that expresses the envelope proteins of another retrovirus, for example, amphotropic murine leukemia virus (MLV). Following transfection, viral particles can be harvested from the cell culture and used to infect fresh target cells in the presence of varying amounts of antiviral drug(s). The completion of a single round of viral replication in the fresh target cells can be detected by the means for detecting replication contained in the vector. In a preferred embodiment, the completion of a single round of viral replication results in the production of luciferase. By monitoring the amount of, e.g., luciferase activity in the presence of the varying amounts of antiviral drug(s), a resistance curve can be constructed by plotting luciferase activity versus drug concentration. The resistance of an HIV, or population of HIV, can be determined by measuring the concentration of antiviral drug at which the luciferase activity detected is half-maximal. This number, the $IC_{50}$, provides a standard and convenient measure of drug resistance.

In preferred embodiments, PHENOSENSE® (phenotypic assay) is used to evaluate the AZT, EFV, DLV, NVP, diketo acid 1, diketo acid 2, and/or L-870,810 resistance phenotype of HIV-1. In other embodiments, PHENOSENSE® (phenotypic assay) is used to evaluate the AZT, EFV, DLV, NVP, diketo acid 1, diketo acid 2, and/or L-870,810 resistance phenotype of HIV-2. In certain embodiments, the HIV-1 strain that is evaluated is a wild-type isolate of HIV-1. In other embodiments, the HIV-1 strain that is evaluated is a mutant strain of HIV-1. In certain embodiments, such mutant strains can be isolated from patients. In other embodiments, the mutant strains can be constructed by site-directed mutagenesis or other equivalent techniques known to one of skill in the art. In still other embodiments, the mutant strains can be isolated from cell culture. The cultures can comprise multiple passages through cell culture in the presence of antiviral compounds to select for mutations that accumulate in culture in the presence of such compounds.

In one embodiment, viral nucleic acid, for example, HIV-1 RNA is extracted from plasma samples, and a fragment of, or entire viral genes can be amplified by methods such as, but not limited to PCR. See, e.g., Hertogs et aL, 1998, *Antimicrob Agents Chemother* 42(2):269-76. In one example, a 2.2-kb fragment containing the entire HIV-1 PR- and RT-coding sequence is amplified by nested reverse transcription-PCR. The pool of amplified nucleic acid, for example, the PR-RT-coding sequences, is then cotransfected into a host cell such as CD4+ T lymphocytes (MT4) with the pGEMT3deltaPRT plasmid from which most of the PR (codons 10 to 99) and RT (codons 1 to 482) sequences are deleted. Homologous recombination leads to the generation of chimeric viruses containing viral coding sequences, such as the PR- and RT-coding sequences derived from HIV-1 RNA in plasma. Alternately, other patient segments can be amplified as described, for example, in Example 2, below. The replication capacities or antiviral drug resistance phenotypes of the chimeric viruses can be determined by any cell viability assay known in the art, and compared to replication capacities or antiviral drug resistance of a statistically significant number of individual viral isolates to assess whether a virus has altered replication capacity or is resistant or hypersusceptible to the antiviral drug. For example, an MT4 cell-3-(4,5-dimethylthiazol-2-yl)-2,5-diphenyltetrazolium bromide-based cell viability assay can be used in an automated system that allows high sample throughput.

In another embodiment, competition assays can be used to assess replication capacity of one viral strain relative to another viral strain. For example, two infectious viral strains can be co-cultivated together in the same culture medium. See, e.g., Lu et al., 2001, *JAIDS* 27:7-13, which is incorporated by reference in its entirety. By monitoring the course of each viral strain's growth, the fitness of one strain relative to the other can be determined. By measuring many viruses' fitness relative to a single reference virus, an objective measure of each strain's fitness can be determined.

Other assays for evaluating the phenotypic susceptibility of a virus to anti-viral drugs known to one of skill in the art can be adapted to determine replication capacity or to determine antiviral drug susceptibility or resistance. See, e.g., Shi and Mellors, 1997, *Antimicrob Agents Chemother.* 41(12):2781-85; Gervaix et al., 1997, *Proc Natl Acad Sci U S. A.* 94(9): 4653-8; Race et al., 1999, *AIDS* 13:2061-2068, incorporated herein by reference in their entireties.

In addition, the phenotypic assays described above can also be used to determine the effectiveness of candidate compounds. Generally, such methods comprise performing the phenotypic assay in the presence and absence of the candidate compound, wherein the difference in activity or expression of the indicator gene indicates the effectiveness of the candidate compound. Advantageously, the methods can be performed in the presence of a mutation associated with NNRTI resistance as disclosed herein. By performing such assays in the presence of such mutations, candidate compounds can be identified that have beneficial interactions with the NNRTIs to which the virus is hyper susceptible. In certain embodiments, the candidate compound will have an additive effect on viral inhibition with the NNRTI. In preferred embodiments, the candidate compound will have a synergistic effect on viral inhibition with the NNRTI. Further guidance may be found in performing the assays to determine the effectiveness of candidate compounds in Petropoulos et al., 2000, *Antimicrob. Agents Chemother.* 44:920-928; and U.S. Pat. Nos. 5,837,464 and 6,242,187.

5.4.1 Detecting the Presence or Absence of Mutations in a Virus

The presence or absence of an mutation associated with NRTI, NNRTI, or INSTI resistance or susceptibility according to the present invention in a virus can be determined by any means known in the art for detecting a mutation. The mutation can be detected in the viral gene that encodes a particular protein, or in the protein itself, i.e., in the amino acid sequence of the protein.

In one embodiment, the mutation is in the viral genome. Such a mutation can be in, for example, a gene encoding a viral protein, in a genetic element such as a cis or trans acting regulatory sequence of a gene encoding a viral protein, an intergenic sequence, or an intron sequence. The mutation can affect any aspect of the structure, function, replication or environment of the virus that changes its resistance to an anti-viral treatment and/or its replication capacity. In one embodiment, the mutation is in a gene encoding a viral protein that is the target of an currently available anti-viral treatment. In other embodiments, the mutation is in a gene or other genetic element that is not the target of a currently-available anti-viral treatment.

A mutation within a viral gene can be detected by utilizing any suitable technique known to one of skill in the art without limitation. Viral DNA or RNA can be used as the starting point for such assay techniques, and may be isolated according to standard procedures which are well known to those of skill in the art.

The detection of a mutation in specific nucleic acid sequences, such as in a particular region of a viral gene, can be accomplished by a variety of methods including, but not limited to, restriction-fragment-length-polymorphism detection based on allele-specific restriction-endonuclease cleavage (Kan and Dozy, 1978, Lancet ii:910-912), mismatch-repair detection (Faham and Cox, 1995, Genome Res 5:474-482), binding of MutS protein (Wagner et aL, 1995, Nucl Acids Res 23:3944-3948), denaturing-gradient gel electrophoresis (Fisher et al., 1983, Proc. Natl. Acad. Sci. US.A. 80:1579-83), single-strand-conformation-polymorphism detection (Orita et al., 1983, Genomics 5:874-879), RNAase cleavage at mismatched base-pairs (Myers et al., 1985, Science 230:1242), chemical (Cotton et at, 1988, Proc. Natl. Acad. Sci. U.S.A. 85:4397-4401) or enzymatic (Youil et al., 1995, Proc. Natl. Acad. Sci. US.A. 92:87-91) cleavage of heteroduplex DNA, methods based on oligonucleotide-specific primer extension (Syvanen et ai., 1990, Genomics 8:684-692), genetic bit analysis (Nikiforov et al., 1994, Nucl Acids Res 22:4167-4175), oligonucleotide-ligation assay (Landegren et al., 1988, Science 241:1077), oligonucleotide-specific ligation chain reaction ("LCR") (Barrany, 1991, Proc. Natl. Acad. Sci. U.S.A. 88:189-193), gap-LCR (Abravaya et al., 1995, Nucl Acids Res 23:675-682), radio-active or fluorescent DNA sequencing using standard procedures well known in the art, and peptide nucleic acid (PNA) assays (Drum et al., 1993, Nucl. Acids Res. 21:5332-5356; Thiede et al., 1996, Nucl. Acids Res. 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, *J. Moi. Biol.* 98:503-517), single stranded conformational polymorphism analyses (SSCP) (Orita et al., 1989, *Proc. Natl. Acad. Sci. USA* 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods for the detection of a gene-specific mutation can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

These techniques can easily be adapted to provide high-throughput methods for detecting mutations in viral genomes. For example, a gene array from Affymetrix (Affymetrix, Inc., Sunnyvale, Calif.) can be used to rapidly identify genotypes of a large number of individual viruses. Affymetrix gene arrays, and methods of making and using such arrays, are described in, for example, U.S. Pat. Nos. 6,551,784, 6,548,257, 6,505,125, 6,489,114, 6,451,536, 6,410,229, 6,391,550, 6,379,895, 6,355,432, 6,342,355, 6,333,155, 6,308,170, 6,291,183, 6,287,850, 6,261,776, 6,225,625, 6,197,506, 6,168,948, 6,156,501, 6,141,096, 6,040,138, 6,022,963, 5,919,523, 5,837,832, 5,744,305, 5,834,758, and 5,631,734, each of which is hereby incorporated by reference in its entirety.

In addition, Ausubel et al., eds., *Current Protocols in Molecular Biology,* 2002, Vol. 4, Unit 25B, Ch. 22, which is hereby incorporated by reference in its entirety, provides further guidance on construction and use of a gene array for determining the genotypes of a large number of viral isolates. Finally, U.S. Pat. Nos. 6,670,124; 6,617,112; 6,309,823; 6,284,465; and 5,723,320, each of which is incorporated by reference in its entirety, describe related array tectmoiogles that can reacmy be adapted for rapid identification of a large number of viral genotypes by one of skill in the art.

Alternative diagnostic methods for the detection of gene specific nucleic acid molecules may involve their amplification, e.g., by PCR (U.S. Pat. Nos. 4,683,202; 4,683,195;

4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine whether a gene mutation exists.

Additionally, the nucleic acid can be sequenced by any sequencing method known in the art. For example, the viral DNA can be sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499. See also the techniques described in Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY.

Antibodies directed against the viral gene products, i.e., viral proteins or viral peptide fragments can also be used to detect mutations in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

5.4.2 Correlating Mutations with Altered Susceptibility to an NRTI, NNRTI, or INSTI Any method known in the art can be used to determine whether a mutation is correlated with altered susceptibility to an NRTI, NNRTI, or INSTI. In one embodiment, univariate analysis is used to identify mutations correlated with altered susceptibility to an NRTI, NNRTI, or INSTI. Univariate analysis yields P values that indicate the statistical significance of the correlation. In such embodiments, the smaller the P value, the more significant the measurement. Preferably the P values will be less than 0.05. More preferably, P values will be less than 0.01. Even more preferably, the P value will be less than 0.005. P values can be calculated by any means known to one of skill in the art. In one embodiment, P values are calculated using Fisher's Exact Test. In another embodiment, P values can be calculated with Student's t-test. See, e.g., David Freedman, Robert Pisani & Roger Purves, 1980, STATISTICS, W. W. Norton, New York. In certain embodiments, P values can be calculated with both Fisher's Exact Test and Student's t-test. In such embodiments, P values calculated with both tests are preferably less than 0.05. However, a correlation with a P value that is less than 0.10 in one test but less than 0.05 in another test can still be considered to be a marginally significant correlation. Such mutations are suitable for further analysis with, for example, multivariate analysis. Alternatively, further univariate analysis can be performed on a larger sample set to confirm the significance of the correlation.

Further, an odds ratio can be calculated to determine whether a mutation correlates with altered susceptibility to an NRTI, NNRTI, or INSTI. Generally, calculation of odds rations depends on dividing the percentage of virus that comprise a particular mutation or mutations that are identified as having altered susceptibility to an NRTI, NNRTI, or INSTI by the percentage of virus with the same mutation or mutations that are identified as not having altered susceptibility to an NRTI, NNRTI, or INSTI. In certain embodiments, an odds ratio that is greater than one indicates that the mutation does not correlate with altered susceptibility to an NRTI, NNRTI, or INSTI. In certain embodiments, an odds ratio that is greater than one indicates that the mutation correlates with altered susceptibility to an NRTI, NNRTI, or INSTI.

In yet another embodiment, multivariate analysis can be used to determine whether a mutation correlates with altered susceptibility to an NRTI, NNRTI, or INSTI. Any multivariate analysis known by one of skill in the art to be useful in calculating such a correlation can be used, without limitation. In certain embodiments, a statistically significant number of virus's resistance or susceptibility phenotypes, e.g., $IC_50$, can be determined. These IC50 values can then be divided into groups that correspond to percentiles of the set of IC50 values observed.

After assigning each virus's IC50 value to the appropriate group, the genotype of that virus can be assigned to that group. By performing this method for all viral isolates, the number of instances of a particular mutation in a given percentile of NRTI, NNRTI, or INSTI resistance or susceptibility can be observed. This allows the skilled practitioner to identify mutations that correlate with altered susceptibility to an NRTI, NNRTI, or INSTI.

Finally, in yet another embodiment, regression analysis can be performed to identify mutations that best predict NRTI, NNRTI, or INSTI resistance or susceptibility. In such embodiments, regression analysis is performed on a statistically significant number of viral isolates for which genotypes and NRTI, NNRTI, or INSTI resistance or susceptibility phenotypes have been determined. The analysis then identifies which mutations appear to best predict, e.g., most strongly correlate with altered susceptibility to an NRTI, NNRTI, or INSTI. Such analysis can then be used to construct rules for predicting altered susceptibility to an NRTI, NNRTI, or INSTI based upon knowledge of the genotype of a particular virus, described below. In certain embodiments, software such as, for example, CART 5.0, Prism 4.0, or Insightful Miner 3.0 can be used to perform the analysis that identifies the mutations that appear to best predict altered susceptibility to an NRTI, NNRTI, or INSTI.

5.4.3 Computer-Implemented Methods for Determining Altered Susceptibility to an NRTI, NNRTI, or INSTI and Related Articles In another aspect, the present invention provides computer-implemented methods for determining whether an HIV-1 has altered susceptibility to an NRTI, NNRTI, or INSTI. In such embodiments, the methods of the invention are adapted to take advantage of the processing power of modern computers. One of skill in the art can readily adapt the methods in such a manner.

Therefore, in certain embodiments, the invention provides a computer-implemented method for determining that an HIV-1 is resistant to an NNRTI or AZT, comprising inputting genetic information into a memory system of a computer, wherein the genetic information indicates that the HIV-1 has a gene encoding reverse transcriptase with a mutation at codon 348 or 369, inputting a correlation between the presence of the mutations and resistance to an NNRTI or AZT into the memory system of the computer, and determining that the HIV-1 is resistant to the NNRTI or AZT. In certain embodiments, the genetic information indicates that the mutation at codon 348 encodes isoleucine (I). In certain embodiments, the genetic information indicates that the mutation at codon 369 encodes isoleucine (I) or alanine (A). In certain embodiments, the NNRTI is EFV, DLV, or NVP. In certain embodiments, the NNRTI is EFV. In certain embodiments, the NNRTI is DLV. In certain embodiments, the NNRTI is NVP. In certain embodiments, the HIV-1 is determined to be resistant to AZT.

In certain embodiments, the genetic information further indicates that a mutation at codon 103, 179, 190, or 225 is present in the gene encoding reverse transcriptase in addition to the mutation in codon 348 or 369. In certain embodiments, the genetic information indicates that a mutation at codon 103 is present. In certain embodiments, the genetic information indicates that the mutation at codon 103 encodes asparagine (N), arginine (R), serine (S), glutamine (Q), or threonine (T). In certain embodiments, the genetic information indicates that a mutation at codon 225 is present. In certain embodiments, the genetic information indicates that the mutation at codon 225 encodes histidine (H). In certain embodiments, the genetic information indicates that a mutation at codon 103 and a mutation at codon 225 are present. In certain embodiments, the genetic information indicates that the mutation at codon 103 encodes asparagine (N), arginine (R), serine (S), glutamine (Q), or threonine (T). In certain embodiments, the genetic information indicates that the mutation at codon 225 encodes histidine (H). In certain embodiments, a mutation at codon 190 is present. In certain embodiments, the genetic information indicates that the mutation at codon 190 encodes serine (S). In certain embodiments, the genetic information indicates that mutations at codon 103 and codon 179 are present. In certain embodiments, the genetic information indicates that the mutation at codon 103 encodes asparagine (N), arginine (R), serine (S), glutamine (Q), or threonine (T). In certain embodiments, the genetic information indicates that the mutation at codon 179 encodes aspartic acid (D). In certain embodiments, the NNRTI is EFV, NVP, or DLV. In certain embodiments, the NNRTI is EFV. In certain embodiments, the NNRTI is NVP. In certain embodiments, the NNRTI is DLV.

In another aspect, the invention provides a computer-implemented method for determining that an HIV-1 is resistant to an NNRTI, comprising inputting genetic information into a memory system of a computer, wherein the genetic information indicates that the HIV-1 has a gene encoding reverse transcriptase with a mutation at codon 399 in combination with a mutation at codon 103, 179, or 190, inputting a correlation between the presence of the mutations and resistance to an NNRTI into the memory system of the computer, and determining that the HIV-1 is resistant to the NNRTI. In certain embodiments, the mutation at codon 399 encodes aspartic acid (D). In certain embodiments, the genetic information indicates that a mutation at codon 103 is present. In certain embodiments, the genetic information indicates that the mutation at codon 103 encodes asparagine (N), arginine (R), serine (S), glutamine (Q), or threonine (T). In certain embodiments, the genetic information indicates that a mutation at codon 179 is present. In certain embodiments, the genetic information indicates that the mutation at codon 179 encodes aspartic acid (D). In certain embodiments, the genetic information indicates that a mutation at codon 190 is present. In certain embodiments, the genetic information indicates that the mutation at codon 190 encodes serine (S). In certain embodiments, the genetic information indicates that mutations at codons 103 and 179 are present. In certain embodiments, the genetic information indicates that the mutation at codon 103 encodes asparagine (N), arginine (R), serine (S), glutamine (Q), or threonine (T). In certain embodiments, the genetic information indicates that the mutation at codon 179 encodes aspartic acid (D). In certain embodiments, the NNRTI is EFV, NVP, or DLV. In certain embodiments, the NNRTI is EFV. In certain embodiments, the NNRTI is NVP. In certain embodiments, the NNRTI is DLV.

In another aspect, the invention provides a computer-implemented method for determining that an HIV-1 has reduced replication capacity relative to a reference HIV-1, comprising inputting genetic information into a memory system of a computer, wherein the genetic information indicates that the HIV-1 has a gene encoding reverse transcriptase with a mutation at codon 369 or a gene encoding integrase with a mutation at codon 97, inputting a correlation between the presence of the mutations and reduced replication capacity into the memory system of the computer, and determining that the HIV-1 has reduced replication capacity relative to a reference HIV. In certain embodiments, the genetic information indicates that a mutation at codon 369 of reverse transcriptase is present. In certain embodiments, the genetic information indicates that the mutation at codon 369 encodes isoleucine (I). In certain embodiments, the genetic information indicates that a mutation at codon 97 of integrase is present. In certain embodiments, the genetic information indicates that the mutation at codon 97 encodes alanine (A). In certain embodiments, the reference HIV-1 is NL4-3. In certain embodiments, the reference HIV-1 has an identical genotype to the HIV-1 having its replication capacity determined except for codon 369 of reverse transcriptase or codon 97 of integrase. In certain embodiments, the genotype of the reference HIV-1 differs from the HIV-1 having its replication capacity determined at codon 369 of reverse transcriptase. In certain embodiments, the genotype of the reference HIV-1 differs from the HIV-1 having its replication capacity determined at codon 97 of integrase.

In another aspect, the invention provides a computer-implemented method for determining that an HIV-1 has altered susceptibility to a integrase strand transfer inhibitor (INSTI), comprising inputting genetic information into a memory system of a computer, wherein the genetic information indicates that the HIV-1 has a gene encoding integrase with a mutation at codon 97 or 156, inputting a correlation between the presence of the mutations and altered susceptibility to an INSTI into the memory system of the computer, and determining that the HIV-1 has altered susceptibility to the INSTI. In certain embodiments, the HIV-1 exhibits increased susceptibility to the INSTI. In certain embodiments, the HIV-1 exhibits decreased susceptibility to the INSTI. In certain embodiments, the genetic information indicates that a mutation at codon 97 is present. In certain embodiments, the genetic information indicates that the mutation at codon 97 encodes alanine (A). In certain embodiments, the genetic information indicates that a mutation at codon 156 is present. In certain embodiments, the genetic information indicates that the mutation at codon 156 encodes asparagines (N). In certain embodiments, the INSTI is a napthyridine carboximide. In certain embodiments, the INSTI is L-870, 810.

In certain embodiments, the genetic information further indicates a mutation at codon 66, 72, 121, 125, 154, or 155 is present in the gene encoding integrase. In certain embodiments, the HIV-1 exhibits decreased susceptibility to the INSTI. In certain embodiments, the genetic information indicates that a mutation at codon 66 is present. In certain embodiments, the genetic information indicates that the mutation at codon 66 encodes isoleucine (I). In certain embodiments, the genetic information indicates that a mutation at codon 72 is present. In certain embodiments, the genetic information indicates that the mutation at codon 72 encodes isoleucine (I). In certain embodiments, the genetic information indicates that a mutation at codon 121 is present. In certain embodiments, the genetic information indicates that the mutation at codon 121 encodes tyrosine (Y). In certain embodiments, the genetic information indicates that a mutation at codon 125 is present. In certain embodiments, the genetic information indicates that the mutation at codon 125 encodes lysine (K). In certain embodiments, the genetic information indicates that a mutation at codon 154 is present. In certain embodiments, the genetic information indicates that the mutation at codon 154 encodes isoleucine (I). In certain embodiments, the genetic information indicates that a mutation at codon 155 is present. In certain embodiments, the mutation at codon 155 encodes serine (S). In certain embodiments, the genetic information indicates that mutations at codons 72, 121, and 125 are present. In certain embodiments, the genetic information indicates that the mutation at codon 72 encodes isoleucine (I), the mutation at codon 121 encodes tyrosine (Y), and the mutation at codon 125 encodes lysine (K). In certain embodiments, the genetic information indicates that mutations at codons 66 and 154 are present. In certain embodiments, the genetic information indicates that the mutation at codon 66 encodes isoleucine (I) and the mutation at codon 154 encodes isoleucine (I). In certain embodiments, the INSTI is a diketo acid. In certain embodiments, the INSTI is diketo acid 1 or diketo acid 2. In certain embodiments, the INSTI is a napthyridine carboximide. In certain embodiments, the INSTI is L-870,810.

In certain embodiments, the methods further comprise displaying that the HIV-1 has altered susceptibility to an NRTI, NNRTI, or INSTI on a display of the computer. In certain embodiments, the methods further comprise printing that the HIV-1 has altered susceptibility to an NRTI, NNRTI, or INSTI. In certain embodiments, the methods further comprise displaying that the HIV-1 has increased susceptibility to an NRTI, NNRTI, or INSTI on a display of the computer. In certain embodiments, the methods further comprise printing that the HIV-1 has increased susceptibility to an NRTI, NNRTI, or INSTI. In certain embodiments, the methods further comprise displaying that the HIV-1 has decreased susceptibility to an NRTI, NNRTI, or INSTI on a display of the computer. In certain embodiments, the methods further comprise printing that the HIV-1 has decreased susceptibility to an NRTI, NNRTI, or INSTI.

In another aspect, the invention provides a tangible medium comprising data indicating that an HIV-1 has altered susceptibility to an NRTI, NNRTI, or INSTI because of the presence of one or more mutations correlated with altered susceptibility to an NRTI, NNRTI, or INSTI as disclosed herein. In certain embodiments, the tangible medium is a paper document indicating that an HIV-1 is has altered susceptibility to an NRTI, NNRTI, or INSTI. In certain embodiments, the paper document is a printed document, e.g., a computer print-out. In certain embodiments, the tangible medium is a computer-readable medium comprising data indicating that an HIV-1 is has altered susceptibility to an NRTI, NNRTI, or INSTI. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an IPOD® (portable media player). In certain embodiments, the HIV-1 with altered susceptibility to an NRTI, NNRTI, or INSTI has reduced susceptibility. In certain embodiments, the HIV-1 with altered susceptibility to an NRTI, NNRTI, or INSTI has increased susceptibility.

In still another aspect, the invention provides an article of manufacture that comprises computer-readable instructions for performing a method of the invention. In certain embodiments, the article of manufacture is a random-access memory. In certain embodiments, the article of manufacture is a fixed disk. In certain embodiments, the article of manufacture is a floppy disk. In certain embodiments, the article of manufacture is a portable memory device, such as, e.g., a USB key or an IPOD® (portable media player).

In yet another aspect, the invention provides a computer-readable medium that comprises data that that can be utilized in conjunction with a method to determine whether an HIV-1 and computer-readable instructions for performing a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an IPOD® (portable media player).

In yet another aspect, the invention provides a computer system that is configured to perform a method of the invention.

5.4.4 Viruses and Viral Samples

A mutation associated with altered susceptibility to an NRTI, NNRTI, or INSTI according to the present invention can be present in any type of virus. For example, such mutations may be identified in any virus that infects animals known to one of skill in the art without limitation. In one embodiment of the invention, the virus includes viruses known to infect mammals, including dogs, cats, horses, sheep, cows etc. In certain embodiment, the virus is known to infect primates. In preferred embodiments, the virus is known to infect humans. Examples of such viruses that infect humans include, but are not limited to, human immunodeficiency virus ("HIV"), herpes simplex virus, cytomegalovirus virus, varicella zoster virus, other human herpes viruses, influenza A, B and C virus, respiratory syncytial virus, hepatitis A, B and C viruses, rhinovirus, and human papilloma virus. In certain embodiments, the virus is HCV. In other embodiments, the virus is HBV. In a preferred embodiment of the invention, the virus is HIV. Even more preferably, the virus is human immunodeficiency virus type 1 ("HIV-1"). The foregoing are representative of certain viruses for which there is presently available anti-viral chemotherapy and represent the viral families retroviridae, herpesviridae, orthomyxoviridae, paramyxoviridae, picornaviridae, flaviviridae, pneumoviridae and hepadnaviridae. This invention can be used with other viral intections clue to other viruses within these families as well as viral infections arising from viruses in other viral families for which there is or there is not a currently available therapy.

A mutation associated with altered susceptibility to an NRTI, NNRTI, or INSTI according to the present invention can be found in a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, a mutation associated with altered susceptibility to an NRTI, NNRTI, or INSTI according to the present invention is present in a virus that can be obtained from a culture. In some embodiments, the culture can be obtained from a laboratory. In other embodiments, the culture can be obtained from a collection, for example, the American Type Culture Collection.

In certain embodiments, a mutation associated with altered susceptibility to an NRTI, NNRTI, or INSTI according to the present invention is present in a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. Pat. Nos. 5,837,464 and 6,242,187 and PCT publication, WO 99/67427, each of which is incorporated herein by reference. In certain embodiments, the genes can be those that encode for a protease or reverse transcriptase.

In another embodiment, the intact virus need not be used. Instead, a part of the virus incorporated into a vector can be used. Preferably that part of the virus is used that is targeted by an anti-viral drug.

In another embodiment, a mutation associated with altered susceptibility to an NRTI, NNRTI, or INSTI according to the present invention is present in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure.

In certain embodiments, the virus is HIV and the selective pressure is an NNRTI. In another embodiment, the virus is HIV-1 and the selective pressure is an NNRTI. Any NNRTI can be used to apply the selective pressure. Examples of NNRTIs include, but are not limited to, nevirapine, delavirdine and efavirenz. By treating HIV cultured in vitro with an NNRTI, one can select for mutant strains of HIV that have an increased resistance to the NNRTI. The stringency of the selective pressure can be manipulated to increase or decrease the survival of viruses not having the selected-for characteristic.

In other embodiments, the virus is HIV and the selective pressure is a NRTI. In another embodiment, the virus is HIV-1 and the selective pressure is a NRTI. Any NRTI can be used to apply the selective pressure. Examples of NRTIs include, but are not limited to, AZT, ddI, ddC, d4T, 3TC, abacavir, and tenofovir. By treating HIV cultured in vitro with a NRTI, one can select for mutant strains of HIV that have an increased resistance to the NRTI. The stringency of the selective pressure can be manipulated to increase or decrease the survival of viruses not having the selected-for characteristic.

In still other embodiments, the virus is HIV and the selective pressure is a PI. In another embodiment, the virus is HIV-1 and the selective pressure is a PI. Any PI can be used to apply the selective pressure. Examples of PIs include, but are not limited to, saquinavir, ritonavir; inctinavir, neltinavir, amprenavir, lopinavir and atazanavir. By treating HIV cultured in vitro with a PI, one can select for mutant strains of HIV that have an increased resistance to the PI. The stringency of the selective pressure can be manipulated to increase or decrease the survival of viruses not having the selected-for characteristic.

In still other embodiments, the virus is HIV and the selective pressure is an entry inhibitor. In another embodiment, the virus is HIV-1 and the selective pressure is an entry inhibitor. Any entry inhibitor can be used to apply the selective pressure. An example of a entry inhibitor includes, but is not limited to, fusion inhibitors such as, for example, enfuvirtide. Other entry inhibitors include co-receptor inhibitors, such as, for example, AMD3100 (Anormed). Such co-receptor inhibitors can include any compound that interferes with an interaction between HIV and a co-receptor, e.g., CCR5 or CRCX4, without limitation. By treating HIV cultured in vitro with an entry inhibitor, one can select for mutant strains of HIV that have an increased resistance to the entry inhibitor. The stringency of the selective pressure can be manipulated to increase or decrease the survival of viruses not having the selected-for characteristic.

In still other embodiments, the virus is HIV and the selective pressure is an INSTI. In another embodiment, the virus is HIV-1 and the selective pressure is an INSTI. Any INSTI can be used to apply the selective pressure. Examples of INSTIs include, but are not limited to, diketo acid 1, diketo acid 2, and L-870,810. By treating HIV cultured in vitro with an INSTI, one can select for mutant strains of HIV that have an increased resistance to the INSTI. The stringency of the selective pressure can be manipulated to increase or decrease the survival of viruses not having the selected-for characteristic.

In another aspect, a mutation associated with altered susceptibility to an NRTI, NNRTI, or INSTI according to the present invention can be made by mutagenizing a virus, a viral genome, or a part of a viral genome. Any method of mutagenesis known in the art can be used for this purpose. In certain embodiments, the mutagenesis is essentially random. In certain embodiments, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, Proc. Nat. Acad. Sci. USA 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, a mutation associated with altered susceptibility to an NRTI, NNRTI, or INSTI can be made using site-directed mutagenesis. Any method of site-directed mutagenesis known in the art can be used (see e.g., Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY). See, e.g., Sarkar and Sommer, 1990, *Biotechniques,* 8:404-407. The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV reverse transcriptase. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains that are resistant or susceptible or hypersusceptible to one or more antiviral agents. In another embodiment, the mutagenized nucleotides encode amino acid residues that are adjacent to or near in the primary sequence of the protein residues known or suspected to interact with an anti-viral compound or known or suspected to be mutated in viral strains that are resistant or susceptible or hypersusceptible to one or more antiviral agents. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having an altered replication capacity. In another embodiment, the mutagenized nucleotides encode amino acid residues in or near the active site of a protein that is known or suspected to bind to an anti-viral compound.

6. EXAMPLES

6.1 Example 1

Measuring NRTI or NNRTI Resistance Using Vectors Comprising Patient Derived Segments Corresponding to the HIV Protease and Reverse Transcriptase (PR-RT) Coding Regions This example provides methods and compositions for accurately and reproducibly measuring the resistance or sensitivity of HIV-1 to antiretroviral drugs including, for example, NRTIs such as AZT and NNRTIs such as EFV, DLV, and/or NVP. The methods for measuring resistance or susceptibility to such drugs can be adapted to other HIV strains, such as HIV-2, or to other viruses, including, but not limited to hepadnaviruses (e.g., human hepatitis B virus), flaviviruses (e.g., human hepatitis C virus) and herpesviruses (e.g., human cytomegalovirus).

Drug resistance tests can be carried out, for example, using the methods for phenotypic drug susceptibility and resistance tests described in U.S. Pat. No. 5,837,464 (International Publication Number WO 97/27319) which is hereby incorporated by reference in its entirety, or according to the protocol that follows.

Patient-derived segments corresponding to the HIV protease and reverse transcriptase coding regions (hereinafter "PR-RT) were amplified by the reverse transcription-polymerase chain reaction method (RT-PCR) using viral RNA isolated from viral particles present in the plasma or serum of HIV-infected individuals as follows. Viral RNA was isolated from the plasma or serum using oligo-dT magnetic beads (Dynal Biotech, Oslo, Norway), followed by washing and elution of viral RNA. The RT-PCR protocol was divided into two steps. A retroviral reverse transcriptase (e.g. Moloney MuLV reverse transcriptase (Roche Molecular Systems, Inc., Branchburg, N.J.; Invitrogen, Carlsbad, Calif.), or avian myeloblastosis virus (AMV) reverse transcriptase, (Boehringer Mannheim, Indianapolis, Ind.)) was used to copy viral RNA into cDNA. The cDNA was then amplified using a thermostable DNA polymerase (e.g. Taq (Roche Molecular Systems, Inc., Branchburg, N.J.), Tth (Roche Molecular Systems, Inc., Branchburg, N.J.), PRIMEZYME. (enzyme_isolated from Thermus brockianus, Biometra, Gottingen, Germany)) or a combination of thermostable polymerases as described for the performance of "long PCR" (Barnes, W. M., 1994, Proc. Natl. Acad. Sci, USA 91, 2216-20) (e.g. Expand High Fidelity PCR System (Taq+Pwo), (Boehringer Mannheim. Indianapolis, Ind.); GENEAMP® XL PCR kit (PCR kit using_Tth+Vent), (Roche Molecular Systems, Inc., Branchburg, N.J.); or ADVANTAGE II®, Clontech, Palo Alto, Calif.)

PCR primers were designed to introduce ApaI and PinAI recognition sites into the 5' or 3' end of the PCR product, respectively.

Resistance test vectors incorporating the "test" patient-derived segments were constructed as described in U.S. Pat. No. 5,837,464 using an amplified DNA product of 1.5 kB prepared by RT-PCR using viral RNA as a template and oligonucleotides PDS Apa, PDS Age, PDS PCR6, Apa-gen, Apa-c, Apa-f, Age-gen, Age-a, RT-ad, RT-b, RT-c, RT-f, and/or RT-g as primers, followed by digestion with ApaI and AgeI or the isoschizomer PinAI. To ensure that the plasmid DNA corresponding to the resultant fitness test vector comprises a representative sample of the HIV viral quasi-species present in the serum of a given patient, many (>250) independent *E. coli* transformants obtained in the construction of a given fitness test vector were pooled and used for the preparation of plasmid DNA.

A packaging expression vector encoding an amphotrophic MuLV 4070A env gene product enables production in a resistance test vector host cell comprising the vector alone viral particles which can efficiently infect human target cells. Vectors encoding all HIV genes with the exception of env were used to transfect a packaging host cell (once transfected the host cell is referred to as a fitness test vector host cell). The packaging expression vector which encodes the amphotrophic MuLV 4070A env gene product is used with the resistance test vector to enable production in the resistance test vector host cell of infectious pseudotyped resistance test vector viral particles.

Drug resistance tests performed with resistance test vectors were carried out using packaging host and target host cells consisting of the human embryonic kidney cell line 293.

Resistance tests were carried out with resistance test vectors using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

The resistance test vectors containing a functional luciferase gene cassette were constructed as described above and host cells were transfected with the resistance test vector DNA. The resistance test vectors contained patient-derived reverse transcriptase and protease DNA sequences that encode proteins which were either susceptible or resistant to the antiretroviral agents, such as, for example, NRTIs, NNRTIs, and PIs.

The amount of luciferase activity detected in infected cells is used as a direct measure of "infectivity," i.e., the ability of the virus to complete a single round of replication. Thus, drug resistance or sensitivity can be determined by plotting the amount of luciferase activity produced by patient derived viruses in the presence of varying concentrations of the antiviral drug. By identifying the concentration of drug at which luciferase activity is half-maximum, the $IC_{50}$ of the virus from which patient-derived segment(s) were obtained for the antiretroviral agent can be determined.

Host (293) cells were seeded in 10-cm-diameter dishes and were transfected one day after plating with resistance test vector plasmid DNA and the envelope expression vector. Transfections were performed using a calcium-phosphate co-precipitation procedure. The cell culture media containing the DNA precipitate was replaced with fresh medium, from one to 24 hours, after transfection. Cell culture medium containing resistance test vector viral particles was harvested one to four days after transfection and was passed through a 0.45-mm filter before optional storage at $-80°$ C. Before infection, target cells (293 cells) were plated in cell culture media. Control infections were performed using cell culture media from mock transfections (no DNA) or transfections containing the resistance test vector plasmid DNA without the envelope expression plasmid. One to three or more days after infection the media was removed and cell lysis buffer (Promega Corp.; Madison, Wis.) was added to each well. Cell lysates were assayed for luciferase activity. Alternatively, cells were lysed and luciferase was measured by adding Steady-Glo (Promega Corp.; Madison, Wis.) reagent directly to each well without aspirating the culture media from the well. The amount of luciferase activity produced in infected cells was normalized to adjust for variation in transfection efficiency in the transfected host cells by measuring the luciferase activity in the transfected cells, which is not dependent on viral gene functions, and adjusting the luciferase activity from infected cell accordingly.

6.2 Example 2

Measuring NRTI, NNRTI, or INSTI Resistance Using Resistance Test Vectors Comprising Patient Derived Segments Corresponding to the Entire pol Gene or a Portion Thereof This example provides methods and compositions for accurately and reproducibly measuring the resistance or sensitivity of HIV infecting a patient to antiretroviral drugs including. The methods for measuring resistance or susceptibility to such drugs can be adapted to other viruses, including, but not limited to hepadnaviruses (e.g., human hepatitis B virus), flaviviruses (e.g., human hepatitis C virus) and herpesviruses (e.g., human cytomegalovirus). The methods described in this example can also be used to determine the replication capacity of the HIV.

The drug resistance tests described herein are a modification of the methods for phenotypic drug susceptibility and resistance tests described in U.S. Pat. No. 5,837,464 (International Publication Number WO 97/27319) which is hereby incorporated by reference in its entirety.

6.2.1 Construction of Resistance Test Vector Libraries

Patient-derived segment(s) corresponding to the entire pol gene, encoding HIV protease, reverse transcriptase (including RNAse H), and integrase (hereinafter "POL"), the portion of pol encoding amino acids 1-305 of reverse transcriptase (hereinafter "PR-RT"), the portion of pol encoding amino acids 319-440 of reverse transcriptase (including RNAse H), and integrase (hereinafter "RHIN"), were amplified by the reverse transcription-polymerase chain reaction method (RT-PCR) using viral RNA isolated from viral particles present in the plasma or serum of HIV-infected individuals as described below. The portion of pol encoding protease, amino acids 1-531 of reverse transcriptase (including RNase H) (hereinafter "PRRT-RH"), or the portion of pol encoding protease, reverse transcriptase (including RNAse H) and integrase (hereinafter "PRRT-RHIN"), were assembled from amplicons described above by standard recombinant DNA techniques involving a KpnI restriction site at amino acid 400 or a Pin A1 site at amino acid 315.

Virus was pelleted by centrifugation at 20,400×g for 60 min from plasma (typically, 1 ml) prepared from blood samples collected in evacuated tubes containing either EDTA, acid-citrate dextrose, or heparin as an anticoagulant. Virus particles were disrupted by resuspending the pellets in 200 [1.1 of lysis buffer (4 M guanidine thiocyanate, 0.1 M Tris HCl (pH 8.0), 0.5% sodium lauryl sarcosine, 1% dithiothreitol). RNA was extracted from viral lysates by using oligo(dT) linked to magnetic beads (Dynal, Oslo, Norway). Reverse transcription was performed with Superscript III (Invitrogen) at 50 degrees for 1 hour using primer 1. All primer sequences are listed in Table 1, below.

TABLE 1

| | | Reverse Transcriptase Primer | | |
|---|---|---|---|---|
| Name | SEQ ID NO. | Gene Primer is Located in | Sequence | Amplicon |
| Primer 1 | SEQ ID NO: 1 | vif | 5' CTTTCCTCGAGAYATACATATGGTGT 3' | POL and RHIN |

| | | PCR Primers | | | |
|---|---|---|---|---|---|
| Name | SEQ ID NO. | Gene Primer is Located in | Sequence | Amplicon | Direction |
| Primer 2 | SEQ ID NO: 2 | pol | 5' CAGRGARATTCTAAAAGAACCGGTACATGG 3' | RHIN | 5' |
| Primer 3 | SEQ ID NO: 3 | gag | 5' TTGCAGGGCCCCTAGRAAAAARGGCTG 3' | POL | 5' |
| Primer 4 | SEQ ID NO: 4 | vif | 5' CTTTCCTCGAGAYATACATATGGTGTTTTAC 3' | POL and RHIN | 3' |

From the resultant cDNA either POL or RHIN sequences were amplified using the Advantage High Fidelity PCR kit (BD Biosciences; Clontech). POL amplification products are made using forward Primer 3 containing an ApaI site and reverse Primer 4 containing a Xho 1 site. RHIN amplification products are made using forward Primer 2 containing a P1NA1 site and reverse Primer 4 containing a Xho 1 site. PCR cycling involves 40 cycles of a 3 step program according to the protocol shown in Table 2, below.

TABLE 2

| PCR PROFILE | DEGREES | MINUTES |
|---|---|---|
| AMPLIFICATION PROTOCOL FOR RHIN | | |
| DENATURE | 94 | 2:00 |
| 40 CYCLES OF: | | |
| DENATURE | 94 | 0:40 |
| ANNEAL | 60 | 1:00 |
| EXTEND | 72 | 2:00 |
| EXTENSION | 72 | 10:00 |
| HOLD | 4 | INDEF |
| AMPLIFICATION OF POL | | |
| DENATURE | 94 | 2:00 |
| 40 CYCLES OF: | | |
| DENATURE | 94 | 0:40 |
| ANNEAL | 58 | 1:00 |
| EXTEND | 72 | 3:00 |
| EXTENTSION | 72 | 10:00 |
| HOLD | 4 | INDEF |

A retroviral vector designed to measure antiretroviral drug susceptibility was constructed by using an infectious molecular clone of HIV-1. The vector, referred to herein as an indicator gene viral vector (IGVV), is replication defective and contains a luciferase expression cassette inserted within a deleted region of the envelope (env) gene. The IGVV is described in U.S. Pat. No. 5,837,464 (International Publication Number WO 97/27319) which is hereby incorporated by reference in its entirety. This retroviral vector was further modified to allow insertion of either the entire pol gene (POL) or the portion of poi encoding amino acids 319-440 of reverse transcriptase, the RNase H portion of reverse transcriptase, and integrase (REIN) by engineering an Xho 1 restriction enzyme recognition site into vif. Prior to doing this, an Xho 1 site in nef was deleted. Resistance Test vectors (RTVs) were constructed by incorporating amplified POL or RHIN into the IGVV by using ApaI and XhoI or PinAI and Xho 1 restriction sites respectively. RTVs were prepared as libraries (pools) in order to capture and preserve the pol or RHIN sequence heterogeneity of the virus in the patient. POL amplification products were digested with ApaI and XhoI, purified by agarose gel electrophoresis, and ligated to ApaI- and XhoI-digested IGVV DNA. RHIN amplification products were digested with PinAI and Xho/, purified by agarose gel electrophoresis, and ligated to PinAI and XhoI-digested IGVV DNA. Ligation reactions were used to transform competent Escherichia coli (Invitrogen, Carlsbad, Calif.). An aliquot of each transformation was plated onto agar, and colony counts were used to estimate the number of patient-derived segments represented in each RTV library. RTV libraries that comprised less than 50 members are not considered representative of the patient virus.

A packaging expression vector encoding an amphotrophic MuLV 4070A env gene product (described in U.S. Pat. No. 5,837,464) enables production in a host cell of viral particles which can efficiently infect human target cells. RTV libraries encoding all HIV genes with the exception of env, produced as described above, were used to transfect a packaging host cell. The packaging expression vector which encodes the amphotrophic MuLV 4070A env gene product is used with the resistance test vector to enable production of infectious pseudotyped viral particles comprising the resistance test vector libraries.

6.2.2 Anti-HIV Drug Resistance Assays with Resistance Test Vectors Comprising Different POL Sequences Drug resistance tests performed with test vectors were carried out using packaging host and target host cells consisting of the human embryonic kidney cell line 293.

Resistance tests were carried out with the RTV libraries by using viral particles comprising the RTV libraries to infect a host cell in which the expression of the indicator gene is measured. The amount of indicator gene (luciferase) activity detected in infected cells is used as a direct measure of "infectivity," i.e., the ability of the virus to complete a single round of replication. Thus, drug resistance or sensitivity can be determined by plotting the amount of luciferase activity produced by patient derived viruses in the presence of varying concentrations of the antiviral drug. By identifying the concentration of drug at which luciferase activity is half-maximum, the IC50 of the virus from which patient-derived segment(s) were obtained for the antiretroviral agent can be determined. The IC50 provides a direct measure of the resistance or susceptibility of the HIV infecting the patient to the antiviral drug.

In the resistance tests, packaging host (293) cells were seeded in 10-cm-diameter dishes and were transfected one day after plating with test vector plasmid DNA and the envelope expression vector. Transfections were performed using a calcium-phosphate co-precipitation procedure. The cell culture media containing the DNA precipitate was replaced with fresh medium, from one to 24 hours, after transfection. Cell culture medium containing viral particles comprising the TV libraries was harvested one to four days after transfection and was passed through a 0.45-mm filter before optional storage at −80° C. Before infection, host cells (293 cells) to be infected were plated in cell culture media containing varying concentrations of L-870,810, the anti-HIV agent to be tested in the assay. Control infections were performed using cell culture media from mock transfections (no DNA) or transfections containing the test vector plasmid DNA without the envelope expression plasmid. One to three or more days after infection the media was removed and cell lysis buffer (Promega Corp.; Madison, Wis.) was added to each well. Cell lysates were assayed for luciferase activity. Alternatively, cells were lysed and luciferase was measured by adding Steady-Glo (Promega Corp.; Madison, Wis.) reagent directly to each well without aspirating the culture media from the well. The amount of luciferase activity produced in infected cells was normalized to adjust for variation in transfection efficiency in the transfected host cells by measuring the luciferase activity in the transfected cells, which is not dependent on viral gene functions, and adjusting the luciferase activity from infected cell accordingly. The normalized luciferase activity was then plotted as a function of the log of anti-HIV agent present to determine the IC50 of the assayed HIV.

6.2.3 Anti-HIV Drug Resistance Assays Using Different Resistance Test Vectors

Different types of resistance test vectors were constructed and used as described in Example 1 and Example 2. As described in Example 1, resistance test vectors comprising patient-derived segments corresponding to the HIV-protease and reverse transcriptase coding region from patient viruses were constructed. Further, as described in Example 2, resistance test vectors comprising patient-derived segments corresponding to the entire pol gene, encoding HIV protease, reverse transcriptase (including RNAse H), and integrase ("POL"), and the portion of pol encoding amino acids 1-305 of reverse transcriptase ("PR-RT"), from the above patient viruses were constructed.

Assays using these resistance test vectors were performed for 27 different patient samples using the 3 different amplicons to assess the resistance to NNRTIs of HIV isolated from HIV-infected patients. Results (fold change in IC50 or "FC") for each of these different amplicons prepared from the same patient samples were compared to assess the difference.

FIG. 1 shows that overall there are no statistical difference in resistance to three NNRTIs between the resistance test vectors comprising POL and those comprising PR-RT (student's test, P>0.3). However certain samples displayed lower or higher levels of resistance when tested using the POL amplicon compared to the PR-RT amplicon.

6.3 Example 3

Identifying Mutations Correlated with Resistance to an NNRTI

This example provides methods and compositions for identifying mutations that correlate with resistance to an NNRT1. Resistance test vectors derived from patient samples or clones derived from the resistance test vector pools were tested in a resistance assay to determine accurately and quantitatively the relative EFV, DLV, or NVP resistance or susceptibility compared to the median observed resistance or susceptibility.

6.3.1 Identification of Mutations that Correlate with Resistance to an NNRTI

To identify mutations associated with NNRTI resistance, the drug resistance assays were performed as described in Examples 1 and 2. In these assays, POL, PR-RT and RHIN sequences from 27 HIV patient viruses were successfully amplified and tested for resistance to EFV, NVP and DLV. Viruses that exhibit an $10_50$ 2.5 fold higher than wild-type virus were designated as having reduced susceptibility to the respective NNRTI. The results of the assays testing the susceptibility of HIV isolated from 27 HIV-infected patients are presented in Table 3.

As shown in Table 3, nearly all patient samples exhibited consistent fold change values to all three NNRTIs for the three different amplicons (POL, PR-RI and RHIN). However, one patient sample, sample 62, exhibited divergent results in the assays using the POL-based resistance test vector from that using the PR-RT-based resistance test vector. In particular, sample 62 exhibited 6- to 10-fold higher fold change ("FC") to NNRTIs when the POL-based resistance test vector were used in comparison to the PR-RT-based resistance test vectors (e.g., EFV FC was 202-fold for the POL-based resistance vectors, While EFV FC was only 20-fold for the PR-RT-based resistance test vectors).

To further explore this result, resistant test vectors comprising patient-derived segments corresponding to different domain of pol gene from sample 62 were constructed. Diagrammatic representations of these constructs are presented as FIG. 2. Resistance assays to NVP using these different resistance test vectors were performed. FIG. 3 shows NVP resistance results with different amplicons of sample 62. Amplicons of PRRT-RHIN or PRRT-RH exhibited >200, fold change to NVP, which is similar to the fold change of amplicon of POL. In contrast, amplicon of PR-RT exhibited only 64-fold change to NVP. As shown in Table 5, similar results were observed when resistance assays to DLV and EFV were performed using different amplicons of sample 62. These results suggest that mutations in the C-terminus of reverse transcriptase after codon 305 and/or in RNase H are responsible for the observed increase in resistance.

Next, genotypic analysis of patient sample 62 was performed. Patient HIV sample sequences were determined using viral RNA purification, RT/PCR and ABI chain terminator automated sequencing. The sequence that was determined was compared to that of a reference sequence, NL4-3. The genotype was examined for sequences that were different from the reference or pre-treatment sequence and correlated to the observed $IC_5 0$ for EFV, NVP, and DLV.

As shown in Table 4, genotypic analysis of different clones derived from patient sample 62 shows that the mutation at codon 369 of the reverse transcriptase of the HIV-1 was present in many clones exhibiting resistance to an NNRTI. In Table 4, "0" means that a particular clone does not contain a mutation at the respective codon of the reverse transcriptase of the HIV-1. "1" means that a particular clone contains a mutation at the respective codon of the reverse transcriptase of the HIV-1. Five out of six clones containing a mutation at codon 369 showed enhanced resistance. However, one clone containing a mutation at codon 369 did not show enhanced resistance. Without intending to be limited to any particular theory, it is believed that this clone comprises one or more mutations in addition to the mutation at codon 369, which can suppress NNRTI resistance conferred by the mutation at codon 369.

6.3.2 Mutation at Codon 369 of Reverse Transcriptase of HIV-1 Correlates with Resistance to an NNRTI To confirm that a mutation at codon 369 of the reverse transcriptase of the HIV-1 significantly correlates with resistance to an NNRTI, a site-directed T369I mutant was generated in an NL4-3 background using conventional techniques and tested for resistance to NNRTIs using the methods described above.

FIG. 4 demonstrates the T3691 mutation results in enhanced resistance to NVP. Resistance to NVP is shown by the increased 1050 of the site-directed mutants T369I compared with the control. This result was also observed for other NNRTIs. For NVP, the fold change for IC50 was 9.74; for DLV, the fold change of for $IC_{50}$ was 5.00; for EFV, the fold change for IC50 was 2.99. Taken together, these results indicate that the mutation T369I of reverse transcriptase of the HIV-1 significantly correlates with reduced susceptibility to an NNRTI.

Further, a site directed double mutant T369I/K103N was generated using conventional techniques and tested for resistance to an NNRTI using the methods described above. As shown in FIG. 5, T369I/K103N mutant exhibited enhanced resistance to NVP.

In addition, using conventional technique, the T369I mutation was introduced into a resistance test vector comprising PR-RT segment derived from patient sample 62, which comprises mutations A62V, Q102K, K103N, K122E, D123N, C162S, D177E, I178L, M184V, T200A, Q207E, T215Y, P243S, V245Q, A272P and R277K in reverse transcriptase. Among these mutations, K103N correlates with resistance to a number of NNRTIs, including NVP. This patient sample was tested for resistance to an NNRTI using the methods described above. FIG. 6 demonstrates that this resistance test vector with this genetic background exhibited enhanced resistance to NVP.

Taken together, these resistance assay data show a mutation at codon at 369 of reverse transcriptase of the HIV-1 in combination with a mutation at codon 103 significantly correlates with resistance to an NNRTI.

6.4 Example 4

Identifying Additional Mutations Correlated with Resistance to an NNRTI

This example provides methods and compositions for identifying mutations that correlate with resistance to an NNRTI. Resistance test vectors derived from patient samples or clones derived from the resistance test vector pools were tested in a resistance assay to determine accurately and quantitatively the relative EFV, DLV, or NVP resistance or susceptibility and replication capacity in the presence or absence of certain mutations.

6.4.1 Mutations at Codons 348, 369 and 399 of Reverse Transcriptase of the HIV-1 Correlate with Resistance to an NNRTI To identify additional mutations associated with resistance to an NNRTI, the DLV, EFV, and NVP susceptibility phenotypes for 52 samples, including the 27 samples analyzed in Example 3, were determined using the PR-RT and POL amplicons according to Examples 1 and 2. Of these samples, two samples exhibited 5-fold different DLV phenotypes, one sample exhibited 5-fold different EFV phenotypes, and five samples exhibited 5-fold different NVP phenotypes. See FIG. 7. Genotypic analysis of the samples with discordant phenotypes revealed mutations from wild-type (NL4-3) at, among others, positions 348, 369, and 399.

To confirm the importance of these positions, the number of samples with a mutation at one of these three positions was plotted against FC in NVP susceptibility. Samples with mutations in each of these three positions, particularly positions 348 and 369, clustered above and FC of 2.0, suggesting that mutations at these three positions might correlate with resistance. See FIG. 8.

6.4.2 Mutations at Codons 348, 369, and 399 of Reverse Transcriptase of HIV-1 Affect Resistance to NNRTIs To assess the effects of mutations at positions 348, 369, and 399, a series of site-directed mutants were constructed in an wild-type (NL4-3) background. The NNRTI susceptibility phenotypes of these mutants were then determined using the POL segment assay according to Example 2.

In particular, site-directed mutants were constructed in an NL4-3 background comprising N348I, T369I, E399D, or the combination of N348I and T369I. The FC in DLV, EFV, and NVP susceptibility for each mutant is shown in FIG. 9. As shown in FIG. 9, N348I, T369I, and the combination of N348I and T369I significantly affected susceptibility to all tested NNRTIs (FC>2), but E399D did not (FC<2).

Next, a series of site-directed mutants were constructed to assess the effects of combinations of N348I, T369I, and E399D with previously recognized NNRTI resistance mutations. In particular, mutants comprising N348I, T369I, and E399D were made in combination with G190S, with K103N, and with the combination of K103R and V179D. The effects of these combinations on DLV, EFV, and NVP susceptibility were tested using the POL segment assay according to the method describe in Example 2. The results from these experiments are presented as FIG. 10.

As shown in FIG. 10, combining any of N348I, T369I, and E399D with G190S, K103N, or the combination of K103R and V179D increased EFV and NVP resistance beyond that observed for G190S, K103N, or K103R and V179D alone. In fact, the only combination that did not result in significantly increased NNRTI resistance is the G190S and E399D combination in relation to DLV susceptibility. As shown in the table of FIG. 10, the G190S and E399D combination mutant exhibited the same FC in susceptibility to DLV relative to NL4-3 as the G190S mutant exhibited.

To further analyze the effects of N348I, T369I, and E399D on NNRTI resistance, an additional series of site directed mutants was constructed in non-wild-type backgrounds. In particular, site-directed mutants comprising the N348I, T369I, or E399D mutation were constructed in POL-containing test vectors obtained from three different patient samples. The genotypes of the patient samples were are shown in Table 6, below. Results from these experiments are presented as FIG. 11.

As shown in FIG. 11, addition of N348I and T369I mutations increased resistance to EFV, NVP, and DLV for all tested patient genotypes. The E399D mutation increased EFV, NVP, and DLV resistance in a patient 50 background, but not a patient 58 or patient 62 background.

6.5 Example 5

Identifying Additional Mutations Correlated with Resistance to AZT

This example describes the results of experiments to assess the effects of the novel NNRTI resistance mutations identified in Example 4, above.

First, the AZT susceptibility phenotypes for 52 samples were determined using the PR-RT and POL amplicons according to Examples 1 and 2. Of these samples, seven samples exhibited significantly different AZT phenotypes in the two different assays. See FIG. 12.

To assess the specific effects of mutations at positions 348, 369, and 399, a series of site-directed mutants were constructed in an wild-type (NL4-3) background. The AZT susceptibility phenotype of these mutants were then determined with a POL segment assay according to Example 2.

In particular, site-directed mutants were constructed in an NL4-3 background comprising N348I, T369I, E399D, or the combination of N348I and T369I. The FC in AZT susceptibility for each mutant is shown as FIG. 13. As shown in FIG. 13, N348I, T369I, and the combination of N348I and T369I reduced susceptibility to AZT (FC>2), but E399D did not (FC<2).

To further analyze the effects of N348I, T369I, and E399D on AZT resistance, an additional series of site directed mutants was constructed in non-wild-type backgrounds. In particular, site-directed mutants comprising the N348I, T369I, or E399D mutation were constructed in POL-containing test vectors obtained from two different patient samples. The genotypes of the patient samples are shown in Table 6, below. Results from these experiments are presented in FIG. 14.

As shown in FIG. 14, the N348I and T369I mutations increased resistance to AZT in all tested patient backgrounds. The E399D mutation did not significantly increase AZT resistance in either the patient 45 or patient 50 background.

6.6 Example 6

Assessing the Effects of NNRTI Resistance Mutations on Replication Capacity This example describes the results of experiments to assess the effects of the NNRTI resistance mutations analyzed in Example 4, above, on the replication capacity of HIV-1.

First, the replication capacities of certain of the site-directed mutants were determined by performing the phenotypic assay with the POL segment of Example 2 in the absence of any anti-HIV drug. By comparing the relative luciferase activity observed for the site directed mutants relative to a wild-type reference (NL4-3), the replication capacity of the mutants relative to wild-type was determined. The relative replication capacities for N348I, T369I, E399D, and the combination of N348I and T369I were determined. Further, the relative replication capacities for N348I, T369I, and E399D were determined in the presence and absence of the G190S mutation and the K103N mutation.

Results of these experiments are presented in FIG. 15. As shown in FIG. 15, only T369I significantly affected replication capacity in the absence of either G190S or K103N. The effect of the T369I mutation on replication Capacity was substantially increased by combining it with the N348I mutation. Further, in the presence of either G190S or K103N, each of the three mutations N348I, T369I, and E399D further reduced replication capacity.

In addition, the effects of the N348I, T369I, and E399D mutations on replication capacity were assessed in the patient backgrounds described above using the POL segment assay of Example 2. In particular, the replication capacities of the site-directed mutants comprising N348I, T369I, and E399D in the genetic background of patient 45, 50, 58, or 62 and compared to the patient samples without the mutations. Results are relative to wild-type and are presented in FIG. 16.

As shown in FIG. 16, the effects of the N348I, T369I, and E399D mutations on replication capacity were largely dependent on the patient genetic background. In all tested samples, the additional mutations reduced replication capacity, but the significance and degree of that reduction varied by patient. Of the N348I, T369I, and E399D mutations, only the T369I mutation consistently reduced replication capacity.

6.7 Example 6

Identifying Mutations Correlated with Altered Susceptibility to Integrase Inhibitors This example provides methods and compositions for identifying mutations that correlate with altered susceptibilities to integrase inhibitors. Resistance test vectors derived from patient samples or clones derived from the resistance test vector pools were tested in a resistance assay to determine accurately and quantitatively the relative resistance or susceptibility of samples to particular integrase inhibitors and the replication capacity of samples in the presence or absence of certain mutations.

6.7.1 Identification of Mutations Putatively Correlated with Altered Susceptibility to Integrase Inhibitors To identify mutations associated with altered susceptibility to integrase inhibitors, including the integrase strand transfer inhibitor ("INSTI") L-870,810, the resistance or susceptibility phenotypes for 128 patient samples were determined using the RHIN segment as described in Example 2, above. The FC in susceptibility relative to wild-type (NL4-3) was then plotted as a histogram showing the number of samples having particular fold-changes in susceptibility, as shown in FIG. 17.

To identify sequence variations that significantly affect susceptibility to L-870,810, all 128 samples were sequenced using conventional techniques. Three samples with increased FC relative to wild-type (i.e., reduced susceptibility) contained the T97A mutation, while the nine samples with greatest decrease in FC relative to wild-type (i.e., increased susceptibility; FC<0.5) contained the K156N mutation. Accordingly, mutations T97A and K156N were further investigated to assess their effects on resistance to integrase inhibitors.

6.7.2 Mutations at Codons 97 and 156 of HIV-1 Integrase Affect Resistance to Integrase Inhibitors To assess the effects of mutations at positions 97 and 156 of integrase, two site-directed mutants (T97A and K156N) were constructed in two different wild-type (NL4-3 and IIIB) genetic backgrounds. The INSTI susceptibility phenotypes of these mutants to diketo acid 1, diketo acid 2, and L-870,810 were then determined using the RHIN segment assay according to Example 2.

In particular, site-directed mutants were constructed in an NL4-3 or IIIB background comprising either T97A or K156N. The FC in susceptibility to diketo acid 1, diketo acid 2, and L-870,810 for each mutant is shown as FIG. 18. As shown in FIG. 18, neither T97A nor K156N significantly affected susceptibility to diketo acid 1 or diketo acid 2 in either NL4-3 or IIIB backgrounds. However, T97A resulted in reduced susceptibility to L-870,810 in both NL4-3 and IIIB backgrounds, while K156N resulted in increased susceptibility to L-870,810 in both backgrounds. Thus, these experiments confirm that T97A is associated with resistance to L-870,810 and K156N is associated with increased susceptibility to L-870,810.

In addition, the replication capacities for the T97A and K156N mutants in the NL4-3 background were determined by comparing the luciferase activity of the RHIN segments comprising these mutations relative to a NL4-3 RHIN segment in the assay of Example 2 in the absence of an INSTI. As shown in FIG. 19, T97A resulted in significantly reduced replication capacity, while K156N did not significantly affect replication capacity.

Next, a series of site-directed mutants were constructed to assess the effects of combinations of T97A and K156N with previously recognized INSTI resistance mutations. In particular, mutants comprising T97A, K156N, and the combination of T97A and K156N were made in combination with three constellations of previously recognized INSI mutations (V72I, F121Y, and T125K; N155S; and T66I and M154I). Each of these combinations was made in a IIIB background. The effects of these combinations on diketo acid 1, diketo acid 2, and L-870,810 susceptibility were tested with the RHIN segment assay according to the method described in Example 2. The results from these experiments are presented in FIG. 20.

As shown in FIG. 20, adding T97A, K156N, or the combination of T97A and K156N to the combination V72I, F121Y, and T125K, to N155S, or to the combination T66I and M154I increased resistance to diketo acid 1 and diketo acid 2 beyond that observed for the previously recognized INSTI resistance mutations alone. Thus, both T97A and K156N result in decreased susceptibility to diketo acid 1 and diketo acid 2 beyond that attributable to the previously recognized constellations.

As also shown in FIG. 20, the T97A mutation also resulted in increased resistance to L-870,810 either alone or in combination with V72I, F121Y, and T125K, with N155S, or with T66I and M154I. K156N resulted in a decrease in L-870,810 FC between about 1.8 and 2.6 fold for the combinations tested. This effect of K156N was often observed in the presence of the T97A mutation. Thus, these results demonstrate that T97A results in decreased susceptibility to L-870,810, while K156N usually increases susceptibility to L870,810.

All references cited herein are incorporated by reference in their entireties.

The examples provided herein, both actual and prophetic are merely embodiments of the present invention and are not intended to limit the invention in any way.

TABLE 3

Drug Resistance Results of 27 Patient Samples

| Sample ID | NVP | | | | DLV | | | |
|---|---|---|---|---|---|---|---|---|
| | pol | PR-RT | RHIN | pol/PR-RT ratio | pol | PR-RT | RHIN | pol/PR-RT ratio |
| Sample 31 | 400.0 | 88.4 | 2.1 | 4.5 | 28.0 | 16.4 | 1.1 | 1.7 |
| Sample 33 | 25.1 | 23.3 | 1.0 | 1.1 | 5.7 | 8.7 | 0.7 | 0.7 |
| Sample 34 | 0.3 | 0.3 | 0.7 | 1.3 | 0.4 | 0.5 | 0.7 | 1.0 |
| Sample 35 | 28.3 | 25.2 | 1.2 | 1.1 | 5.4 | 6.5 | 0.8 | 0.8 |
| Sample 36 | 2.4 | 13.0 | 1.0 | 0.2 | 1.9 | 6.7 | 0.9 | 0.2 |
| Sample 38 | 81.0 | 114.0 | 0.5 | 0.7 | 66.0 | 128.0 | 0.5 | 0.5 |
| Sample 39 | 2.8 | 0.3 | 2.6 | 9.0 | 1.2 | 0.2 | 1.2 | 5.1 |
| Sample 42 | 7.1 | 34.0 | 0.6 | 0.2 | 0.2 | 0.4 | 0.5 | 0.5 |
| Sample 45 | 0.3 | 0.3 | 1.3 | 1.1 | 0.1 | 0.1 | 1.0 | 0.7 |
| Sample 47 | 400.0 | 400.0 | 1.0 | 1.0 | 5.4 | 6.2 | 0.6 | 0.9 |
| Sample 50 | 72.7 | 153.9 | 0.6 | 0.5 | 65.4 | 250.0 | 0.4 | 0.3 |
| Sample 51 | 0.7 | 0.4 | 0.6 | 1.6 | 0.3 | 0.3 | 0.4 | 0.9 |
| Sample 52 | 1.8 | 2.0 | 0.9 | 0.9 | 2.7 | 3.1 | 0.9 | 0.8 |
| Sample 58 | 400.0 | 400.0 | 1.7 | 1.0 | 250.0 | 149.6 | 1.5 | 1.7 |
| Sample 62 | 400.0 | 64.0 | 7.6 | 6.3 | 140.0 | 16.0 | 3.4 | 8.8 |
| Sample 64 | 0.3 | 1.0 | 0.4 | 0.3 | 0.3 | 1.6 | 0.3 | 0.2 |
| Sample 69 | 1.6 | 1.0 | 0.9 | 1.6 | 1.8 | 1.4 | 0.7 | 1.2 |
| Sample 72 | 1.1 | 0.7 | 1.6 | 1.6 | 1.2 | 0.9 | 1.7 | 1.4 |
| Sample 80 | 17.0 | 46.0 | 0.72 | 0.4 | 22.0 | 65.0 | 0.58 | 0.3 |
| Sample 81 | 114.0 | 92.0 | 1.4 | 1.2 | 9.5 | 12.0 | 0.9 | 0.8 |
| Sample 84 | 0.9 | 0.8 | 0.7 | 1.2 | 0.5 | 0.9 | 0.4 | 0.6 |
| Sample 85 | 400.0 | 131.7 | 2.1 | 3.0 | 69.0 | 25.2 | 1.4 | 2.7 |
| Sample 87 | 1.4 | 0.8 | 1.9 | 1.7 | 0.7 | 0.7 | 1.3 | 0.9 |
| Sample 89 | 400.0 | 37.0 | 2.7 | 10.8 | 250.0 | 250.0 | 1.5 | 1.0 |
| Sample 90 | 400.0 | 400.0 | 1.2 | 1.0 | 4.8 | 4.1 | 0.6 | 1.1 |
| Sample 92 | 1.1 | 1.1 | 0.5 | 1.0 | 0.8 | 1.1 | 0.3 | 0.8 |
| Sample 93 | 1.4 | 1.6 | 1.1 | 0.9 | 0.2 | 0.3 | 0.7 | 0.6 |

| Sample ID | EFV | | | | NNRTI Mutations | T369 | Comments |
|---|---|---|---|---|---|---|---|
| | pol | PR-RT | RHIN | pol/PR-RT ratio | | | |
| Sample 31 | 56.0 | 22.8 | 1.1 | 2.5 | K103N | | |
| Sample 33 | 5.9 | 7.1 | 0.7 | 0.8 | K103S | | |
| Sample 34 | 0.6 | 0.4 | 1.0 | 1.4 | | | |

TABLE 3-continued

Drug Resistance Results of 27 Patient Samples

| Sample | | | | | | | |
|---|---|---|---|---|---|---|---|
| Sample 35 | 9.5 | 9.3 | 0.7 | 1.0 | K103H | | |
| Sample 36 | 2.2 | 6.7 | 1.0 | 0.3 | K103K/W | | Percentage of K103N in mixture in greater PRRT then pol |
| Sample 38 | 27.0 | 42.0 | 0.5 | 0.6 | K103N | | |
| Sample 39 | 1.0 | 0.3 | 0.9 | 4.0 | | T369A | |
| Sample 42 | 1.1 | 3.1 | 0.4 | 0.3 | G190G/A | | |
| Sample 45 | 0.2 | 0.2 | 1.0 | 1.0 | | | |
| Sample 47 | 30.2 | 123.9 | 0.5 | 0.2 | K103K/N, V106V/A, Y181Y/C, G190G/A | | V106 is WT in PRPT |
| Sample 50 | 24.1 | 63.2 | 0.5 | 0.4 | K103N | | |
| Sample 51 | 0.5 | 0.5 | 0.4 | 1.1 | | | |
| Sample 52 | 1.1 | 1.3 | 1.0 | 0.8 | | | |
| Sample 58 | 153.9 | 26.4 | 0.9 | 5.8 | K103N, Y181Y/C, G190G/A | | G190 WT in PRPT |
| Sample 62 | 202.0 | 20.0 | 1.8 | 10.1 | K103H, P225P/H | T369T/I | P225 is WT is pol |
| Sample 64 | 0.3 | 1.1 | 0.3 | 0.3 | | T369T/A | |
| Sample 69 | 1.2 | 0.8 | 0.8 | 1.6 | | | |
| Sample 72 | 0.8 | 0.5 | 1.0 | 1.5 | | | |
| Sample 80 | 6.3 | 11.0 | 0.52 | 0.6 | K103K/N, Y181Y/C | | |
| Sample 81 | 136.0 | 98.0 | 1.2 | 1.4 | K103N, P225H | | |
| Sample 84 | 0.7 | 0.7 | 0.5 | 1.0 | | | |
| Sample 85 | 77.0 | 22.0 | 1.2 | 3.5 | | | |
| Sample 87 | 1.0 | 0.9 | 1.3 | 1.1 | | | |
| Sample 89 | 700.0 | 700.0 | 1.2 | 1.0 | L100I, K103N | | |
| Sample 90 | 66.0 | 50.5 | 0.7 | 1.3 | K103K/N, Y181C, G190A | | X103 is WT in PRPT |
| Sample 92 | 0.8 | 1.0 | 0.3 | 0.8 | | | |
| Sample 93 | 0.7 | 0.8 | 0.9 | 0.8 | | | |

TABLE 4

Clonal Analysis of Patient Sample 62

| Clone ID | NVP FC | H315 | Y342 | N348 | Y354 | A355 | T369 | A371 | T377 | I393 | T403 | N418 | R448 | D511 | K550 |
|---|---|---|---|---|---|---|---|---|---|---|---|---|---|---|---|
| c28 | 0.54 | 0 | 0 | 0 | 0 | 0 | 0 | 0 | 1 | 1 | 1 | 0 | 1 | 0 | 0 |
| c03a | 1.64 | 0 | 0 | 0 | 0 | 0 | 0 | 0 | 1 | 0 | 1 | 0 | 0 | 0 | 0 |
| c16 | 2.19 | 0 | 0 | 0 | 0 | 0 | 0 | 0 | 1 | 0 | 1 | 0 | 0 | 0.5 | 0 |
| c15 | 2.37 | 0 | 0 | 1 | 1 | 0 | 0 | 0 | 0 | 0 | 1 | 1 | 0 | 0 | 0 |
| c18 | 2.46 | 0 | 0 | 0 | 0 | 0 | 0 | 1 | 1 | 0 | 1 | 0 | 0 | 0 | 0 |
| c20 | 3.97 | 0 | 0 | 0 | 0 | 0 | 0 | 0 | 1 | 0 | 1 | 0 | 0 | 0 | 0 |
| c24 | 4.77 | 0 | 0 | 0 | 0 | 0 | 0 | 0 | 1 | 0 | 1 | 0 | 0 | 0 | 0 |
| c21 | 5.16 | 0 | 0 | 0 | 0 | 0 | 0 | 0 | 1 | 0 | 1 | 0 | 0 | 0 | 1 |
| c03b | 5.51 | 0 | 0 | 0 | 0 | 1 | 1 | 0 | 1 | 0 | 1 | 0 | 0 | 0 | 0 |
| c14 | 6.48 | 0 | 1 | 0 | 0 | 0 | 0 | 0 | 1 | 0 | 1 | 0 | 1 | 0 | 0 |
| Pool | 7.61 | 0 | 0 | 0.5 | 0 | 0 | 0.5 | 0 | 1 | 0 | 1 | 0 | 0 | 0 | 0 |
| c12 | 9.18 | 0 | 0 | 0 | 0 | 0 | 1 | 0 | 1 | 0 | 1 | 0 | 0 | 0 | 0 |
| c23 | 10.11 | 0 | 0 | 0 | 0 | 0 | 1 | 0 | 1 | 0 | 1 | 0 | 0 | 0 | 0 |
| c26 | 12.00 | 0 | 0 | 0 | 0 | 0 | 1 | 0 | 1 | 0 | 1 | 0 | 0 | 0 | 0 |

TABLE 4-continued

Clonal Analysis of Patient Sample 62

| Clone ID | NVP FC | H315 | Y342 | N348 | Y354 | A355 | T369 | A371 | T377 | I393 | T403 | N418 | R448 | D511 | K550 |
|---|---|---|---|---|---|---|---|---|---|---|---|---|---|---|---|
| c08 | 12.98 | 1 | 0 | 0 | 0 | 0 | 1 | 0 | 1 | 0 | 0 | 0 | 0 | 0 | 0 |
| c10 | 28.07 | 0 | 0 | 1 | 0 | 0 | 0 | 0 | 1 | 0 | 1 | 0 | 0 | 0 | 0 |

TABLE 5

Resistance Results with Different Amplicons of Sample 62 (Fold Change in $IC_{50}$)

| Amplicon | DLV | EFV | NVP |
|---|---|---|---|
| RHIN | 3.36 | 1.83 | 7.61 |
| pol | 140.00 | 202.00 | 400.00 |
| PRRT | 16.00 | 20.00 | 64.00 |
| PRRT-RHIN | 140.00 | 202.00 | 400.00 |
| PRRT-RH | 250.00 | 276.90 | 400.00 |

TABLE 6

Reverse Transcriptase Genotypes of Patients 45, 50 58, and 62

| Patient 45 | Q23Q/., V35V/I, M41L, K43E, E44A, D67N, T69T/A, V75V/I VI, Q102K, V118I, D123E, C162S, D177E, M184M/V, G196E, Q207K, I1208Y, L210W, R211D/E, T215Y, S251I, A272P, R277K, V293I, K3111C/R, Q334N, K358R, G359G/S, A360T, A371V, K390R, K395R, E399D, A400T, I435V, K454R, P468S, T470D, H483Y, L491S, T497T/S, S519N, K527Q, L533L/M, A554S |
|---|---|
| Patient 50 | V35T, Q102K, K103N, K122E, C162S, R211K, V245E, I257L, K331K/R, T377M, V381V/I, T386I, K390R, T4031/M, I435I/A/T/V, E449E/D, V467I, K527N, A554S, L560L/F |
| Patient 58 | V35T, M41L, K43E/Q, K49R, A98A/G, Q102K, K103N, V118I, I1351/T, C162S, Y181Y/C, G190G/A, L210W, R211K, T215Y, L228L/H, T240T/K, R277K, T286A, V293I, E297K, V317V/A, I329L, R356K, IC3581C/R, A360V, T362T/P, E399D, A400T, I435V, A446S, L452S/T, D460N, P468S |
| Patient 62 | W24W/C, A62V, E89E/G, Q102K, K103N, K122E, D123N, 1135I/M, C162S, D177E, I178L, M184V, T200A, Q207E, T215Y, P243P/S, V245Q, A272P, R277K, R284R1G, S322A, N348N/I, K358R, H361H/P, T369T/I, T377M, S379C, A400T, T4031, E404D/N, I435V, L452Q, V4671, P468S, L469I, T470A, K476R, H483Y, S519N, K527N, K530R, A554N |

What is claimed is:

1. A method for determining whether a human immunodeficiency virus 1 (HIV-1) has reduced susceptibility to a non-nucleoside reverse transcriptase inhibitor (NNRTI), comprising:

(a) detecting the presence or absence of a mutation at codon 399 in combination with mutations in at least two of codons 103, 179, or 190 in a pol gene encoding reverse transcriptase of the HIV-1 using radioactive or fluorescent DNA sequencing, polymerase chain reaction (PCR), reverse transcription PCR (RTPCR), allele-specific restriction-endonuclease cleavage, mismatch-repair detection, binding of MutS protein, denaturing-gradient gel electrophoresis, single-strand-conformation polymorphism detection, RNAase cleavage at mismatched base-pairs, chemical or enzymatic cleavage of heteroduplex DNA, methods based on oligonucleotide-specific primer extension, genetic bit analysis, oligonucleotide-ligation assay, oligonucleotide-specific ligation chain reaction (LCR), gap-LCR, peptide nucleic acid (PNA) assays, Southern Blot analyses, or single stranded conformational polymorphism analyses (SSCP), wherein the codon number of said reverse transcriptase corresponds to the codon number in the wild type HIV-1 isolate NL4-3 sequence, and wherein the mutation at codon 399 encodes aspartic acid (D) instead of glutamic acid (E); the mutation at codon 103 encodes asparagine (N), arginine (R), serine (S), glutamine (Q), or threonine (T) instead of lysine (K); the mutation at codon 179 encodes aspartic acid (D) instead of valine (V); and the mutation at codon 190 encodes serine (S) instead of glycine (G); and (b) determining that the HIV-1 has reduced susceptibility to the NNRTI if the mutations are present.

2. The method of claim 1, wherein the presence or absence of mutations at codons 399, 179 and 103 are detected.

3. The method of claim 1, wherein the presence or absence of mutations at codons 399, 190 and 179 are detected.

4. The method of claim 1, wherein the presence or absence of mutations at codons 399, 103 and 190 are detected.

5. The method of claim 1, wherein the NNRTI is efavirenz (EFV), nevirapine (NVP), or delavirdine (DLV).

6. The method of claim 5, wherein the NNRTI is EFV.

7. The method of claim 5, wherein the NNRTI is NVP.

8. The method of claim 5, wherein the NNRTI is DLV.

9. The method of claim 1, further comprising:

c) treating the HIV with the NNRTI if the HIV is determined to be susceptible to the NNRTI in step (b).

10. The method of claim 1, further comprising:

c) treating the HIV with a different inhibitor if the HIV is determined to have reduced susceptibility to the NNRTI in step (b).

11. A method for selecting a treatment for a patient having a human immunodeficiency virus 1 (HIV- 1) infection, comprising:

a) obtaining an HIV from a patient;

b) determining whether the HIV is susceptible to a non-nucleoside reverse transcriptase inhibitor (NNRTI), comprising:

i) detecting the presence or absence of a mutation at codon 399 in combination with mutations in at least two of codons 103, 179, or 190 in a pol gene encoding reverse transcriptase of the HIV-1, wherein the codon number of said reverse transcriptase corresponds to the codon number in the wild type HIV-1 isolate NL4-3 sequence, and wherein the mutation at codon 399 encodes aspartic acid (D) instead of glutamic acid (E); the mutation at codon 103 encodes asparagine (N), arginine (R), serine (S), glutamine (Q), or threonine (T) instead of lysine (K); the mutation at codon 179 encodes aspartic acid (D) instead of valine (V); and the mutation at codon 190 encodes serine (S) instead of glycine (G); and ii) determining that the HIV-1 has reduced susceptibility to the NNRTI if the mutations are present; and c) treating the patient with the NNRTI if the HIV is susceptible to the NNRTI as determined in step b), or treating the patient with a different inhibitor if the HIV is determined to have reduced susceptibility to the NNRTI in step (b).

* * * * *

UNITED STATES PATENT AND TRADEMARK OFFICE
CERTIFICATE OF CORRECTION

PATENT NO. : 8,637,252 B2
APPLICATION NO. : 13/296370
DATED : January 28, 2014
INVENTOR(S) : Soumi Gupta et al.

It is certified that error appears in the above-identified patent and that said Letters Patent is hereby corrected as shown below:

Title Page, column 1, Line 19, Please insert -- Related U.S. Application Data (63) Divisional of application No. 11/916,632, filed Dec. 5, 2007, now U.S. Patent No. 8,071,284, which is a §371 National Phase Application of PCT Application No. PCT/US06/22072 filed Jun. 6, 2006. (60) Provisional application No. 60/688,171, filed Jun. 6, 2005. --.

Title Page 2, Item (56), column 1, Line 58, Please delete "Kehlenseck", please insert -- Kehlenbeck --.

In the Specification

Column 3, Line 64, Please delete "poi", please insert -- pol --.

Column 13, Line 46, Please delete "PinA1", please insert -- *PinA1* --.

Column 16, Line 63, Please delete "reacmy", please insert -- readily --.

Column 18, Line 14, Please delete "IC50", please insert -- $IC_{50}$ --.

Column 18, Line 15, Please delete "IC50", please insert -- $IC_{50}$ --.

Column 18, Line 17, Please delete "IC50", please insert -- $IC_{50}$ --.

Column 28, Line 36, Please delete "[1.1", please insert -- µ1 --.

Column 30, Line 24, Please delete "IC50", please insert -- $IC_{50}$ --.

Column 30, Line 26, Please delete "IC50", please insert -- $IC_{50}$ --.

Column 30, Line 59, Please delete "IC50", please insert -- $IC_{50}$ --.

Column 31, Line 11, Please delete "IC50", please insert -- $IC_{50}$ --.

Column 31, Line 41, Please delete "$10_50$", please insert -- $IC_{50}$ --.

Column 31, Line 65, After ">200", please delete ",".

Column 32, Line 14, Please delete "$IC_50$", please insert -- $IC_{50}$ --.

Column 32, Line 43, Please delete "IC50", please insert -- $IC_{50}$ --.

Column 32, Line 45, Please delete "IC50", please insert -- $IC_{50}$ --.

Signed and Sealed this
Twenty-seventh Day of January, 2015

Michelle K. Lee
*Deputy Director of the United States Patent and Trademark Office*

CERTIFICATE OF CORRECTION (continued)
U.S. Pat. No. 8,637,252 B2

Column 33, Line 62, Please delete "N3481, T3691,", please insert -- N348I, T369I, --.

Column 37, Sample 35, column PR-RT, Please delete "6.5", please insert -- 6.8 --.

Column 37, Sample 36, column PR-RT, Please delete "6.7", please insert -- 8.7 --.

Column 37, Sample 90, column pol/PR-RT ratio, Please delete "0.6", please insert -- 0.8 --.

Column 39, Sample 35, column NNRTI Mutations, Please delete "K103H", please insert -- K103N --.

Column 39, Sample 36, column NNRTI Mutations, Please delete "K103K/W", please insert -- K103K/N --.

Column 39, Sample 90, column NNRTI Mutations, Please delete "PRPT", please insert -- PRRT --.

Column 42, Table 6, Patient 45, Line 2, Please delete "11208Y," please insert -- H208Y --.

Column 42, Table 6, Patient 58, Line 4, Please delete "IC3581C/R," please insert -- K358K/R, --.

Column 42, Table 6, Patient 62, Line 2, Please delete "1178L," please insert -- I178L, --.

Column 42, Table 6, Patient 62, Line 3, Please delete "R284R1G," please insert -- R284R/G, --.

Column 42, Table 6, Patient 62, Line 4, Please delete "T4031," please insert -- T403I, --.

SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (13)..(13)
<223> OTHER INFORMATION: y is a pyrimidine base

<400> SEQUENCE: 1
ctttcctcga gayatacata tggtgt                                    26

<210> SEQ ID NO 2
<211> LENGTH: 30
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (4)..(4)
<223> OTHER INFORMATION: r is a purine base
<220> FEATURE:

```
<221> NAME/KEY: misc_feature
<222> LOCATION: (7)..(7)
<223> OTHER INFORMATION: r is a purine base

<400> SEQUENCE: 2
cagrgaratt ctaaaagaac cggtacatgg                                        30

<210> SEQ ID NO 3
<211> LENGTH: 27
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (16)..(16)
<223> OTHER INFORMATION: r is a purine base
<220> FEATURE:
<221> NAME/KEY: misc_feature
<222> LOCATION: (22)..(22)
<223> OTHER INFORMATION: r is a purine base

<400> SEQUENCE: 3
ttgcagggcc cctagraaaa arggctg                                           27

<210> SEQ ID NO 4
<211> LENGTH: 31
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (13)..(13)
<223> OTHER INFORMATION: y is a pyrimidine base

<400> SEQUENCE: 4
ctttcctcga gayatacata tggtgtttta c                                      31

<210> SEQ ID NO 5
<211> LENGTH: 14825
<212> TYPE: DNA
<213> ORGANISM: Human immunodeficiency virus type 1
<300> PUBLICATION INFORMATION:
<308> DATABASE ACCESSION NUMBER: GenBank Accession No. AF324493.2
<309> DATABASE ENTRY DATE: 2010-05-24
<313> RELEVANT RESIDUES IN SEQ ID NO: (1)..(14825)

<400> SEQUENCE: 5
tggaagggct aatttggtcc caaaaaagac aagagatcct tgatctgtgg atctaccaca      60
cacaaggcta cttccctgat tggcagaact acacaccagg ccagggatc agatatccac      120 tgacctttgg atggtgcttc aagttagtac cagttgaacc agagcaagta gaagaggcca    180
atgaaggaga gaacaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta gcctcaata aagcttgcct    540 tgagtgctca agtagtgtg tgcccgtctg ttgtgtgact ctggtaacta gagatccctc    600 agacccttt agtcagtgtg gaaaatctct agcagtggcg cccgaacagg acttgaaag    660 cgaaagtaaa gccagaggag atctctcgac gcaggactcg gcttgctgaa gcgcgcacgg    720
```

```
caagaggcga ggggcggcga ctggtgagta cgccaaaaat tttgactagc ggaggctaga      780
aggagagaga tgggtgcgag agcgtcggta ttaagcgggg gagaattaga taaatgggaa      840
aaaattcggt taaggccagg gggaagaaa caatataaac taaaacatat agtatgggca       900
agcagggagc tagaacgatt cgcagttaat cctggccttt tagagacatc agaaggctgt      960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200 ctccagggc aaatggtaca tcaggccata tcacctagaa cttaaatgc atgggtaaa       1260 gtagtagaag agaaggcttt cagcccagaa gtaatacca tgttttcagc attatcagaa     1320
ggagccaccc cacaagattt aaataccatg ctaaacacag tggggggaca tcaagcagcc    1380
atgcaaatgt taaagagac catcaatgag gaagctgcag aatgggatag attgcatcca     1440
gtgcatgcag ggcctattgc accaggccag atgagagaac caaggggaag tgacatagca    1500
ggaactacta gtaccttca ggaacaaata ggatggatga cacataatcc acctatccca     1560
gtaggagaaa tctataaag atggataatc ctgggattaa ataaaatagt aagaatgtat     1620
agccctacca gcattctgga cataagacaa ggaccaaagg aacccttag agactatgta     1680 gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga agaaatgatg acagcatgtc agggagtggg gggacccggc    1860
cataaagcaa gagttttggc tgaagcaatg agccaagtaa caaatccagc taccataatg    1920
atacagaaag gcaattttag gaaccaaaga aagactgtta agtgtttcaa ttgtggcaaa    1980
gaagggcaca tagccaaaaa ttgcagggcc cctaggaaaa agggctgttg gaaatgtgga    2040
aaggaaggac accaaatgaa agattgtact gagagacagg ctaattttt agggaagatc     2100 tggccttccc acaagggaag gccagggaat tttcttcaga gcagaccaga gccaacagcc    2160
ccaccagaag agagcttcag gtttggggaa gagacaacaa ctccctctca gaagcaggag    2220
ccgatagaca aggaactgta tcctttagct tccctcagat cactctttgg cagcgacccc    2280
tcgtcacaat aaagataggg gggcaattaa aggaagctct attagataca ggagcagatg    2340
atacagtatt agaagaaatg aatttgccag gaagatggaa accaaaaatg ataggggga    2400 ttggaggttt tatcaaagta agacagtatg atcagatact catagaaatc tgcggacata    2460
aagctatagg tacagtatta gtaggaccta cacctgtcaa cataattgga agaaatctgt    2520
tgactcagat tggctgcact ttaaatttc ccattagtcc tattgagact gtaccagtaa     2580
aattaaagcc aggaatggat ggcccaaaag ttaaacaatg gccattgaca gaagaaaaa     2640 taaaagcatt agtagaaatt tgtacagaaa tggaaaagga aggaaaaatt tcaaaaattg    2700
ggcctgaaaa tccatacaat actccagtat ttgccataaa gaaaaaagac agtactaaat    2760
ggagaaaatt agtagatttc agagaactta ataagaaac tcaagatttc tgggaagttc     2820
aattaggaat accacatcct gcagggttaa aacagaaaaa atcagtaaca gtactggatg    2880
tgggcgatgc atatttttca gttcccttag ataaagactt caggaagtat actgcattta    2940
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
```

```
ctgacttaga aatagggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540
agcaggggca aggccaatgg acatatcaaa tttatcaaga gccatttaaa aatctgaaaa    3600
caggaaagta tgcaagaatg aagggtgccc acactaatga tgtgaaacaa ttaacagagg    3660
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaacttttc tatgtagatg ggcagccaat agggaaacta    3900
aattaggaaa agcaggatat gtaactgaca gaggaagaca aaaagttgtc cccctaacgg    3960
acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagataaat    4200
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaagaaaaa ttataggaca ggtaagagat caggctgaac    4740
atcttaagac agcagtacaa atggcagtat tcatccacaa ttttaaaaga aaaggggggg    4800
ttgggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gttttcaga atctgctata    5400
agaaatacca tattaggacg tatagttagt cctaggtgtg aatatcaagc aggacataac    5460
aaggtaggat ctctacagta cttggcacta gcagcattaa taaaaccaaa acagataaag    5520
```

```
ccacctttgc ctagtgttag gaaactgaca gaggacagat ggaacaagcc ccagaagacc      5580
aagggccaca gagggagcca tacaatgaat ggacactaga gcttttagag gaacttaaga      5640
gtgaagctgt tagacatttt cctaggatat ggctccataa cttaggacaa catatctatg      5700
aaacttacgg ggatacttgg gcaggagtgg aagcctataa aagaattctg caacaactgc      5760
tgtttatcca tttcagaatt gggtgtcgac atagcagaat aggcgttact cgacagagga      5820
gagcaagaaa tggagccagt agatcctaga ctagagccct ggaagcatcc aggaagtcag      5880
cctaaaactg cttgtaccaa ttgctattgt aaaaagtgtt gctttcattg ccaagtttgt      5940
ttcatgacaa aagccttagg catctcctat ggcaggaaga agcggagaca cgacgaaga      6000 gctcatcaga acagtcagac tcatcaagct tctctatcaa agcagtaagt agtacatgta      6060
atgcaaccta aatagtagc aatagtagca ttagtagtag caataataat agcaatagtt      6120
gtgtggtcca tagtaatcat agaatatagg aaaatattaa gacaaagaaa aatagacagg      6180
ttaattgata gactaataga aagagcagaa gacagtggca atgagagtga aggagaagta      6240
tcagcacttg tggagatggg ggtggaaatg gggcaccatg ctccttggga tattgatgat      6300
ctgtagtgct acagaaaaat tgtgggtcac agtctattat ggggtacctg tgtggaagga      6360
agcaaccacc actctatttt gtgcatcaga tgctaaagca tatgatacag aggtacataa      6420
tgtttgggcc acacatgcct gtgtacccac agaccccaac ccacaagaag tagtattggt      6480
aaatgtgaca gaaaattta acatgtggaa aaatgacatg gtagaacaga tgcatgagga      6540
tataatcagt ttatgggatc aaagcctaaa gccatgtgta aaattaaccc cactctgtgt      6600
tagtttaaag tgcactgatt tgaagaatga tactaatacc aatagtagta gcgggagaat      6660
gataatggag aaaggagaga taaaaaactg ctctttcaat atcagcacaa gcataagaga      6720
taaggtgcag aaagaatatg cattcttta taaacttgat atagtaccaa tagataatac      6780
cagctatagg ttgataagtt gtaacacctc agtcattaca caggcctgtc caaaggtatc      6840
ctttgagcca attcccatac attattgtgc cccggctggt tttgcgattc taaaatgtaa      6900
taataagacg ttcaatggaa caggaccatg tacaaatgtc agcacagtac aatgtacaca      6960
tggaatcagg ccagtagtat caactcaact gctgttaaat ggcagtctag cagaagaaga      7020
tgtagtaatt agatctgcca atttcacaga caatgctaaa accataatag tacagctgaa      7080
cacatctgta gaaattaatt gtacaagacc caacaacaat acaagaaaaa gtatccgtat      7140
ccagagggga ccaggagag catttgttac aataggaaaa ataggaaata tgagacaagc      7200
acattgtaac attagtagag caaaatgaa tgccacttta aaacagatag ctagcaaatt      7260
aagagaacaa tttggaaata ataaaacaat aatctttaag caatcctcag gaggggaccc      7320
agaaattgta acgcacagtt ttaattgtgg aggggaattt ttctactgta attcaacaca      7380
actgtttaat agtacttggt ttaatagtac ttggagtact gaagggtcaa ataacactga      7440
aggaagtgac acaatcacac tcccatgcag aataaaacaa tttataaaca tgtggcagga      7500
agtaggaaaa gcaatgtatg cccctcccat cagtggacaa attagatgtt catcaaatat      7560
tactgggctg ctattaacaa gagatggtgg taataacaac aatgggtccg agatcttcag      7620
acctggagga ggcgatatga gggacaattg gagaagtgaa ttatataaat ataaagtagt      7680
aaaaattgaa ccattaggag tagcacccac caaggcaaag agaagagtgg tgcagagaga      7740
aaaaagagca gtgggaatag gagctttgtt ccttgggttc ttgggagcag caggaagcac      7800
tatgggcgca gcgtcaatga cgctgacggt acaggccaga caattattgt ctgatatagt      7860
gcagcagcag aacaatttgc tgagggctat tgaggcgcaa cagcatctgt tgcaactcac      7920
```

```
agtctggggc atcaaacagc tccaggcaag aatcctggct gtggaaagat acctaaagga   7980
tcaacagctc ctgggatttt ggggttgctc tggaaaactc atttgcacca ctgctgtgcc   8040
ttggaatgct agttggagta ataaatctct ggaacagatt tggaataaca tgacctggat   8100
ggagtgggac agagaaatta acaattacac aagcttaata cactccttaa ttgaagaatc   8160
gcaaaaccag caagaaaaga atgaacaaga attattggaa ttagataaat gggcaagttt   8220
gtggaattgg tttaacataa caaattggct gtggtatata aaattattca taatgatagt   8280
aggaggcttg gtaggtttaa gaatagtttt tgctgtactt tctatagtga atagagttag   8340
gcagggatat tcaccattat cgtttcagac ccacctccca atcccgaggg gacccgacag   8400
gcccgaagga atagaagaag aaggtggaga gagagacaga gacagatcca ttcgattagt   8460
gaacggatcc ttagcactta tctgggacga tctgcggagc ctgtgcctct tcagctacca   8520
ccgcttgaga gacttactct tgattgtaac gaggattgtg gaacttctgg gacgcagggg   8580
gtgggaagcc ctcaaatatt ggtggaatct cctacagtat tggagtcagg aactaaagaa   8640
tagtgctgtt aacttgctca atgccacagc catagcagta gctgagggga cagatagggt   8700
tatagaagta ttacaagcag cttatagagc tattcgccac ataccctagaa gaataagaca   8760
gggcttggaa aggattttgc tataagatgg gtggcaagtg gtcaaaaagt agtgtgattg   8820
gatggcctgc tgtaagggaa agaatgagac gagctgagcc agcagcagat ggggtgggag   8880
cagtatctcg agacctagaa aaacatggag caatcacaag tagcaataca gcagctaaca   8940
atgctgcttg tgcctggcta gaagcacaag gaggaggaaga ggtgggtttt ccagtcacac   9000
ctcaggtacc tttaagacca atgacttaca aggcagctgt gatcttagc cactttttaa   9060
aagaaaaggg gggactggaa gggctaattc actcccaaag aagacaagat atccttgatc   9120
tgtggatcta ccacacacaa ggctacttcc ctgattggca gaactacaca ccagggccag   9180
gggtcagata tccactgacc tttggatggt gctacaagct agtaccagtt gagccagata   9240
aggtagaaga ggccaataaa ggagagaaca ccagcttgtt acaccctgtg agcctgcatg   9300
gaatggatga ccctgagaga gaagtgttag agtggaggtt tgacagccgc ctagcatttc   9360
atcacgtggc ccgagagctg catccggagt acttcaagaa ctgctgacat cgagcttgct   9420
acaagggact ttccgctggg gactttccag ggaggcgtgg cctgggcggg actgggagt   9480
ggcgagccct cagatgctgc atataagcag ctgcttttg cctgtactgg gtctctctgg   9540
ttagaccaga tctgagcctg ggagctctct ggctaactag ggaacccact gcttaagcct   9600
caataaagct tgccttgagt gcttcaagta gtgtgtgccc gtctgttgtg tgactctggt   9660
aactagagat ccctcagacc cttttagtca gtgtggaaaa tctctagcac ccaggaggta   9720
gaggttgcag tgagccaaga tcgcgccact gcattccagc ctgggcaaga aaacaagact   9780
gtctaaaata ataataataa gttaagggta ttaaatatat ttatacatgg aggtcataaa   9840
aatatatata tttgggctgg gcgcagtggc tcacacctgc gcccggccct ttgggaggcc   9900
gaggcaggtg gatcacctga gtttgggagt tccagaccag cctgaccaac atggagaaac   9960
cccttctctg tgtatttta gtagatttta ttttatgtgt attttattca caggtatttc   10020
tggaaaactg aaactgtttt cctctactc tgataccaca agaatcatca gcacagagga   10080
agacttctgt gatcaaatgt ggtgggagag ggaggttttc accagcacat gagcagtcag   10140
ttctgccgca gactcggcgg gtgtccttcg gttcagttcc aacaccgcct gcctggagag   10200
aggtcagacc acagggtgag ggctcagtcc caagacata aacacccaag acataaacac   10260
ccaacaggtc caccccgcct gctgcccagg cagagccgat tcaccaagac gggaattagg   10320
```

```
atagagaaag agtaagtcac acagagccgg ctgtgcggga gaacggagtt ctattatgac   10380
tcaaatcagt ctccccaagc attcggggat cagagttttt aaggataact tagtgtgtag   10440
ggggccagtg agttggagat gaaagcgtag ggagtcgaag gtgtccttt gcgccgagtc   10500
agttcctggg tgggggccac aagatcggat gagccagttt atcaatccgg gggtgccagc   10560
tgatccatgg agtgcagggt ctgcaaaata tctcaagcac tgattgatct taggttttac   10620
aatagtgatg ttaccccagg aacaatttgg ggaaggtcag aatcttgtag cctgtagctg   10680
catgactcct aaaccataat ttctttttg tttttttt tttatttttg agacagggtc   10740
tcactctgtc acctaggctg gagtgcagtg gtgcaatcac agctcactgc agcctcaacg   10800
tcgtaagctc aagcgatcct cccacctcag cctgcctggt agctgagact acaagcgacg   10860
ccccagttaa ttttgtatt tttggtagag gcagcgtttt gccgtgtggc cctggctggt   10920
ctcgaactcc tgggctcaag tgatccagcc tcagcctccc aaagtgctgg gacaaccggg   10980
gccagtcact gcacctggcc ctaaaccata atttctaatc ttttggctaa tttgttagtc   11040
ctacaaaggc agtctagtcc ccaggcaaaa aggggggttg tttcgggaaa gggctgttac   11100
tgtctttgtt tcaaactata aactaagttc ctcctaaact tagttcggcc tacacccagg   11160
aatgaacaag gagagcttgg aggttagaag cacgatggaa ttggttaggt cagatctctt   11220
tcactgtctg agttataatt ttgcaatggt ggttcaaaga ctgcccgctt ctgacaccag   11280
tcgctgcatt aatgaatcgg ccaacgcgcg gggagaggcg gtttgcgtat gggcgctct   11340
tccgcttcct cgctcactga ctcgctgcgc tcggtcgttc ggctgcggcg agcggtatca   11400
gctcactcaa aggcggtaat acggttatcc acagaatcag gggataacgc aggaaagaac   11460
atgtgagcaa aaggccagca aaaggccagg aaccgtaaaa aggccgcgtt gctggcgttt   11520
ttccataggc tccgcccccc tgacgagcat cacaaaaatc gacgctcaag tcagaggtgg   11580
cgaaacccga caggactata aagataccag gcgtttcccc ctggaagctc cctcgtgcgc   11640
tctcctgttc cgaccctgcc gcttaccgga tacctgtccg cctttctccc ttcgggaagc   11700
gtggcgcttt ctcatagctc acgctgtagg tatctcagtt cggtgtaggt cgttcgctcc   11760
aagctgggct gtgtgcacga accccccgtt cagcccgacc gctgcgcctt atccggtaac   11820
tatcgtcttg agtccaaccc ggtaagacac gacttatcgc cactggcagc agccactggt   11880
aacaggatta gcagagcgag gtatgtaggc ggtgctacag agttcttgaa gtggtggcct   11940
aactacggct acactagaag aacagtattt ggtatctgcg ctctgctgaa gccagttacc   12000
ttcggaaaaa gagttggtag ctcttgatcc ggcaaacaaa ccaccgctgg tagcggtggt   12060
ttttttgttt gcaagcagca gattacgcgc agaaaaaaag gatctcaaga agatcctttg   12120
atcttttcta cggggtctga cgctcagtgg aacgaaaact cacgttaagg gattttggtc   12180
atgagattat caaaaaggat cttcacctag atccttttaa attaaaaatg aagttttaaa   12240
tcaatctaaa gtatatatga gtaaacttgg tctgacagtt accaatgctt aatcagtgag   12300
gcacctatct cagcgatctg tctatttcgt tcatccatag ttgcctgact ccccgtcgtg   12360
tagataacta cgatacggga gggcttacca tctggcccca gtgctgcaat gataccgcga   12420
gacccacgct caccggctcc agatttatca gcaataaacc agccagccgg aagggccgag   12480
cgcagaagtg gtcctgcaac tttatccgcc tccatccagt ctattaattg ttgccgggaa   12540
gctagagtaa gtagttcgcc agttaatagt ttgcgcaacg ttgttgccat tgctacaggc   12600
atcgtggtgt cacgctcgtc gtttggtatg gcttcattca gctccggttc ccaacgatca   12660
aggcgagtta catgatcccc catgttgtgc aaaaaagcgg ttagctcctt cggtcctccg   12720
```

```
atcgttgtca gaagtaagtt ggccgcagtg ttatcactca tggttatggc agcactgcat    12780
aattctctta ctgtcatgcc atccgtaaga tgcttttctg tgactggtga gtactcaacc    12840
aagtcattct gagaatagtg tatgcggcga ccgagttgct cttgcccggc gtcaatacgg    12900
gataataccg cgccacatag cagaacttta aaagtgctca tcattggaaa acgttcttcg    12960
gggcgaaaac tctcaaggat cttaccgctg ttgagatcca gttcgatgta acccactcgt    13020
gcacccaact gatcttcagc atcttttact ttcaccagcg tttctgggtg agcaaaaaca    13080
ggaaggcaaa atgccgcaaa aaagggaata agggcgacac ggaaatgttg aatactcata    13140
ctcttccttt ttcaatatta ttgaagcatt tatcagggtt attgtctcat gagcggatac    13200
atatttgaat gtatttagaa aaataaacaa ataggggttc cgcgcacatt tccccgaaaa    13260
gtgccacctg acgtctaaga aaccattatt atcatgacat aacctataaa aataggcgt     13320
atcacgaggc cctttcgtct cgcgcgtttc ggtgatgacg gtgaaaacct ctgacacatg    13380
cagctcccgg agacggtcac agcttgtctg taagcggatg ccgggagcag acaagcccgt    13440
cagggcgcgt cagcgggtgt tggcgggtgt cggggctggc ttaactatgc ggcatcagag    13500
cagattgtac tgagagtgca ccatatgcgg tgtgaaatac cgcacagatg cgtaaggaga    13560
aaataccgca tcaggcgcca ttcgccattc aggctgcgca actgttggga agggcgatcg    13620
gtgcgggcct cttcgctatt acgccagggg aggcagagat tgcagtaagc tgagatcgca    13680
gcactgcact ccagcctggg cgacagagta agactctgtc tcaaaaataa aataaataaa    13740
tcaatcagat attccaatct tttcctttat ttatttattt attttctatt ttggaaacac    13800
agtccttcct tattccagaa ttacacatat attctatttt tctttatatg ctccagtttt    13860
ttttagacct tcacctgaaa tgtgtgtata caaaatctag gccagtccag cagagcctaa    13920
aggtaaaaaa taaaataata aaaaataaat aaaatctagc tcactccttc acatcaaaat    13980
ggagatacag ctgttagcat taaataccaa ataacccatc ttgtcctcaa taattttaag    14040
cgcctctctc caccacatct aactcctgtc aaaggcatgt gccccttccg ggcgctctgc    14100
tgtgctgcca accaactggc atgtggactc tgcagggtcc ctaactgcca agccccacag    14160
tgtgccctga ggctgcccct tccttctagc ggctgccccc actcggcttt gctttcccta    14220
gtttcagtta cttgcgttca gccaaggtct gaaactaggt gcgcacagag cggtaagact    14280
gcgagagaaa gagaccagct ttacagggg tttatcacag tgcaccctga cagtcgtcag    14340
cctcacaggg ggtttatcac attgcaccct gacagtcgtc agcctcacag ggggtttatc    14400
acagtgcacc cttacaatca ttccatttga ttcacaattt ttttagtctc tactgtgcct    14460
aacttgtaag ttaaatttga tcagaggtgt gttcccagag gggaaaacag tatatacagg    14520
gttcagtact atcgcatttc aggcctccac ctggtcttg gaatgtgtcc cccgagggt     14580
gatgactacc tcagttggat ctccacaggt cacagtgaca caagataacc aagacacctc    14640
ccaaggctac cacaatgggc cgccctccac gtgcacatgg ccgaggaac tgccatgtcg     14700
gaggtgcaag cacacctgcg catcagagtc cttggtgtgg agggagggac cagcgcagct    14760
tccagccatc cacctgatga acagaaccta gggaaagccc cagttctact tacaccagga    14820
aaggc                                                               14825
```